United States Patent [19]
Cook et al.

[11] Patent Number: 6,166,199
[45] Date of Patent: Dec. 26, 2000

[54] N-2 SUBSTITUTED PURINES

[75] Inventors: Phillip Dan Cook, San Marcos; Kanda S. Ramasamy, Laguna Hills; Muthiah Manoharan, Carlsbad, all of Calif.

[73] Assignee: Isis Pharmaceuticals, Inc, Carlsbad, Calif.

[21] Appl. No.: 09/128,834

[22] Filed: Aug. 4, 1998

Related U.S. Application Data

[60] Continuation of application No. 08/762,587, Dec. 10, 1996, Pat. No. 5,808,027, which is a division of application No. 08/473,450, Jun. 7, 1995, Pat. No. 5,587,469, which is a division of application No. 08/159,088, Nov. 29, 1993, Pat. No. 5,459,255, which is a continuation-in-part of application No. PCT/US91/00243, which is a continuation-in-part of application No. 07/854,634, Jul. 1, 1992, abandoned, which is a continuation-in-part of application No. 07/463,358, Jan. 11, 1990, abandoned, which is a continuation-in-part of application No. 07/566,977, Aug. 13, 1990, abandoned.

[51] Int. Cl.$^7$ .......................... C07H 19/00; C07H 19/167
[52] U.S. Cl. .................. 536/27.2; 536/27.13; 536/27.61; 536/22.1; 536/23.1; 536/27.6; 536/27.21; 536/27.8; 536/27.81
[58] Field of Search .................................. 536/22.1, 23.1, 536/27.13, 27.6, 27.21, 27.2, 27.61, 27.8, 27.81

[56] References Cited

U.S. PATENT DOCUMENTS

| | | |
|---|---|---|
| 3,654,262 | 4/1972 | Walton et al. . |
| 4,381,344 | 4/1983 | Rideout et al. . |
| 4,511,713 | 4/1985 | Miller et al. . |
| 4,689,320 | 8/1987 | Kaji . |
| 4,719,295 | 1/1988 | Cook et al. . |
| 4,760,017 | 7/1988 | McCormick . |
| 4,804,748 | 2/1989 | Seela . |
| 4,876,335 | 10/1989 | Yamane et al. . |
| 4,965,350 | 10/1990 | Inoue et al. . |
| 5,212,295 | 5/1993 | Cook . |
| 5,214,135 | 5/1993 | Srivastava et al. . |
| 5,216,141 | 6/1993 | Benner . |
| 5,359,051 | 10/1994 | Cook et al. . |
| 5,459,255 | 10/1995 | Cook et al. . |
| 5,587,469 | 12/1996 | Cook et al. . |
| 5,808,027 | 9/1998 | Cook et al. . |

FOREIGN PATENT DOCUMENTS

| | | |
|---|---|---|
| 0085440 | 8/1983 | European Pat. Off. . |
| 0260032 | 3/1988 | European Pat. Off. . |
| 0286028 | 10/1988 | European Pat. Off. . |
| 0329348 | 8/1989 | European Pat. Off. . |
| 0393920 | 10/1990 | European Pat. Off. . |
| 3010399 | 9/1981 | Germany . |
| 4110085 | 10/1992 | Germany . |
| WO 91/10671 | 7/1991 | WIPO . |

OTHER PUBLICATIONS

Agarwal, K.L. and Rifcina, "Synthesis and Enzymatic Properties of Deoxyribooligonucleotides Containing Methyl and Phenylphosphonate Linkages", *Nucleic Acids Research*, 1979, 6, 3009–3024.

Agrawal, S. et al., "Oligodeoxynucleoside Phosphoramidates and Phosphorothioates as Inhibitors of Human Immunodeficiency Virus" *PNAS USA*, 1988, 85, 7079–7083.

Agris, C.H. et al., "Inhibition of Vesicular Stomatitis Virus Protein Synthesis and Infection by Sequence–Specific Oligodeoxyribonucleoside Methylphosphonates", *Biochemistry*, 1986, 25, 6268–6275.

Arnott and Hukins, "Optimised Parameters for A–DNA and B–DNA" *Biochemical and Biophysical Research Communication*, 1970, 47, 1504–1510.

Beaucage, S. et al., "Deoxynucleoside phosphoramidites—A new class of key intermediates for deoxypolynucleotide synthesis", *Tetrahedron Letters*, 1981, 22, 1859–1862.

Bhat, V. et al., "A Simple and Convenient Method for the Selective N–Acylations of Cytosine Nucleosides", *Nucleosides and Nucleotides*, 1989, 8, 179–183.

Biggadike, K. et al., "Short convergent route to homochiral carbocylic 2'–deoxynucleosides and carbocyclic robonucleosides", *J. Chem. Soc. Chem. Commun.* 1987, 1083–1084.

Brill, W. et al., "Synthesis of oligodeoxynucleoside phosphorodithioates via thioamidites", *Journal of the American Chemical Society*, 1989, 111, 2321–2322.

Butke, G. et al., in "Nucleic Acid Chemistry," Part 3, pp. 149–152, Townsend, L.B. and Tipson, eds., J. Wiley and Sons, New York, 1986.

Caruthers, M., "Oligonucleotides. Antisense Inhibitors of Gene Expression", Cohen, J.S., ed., pp. 7–24, CRC Press, Inc., Boca Raton, FL, 1989.

Cazenave et al., "Enzymatic Amplification of Translation Inhibition of Rabbit β–globin mRNA Mediated by Anti–Messenger Oligodeoxynucleotides Covalently Linked to Intercalating Agents", *Nucleic Acid Research*, 1987, 15, 4717–4736.

(List continued on next page.)

*Primary Examiner*—James O. Wilson
*Attorney, Agent, or Firm*—Woodcock Washburn Kurtz Mackiewicz & Norris LLP

[57] ABSTRACT

This invention presents novel purine-based compounds for inclusion into oligonucleotides. The compounds of the invention, when incorporated into oligonucleotides are especially useful as "antisense" agents—agents that are capable of specific hybridization with a nucleotide sequence of an RNA. Oligonucleotides are used for a variety of therapeutic and diagnostic purposes, such as treating diseases, regulating gene expression in experimental systems, assaying for RNA and for RNA products through the employment of antisense interactions with such RNA, diagnosing diseases, modulating the production of proteins, and cleaving RNA in site specific fashions. The compounds of the invention include novel heterocyclic bases, nucleosides, and nucleotides. When incorporated into oligonucleotides, the compounds of the invention can be useful for modulating the activity of RNA.

22 Claims, No Drawings

OTHER PUBLICATIONS

Chen, Y. and Wu, "Studies on Fluoroalkylation and Fluroalkoxylation. Part 33. Direct Trifluoromethylation of Aryl Halides with Fluorosulphonyldfluoromethyl Iodide in the Presence of Copper: an Electron Transfer Induced Process", *Journal of Chemical Society Perkin Transactions,* 1989, 2385–2387.

Chladek, S. et al., "Facile Synthesis of 2'–Amino–2'–Deoxyadenosine", *Journal of Carbohydrates, Nucleosides & Nucleotides,* 1980, 7, 63–75.

Cohen, "Oligonucleotides: Antisense Inhibitors of Gene Expression", CRC Press, Inc., Boca Raton, FL, 1989.

Constant, J.F. et al., "Heterodimeric Molecules Including Nucleic Acid Bases and 9–Aminoacridine Spectroscopic Studies, Conformations, and Interactions with DNA", *Biochemistry,* 1988, 27, 3997–4003.

Cook et al., "Synthesis and Antiviral and Enzymatic Studies of Certain 3–Deazaguanines and Their Imidazolecarboxamide Precursors", *Journal of Medicinal Chemistry,* 1978, 21, 1212–1218.

Daves, G. and Cheng, "The Chemistry and Biochemistry of C–Nucleosides", *Progress in Medicinal Chemistry,* 1976, 13, 304–349.

De las Heras, F. et al., "3'–C–Cyano–3'–Deoxythymidine", *Tetrahedron Letters,* 1988, 29, 941–944.

Le Doan, P.L. et al., "Sequence–Targeted Chemical Modification of Nucleic Acids by Complimentary Oligonucleotides Covalently Linked to Porphyrins", *Nucleic Acids Research,* 1987, 15, 8643–8659.

Dreyer, G. and Dervan, "Sequence–specific cleavage of single–stranded DNA: Oligodeoxynucleotide–EDTA–Fe (II)", *PNAS USA,* 1985, 82, 968–972.

Eckstein, F. et al., "Polynucleotides Containing2'–Chloro–2'–Deoxyribose", *Biochemistry* 1972, 11, 4336–4344.

Fox, J. et al., "Nucleosides. XVIII. Synthesis of 2'–Fluorothymidine, 2'–Fluorodeoxyuridine, and Other 2'–Halogeno–2'–Deoxy Nucleosides", *Journal of Organic Chemistry,* 1964, 29, 558–564.

Freskos, J., "Synthesis of 2' Deoxypyrimidine Nucleosides Via Copper (I) Iodide Catalysis", *Nucleosides and Nucleotides,* 1989, 8, 1075–1076.

Gaffney, B. and Jones, "A New Strategy for the Protection of Deoxyguanosine During Oligonucleotide Synthesis", *Tetrahedron Letters,* 1982, 23, 2257–2260.

Gait, M.J., "Oligonucleotide Synthesis", IRL Press, 1985.

Guschlbauer, W. and Jankowski, "Nucleoside conformation is Determined by the Electronegativity of the Sugar Substituent", *Nucleic Acds Research,* 1980, 8, 1421–1433.

Hertel, L.W. et al., "Synthesis of 2–Deoxy–2, 2–difluoro-–D–ribose and 2–Deoxy–2, 2–difluoro–D–ribofuranosyl Nucleosides", *Journal of Organic Chemistry,* 1988, 53, 2406–2409.

Ikehara, M. et al., "Polynucleotides. LII.synthesis and properties of poly (2'–deox–2'–fluoroadenylic acid)", *Nucleic Acids Research,* 1978, 5, 1877–1887.

Ikehara, M. et al., "Polynucleotides. LVI. Synthesis and Properties of poly(2'–deoxy–2'–fluoroinosinic Acid)", *Nucleic Acids Research,* 1978, 5, 3315–3324.

Ikehara, M. et al., "A Linear Relationship Between Electronegativity of 2'–Substituents and conformation of Adenine Nucleosides", *Tetrahedron Letters,* 1979, 42, 4073–4076.

Ikehara, M. et al., "Recognition by Restriction Endonuclease EcoRI of Deoxyoctanucleotides Containing Modified Sugar Moieties", *European J. of Biochem.,* 1984, 139, 447–450.

Ikehara, M. et al., "Polynucleotides. L. synthesis and properties of poly (2'chloro–2'–deoxyadenylic acid) and poly (2'–bromo–2'–deoxyadenylic acid)", *Nucl. Acids Res.,* 1977, 4, 4249–4260.

Ikehara, M., "Studies of Nucleosides and Nucleotides–LXXXII. cyclonucleosides. (39).[2] synthesis and properties of 2'halogen–2'–deoxyadenosines", *Chemistry and Pharmaceutical Bulletin,* 1978, 26, 2449–2453.

Ikehara, M., "Purine 8–Cyclonucleosides", *Accounts of Chemical Research,* 1969, 2, 47–53.

Ikehara, M. et al., "Studies of Nucleosides and Nucleotides–LXXXIV[1]", *Tetrahedron,* 1978, 34, 1133–1138.

Ikehara, M. et al., "Studies of Nucleosides and Nucleotides–LXXXIX., Purine cyclonucleosides. (43). synthesis and properties of 2'halogen–2'–deoxyguanosines[1]", *Chem. and Pharm. Bull.,* 1981, 29, 3281–3285.

Ikehara, M. et al., "Improved Synthesis of 2'–Fluoro–2'–Deoxyadenosine and Synthesis and Carbon–13 NMR Spectrum of Its 3', 5'–Cyclic Phosphate Derivative", *Nucleosides and Nucleotides,* 1983, 2, 373–385.

Ikehara, M. et al., "Studies of Nucleosides and Nucleotides–LXXXVII.[1]", Purine cyclonulceosies. XLII. synthesis of 2' deoxy–2'fluorofunaosine", *Chem. and Pharm. Bull.,* 1981, 29, 1034–1038.

Ikehara, "Studies of Nucleosides and Nucleotides–LXXIX.1), Purine cyclonucleosides. (37). The total synthesis of an antibiotic 2'–amino–2'deoxyguanosine2)", *Chem. and Pharm. Bull.,* 1978, 26, 240–244.

Ikehara, M. et al., "Studies of Nucleosides and Nucleotides–LXV[1]", *Tetrahedron,* 1975, 31, 1369–1372.

Inoue, H. et al., "Synthesis and hybridization studies on two complementary nona(2'–O–methyl) ribonucleotides", *Nucl. Acids Res.,* 1987, 15, 6131–6148.

Iyer, R., Beaucage, Serge L. et al., "3H–1, 2–benzodithiole–3–one 1,1–dioxide as an improved sulfurizing reagent in the solid–phase synthesis of oligodeoxyribonucleoside phosphorothiioates", *J. Am. Chem. Soc.,* 1990, 112, 1253–1255.

Jager, A. et al., "Oligonucleotide N–Alkylphosphoramidates: Synthesis and Binding to Polynucleotides", *Biochem.,* 1988, 27, 7237–7246.

Jarvi, E.T. et al., "Synthesis and biological evaluation of dideoxynucleosides containing a difluoromethylene unit", *Nucleosides and Nucleotides,* 1989, 8, 1111–1114.

Jayaraman, K. et al., "Selective inhibition of *escherichia coli* protein synthesis and growth by nonionic oligonucleotides complementary to the 3'end of 16S rRNA", *PNAS USA,* 1981, 78, 1537–1541.

Jones, R.A., "Transient protection: Efficient one–flask synthesis of protected deoxynucleosides", *J. Am. Chem. Soc.,* 1982, 104, 1316–1319.

Jones, G. et al., "4'–substituted nucleosides. 5. hydroxymethylation of nucleoside 5'–aldehydes", *J. Org. Chem.,* 1979, 44, 1309–1317.

Balaban, I. and Pyman, "Bromo–Derivatives of Glyoxalin", *J. Chem. Soc.,* 1922, 121, 947–958.

Kazimierczuk, Z. et al., "Synthesis of 2'–deoxytubercidin, 2'–deoxyadenosine, and related 2'–deoxynucleosides via novel direct stereospecific sodium salt glycosylation procedure", *J. Am. Chem. Soc.,* 1984, 106, 6379–6382.

Knorre, D. and Vlassov, "Complementary–Addressed (Sequence–Specific) Modification of Nucleic Acids", *Progress in Nucleic Acid Research and Molecular Biology*, 1985, 32, 291–320.

Koole, L. et al., "Synthesis of phosphate–methylated DNA fragments using 9–fluorenylmethoxycarbonyl as transient base protecting group", *J. Org. Chem.*, 1989, 54, 1657–1664.

Letsinger, R. et al., "Effects of pendant groups at phosphorus on binding properties of d–ApA analogues", *Nucl. Acids Res.*, 1986, 14, 3487–3499.

Loose–Mitchell, D., "Antisense Nucleic Acids as a Potential Class of Pharmaceutical Agents", *TIPS*, 1988, 9, 45–47.

Marcus–Sekura, C.J. et al., "Comparative inhibition of chloramphenical acetyltransferase gene expression by antisense oligonucleotide analogues having alkyl phosphotriester, methylphosphonate and phosphorothioate linkages", *Nucl. Acid Res.*, 1987, 15, 5749–5763.

Marcus–Sekura, "Techniques for Using Antisense Oligodeoxyribonucleotides to Study Gene Expression", *Anal. Biochem.*, 1988, 172, 289–295.

Markiewicz, W. and Wiewiorowski, "Nucleic Acid Chemistry", Part 3, pp. 229–231, Townsend, L. and Tipson, eds., J. Wiley and Sons, New York, 1986.

Matsukura, M. et al., "Phosphorothioate analogs of oligodeoxynucleotides: Inhibitors of replication and cytopathic effects of human immunodeficiency virus", *PNAS USA*, 1987, 84, 7706–7710.

Meyer, R.B., "Efficient Specific Cross–Linking and Cleavage of DNA by Stable, Synthetic Complementary Oligodeoxynucleotides" *J. Am. Chem. Soc.*, 1989, 111, 8517–8519.

Miller, P.S. and Ts'O, "A New Approach to Chemotherapy Based on Molecular Biology and Nucleic Acid Chemistry: Matagen (Masking Tape for the Gene Expression", *Anti--Cancer Drug Design*, 1987, 2, 117–128.

Miller, P.S. et al., "Nonionic Nucleic Acid Analogues. Synthesis and Characterization of Dideoxyribonucleoside Methylphosphonates", *Biochemistry 1979*, 18, 5134–5143.

Miller, P.S. et al., "Synthesis and Properties of Adenine and Thymine Nucleoside Alkyl Phosphotriesters, the Neutral Analogs of Dinucleoside Monophosphates", *J. Am. Chem. Soc.*, 1971, 93, 6657–6665.

Miller, P.S. et al., "Biochemical and Biological Effects of Nonionic Nucleic Acid Methylphosphonates", *Biochemistry*, 1981, 20, 1874–1880.

Mitsunobu, "The Use of Diethyl Azodicarboxylate and Triphenylphosphine in Synthesis and Transformation of Natural Products", *Synthesis 1981*, 1–28.

Nair V., "Development of Methodologies for the Strategic Modification of Purine Ribonucleoside Systems", *Nucleosides and Nucleotides*, 1989, 8, 699–708.

Ogilvie, K., "Solution and Solid Phase Chemical Synthesis of Arabinonucleotides", *Can. J. Chem.*, 1989, 67, 831–839.

Ogilvie, K., "Prevention of Chain Cleavage in the Chemical Synthesis of 2'–silylated Oligoribonucleotides", *Nucl. Acids. Res.*, 1989, 17, 3501–3517.

Outten, R. and Daves, "Synthetic 1–methoxybenzo[d]naphtho[1,2–b]pyran–6–one c–glycosides", *J. Org. Chem.*, 1987, 52, 5064–5066.

Parkes, K. and Taylor, "A Short Synthesis of 3'–Cyano–3'–Deoxythymidine", *Tetrahedron Letters*, 1988, 29, 2995–2996.

Pfitzner, K.E. and Moffatt J.G., "The synthesis of nucleoside–5'aldehydes", *J. Am. Chem. Soc.*, 1963, 85, 3027.

Ranganathan, R., "Modification of the $2^1$–Position of Purine Nucleosides: Synthesis of $2^1$–a–Substituted–$2^1$–Deoxyadenosine Analogs", *Tetra. Lett.*, 1977, 15, 1291–1294.

Stufkens, D.J., "Dynamic Jahn–Teller Effect in the Excited States of $SeCl^6{}_2-$, $SeBr^6{}_2-$, $TeCl^{6_2}-$ and $TeBr^{6_2}-$", *Rec. Trav. Chim.*, 1970, 89, 1185–1201.

Reese, C. et al., "4'(1,2,4–Triazol–1–yl)–and 4'(3'Nitro'1,2, 4–triazol–1–yl)–1–(β–D–2,3, 5–tri–O–acetylarabinofuranosyl)pyrimidin–2(1H)–ones. Valuable Intermediates in the Synthesis of Derivatives of 1–(β–D–Arabinofuranosyl)cytosine (Ara–C)", *J. Chem. Soc. Perkin Trans I*, 1982, 1171–1176.

Revankar et al., "Synthesis and Antiviral/Antitumor of Certain 3–Seazaguanine Nucleosides and Nucleotides", *Journal of Medicinal Chemistry*, 1984, 27, 1389–1396.

Robins, M. et al, "Nucleic acid related compounds. 46. A general procedure for the efficient deoxygenation of secondary alcohols, regiospecific and stereoselective conversion of ribonucleosides to 2'–deoxynucleosides", *J. Am. Chem. Soc.*, 1983, 105, 4059–4065.

Robins, M., "2'–and 3'–Ketonucleosides and their Arabino and Xylo Reduction Products", *Tetrahedron*, 1984, 40, 125–135.

Roelen, HCPF, et al., "Synthesis of nucleic acid methylphos–phonothioates", *Nucleic Acid Research*, 1988, 16, 7633–7645.

Ruby, S.W. and Abelson, "An early hierarchic role U1 small nuclear ribonucleoprotein in splicesome assembly", *Science*, 1988, 242, 1028–1035.

Schmidt, Richard R. et al., "C–Glycosides from O–Glycosyl Trichloroacetimidates", *Tetrahedron Letters*, 1982, 23, 409–412.

Seela, F. and Kehne, "Palindromic Octa–and Dodencanucleotides Containing 2'–Deoxytubercidin: Synthesis, Hairpin Formation, and Recognition by the Endodeoxyribonuclease EcoRI", *Biochemistry*, 1987, 35, 2233–2238.

Shibahara, S. et al., "Inhibition of Human Immunodeficiency Virus (HIV–1) Replication by Synthetic Oligo–RNA Derivatives", *Nucleic Acids Research*, 1987, 17, 239–252.

Sigman, D., "Nuclease Activity of 1,10–Phenanthroline–Copper Ion", *Accounts of Chemical Research*, 1986, 19, 180–186.

Smith, C. et al., "Anitvivral effect of an oligo(nucleoside methylphosphonate) complementary to the splice junction of herpes simplex virus type 1 immediate early pre–mRNAs 4 and 5", *PNAS USA*, 1986, 83, 2787–2791.

Sproat, B. et al., "Highly Efficient Chemical Synthesis of 2'–O–methyloligoribonucleotides and Tetrabiotinylated Derivatives; Novel Probes that are Resistant to Degradation by RNA or DNA Specific Nucleases", *Nucleic Acids Research*, 1989, 17, 3373–3386.

Sproat, B.S. et al., "New synthetic routes to protected purine 2'–O–methylriboside–3'–O–phosphoramidites using a novel alkylation procedure", *Nucleic Acids Research*, 1990, 18, 41–49.

Stein, C.A. et al., "Physicochemcial properties of phosphorothioate oligodeoxynucleotides", *Nucleic Acids Research*, 1988, 16, 3209–3221.

Stein, C.A. and Cohen, "Oligodeoxynucleotides as Inhibitors of Gene Expression: A Review", *Cancer Research*, 1988, 48, 2659–2668.

Suciu et al., "Synthesis of 9–(2, 5–dideoxy–β–D–glycero–pent–4–enofuranosyl)adenine", *Carbohydr. Res.*, 1975, 44, 112–115.

Bhat, C., "2–Deoxy–3, 5–di–O–p–toluoyl–D–erythro–pentosyl Chloride" in *Synthetic Procedures in Nucleic Acid Chemistry* 1968, vol. 1, Zorbach, ed., Interscience Publ., New York, 521–522.

Tidd, D.M. et al., "Evaluation of N–ras oncogene anti–sense, sense and nonsense sequence methylphosphonate oligonucleotide analogues", *Anti–Cancer Drug Design,* 1988, 3, 117–127.

Van der Krol, A.R. et al., "Modulation of Aukaryotic Gene Expression by Complementary RNA or DNA Sequences", *BioTechniques,* 1988, 6, 958–973.

Walder, R. and Walder, "Role of RNase H in hybrid–arrested translation by antisense oligonucleotides", *PNAS USA,* 1988, 85, 5011–5015.

Walder, J., "Antisense DNA and RNA: Progress and Prospects" *Genes and Development,* 1988, 2, 502–504.

Weissberger, ed., "The Chemistry of Heterocyclic Compounds, Imidazole and Derivatives", Part 1, Interscience, N.Y., 1953.

Yeung, A. et al., "Photoreactives and thermal properties of psoralen cross–links", *Biochem.,* 1988, 27, 3204–3210.

Youssefyeh, R. et al., "Synthetic routes to 4'–hydroxymethl-nucleosides", *Tetra. Lett.,* 1977, 435–438.

Zon, G., "Synthesis of backbone–modified DNA analogues for biological applications", *J. of Protein Chemistry,* 1987, 6, 131–145.

Zon, G., "Oligonucleotide analogues as potential chemotherapeutic agents", *Pharmaceutical Research,* 1988, 5, 539–549.

Agrawal, et al., "Site–specific Excision from RNA by Rnase H and Mixed–Phosphate–Backbone Oligonucletodies", *Proc. Natl. Acad. Sci. USA,* 1990, 87, 1401.

Atherton, et al., *The Peptides,* Gross and Meienhofer, Eds., Academic Press, New York, 1983, vol. 9, pp. 1–38.

Beaucage, "3H–1, 2–Benzodithiole–3–one 1, 1–Dioxide as an Improved Sulfurizing Reagent in the Solid–Phase Synthesis of Oligodeoxyribonucleoside Phosphorothioates", *J. Am. Chem. Soc.,* 1990, vol. 112, 1253–1255.

Breslauer, et al., "The Contribution of DNA Single–Stranded Order to the Thermodynamics of Duplex Formation", *Proc. Natl. Acad. Sci. USA,* 1991, 88, 3569–3573.

Casale, et al., "Synthesis and Properties of an Oligodeoxynucleotide Containing a Polycyclic Aromatic Hydrocarbon Site Specifically Bound to the $N^2$ Amino Group of a 2'–Deoxyguanosine Residue", *J. Am. Chem. Soc.,* 1990, 112, 5264–5271.

Cook, P.D., "Medicinal CHemistry of Antisense Oligonucleotides—Future Opportunities, Anti–Cancer Drug Design", 1991, 6, 585–607.

Antisense Research and Applications, Crooke, S.T. and Lebleu, Eds., CRC Press, Inc., Boca Raton, FL 1993.

Dagle et al., "Pathways of Degradation and Mechanism of Action of Antisense Oligonucleotides in *Xenopus laevis* Embryos", Antisense Research and Developement, 1991, 1, 11–20.

Freier, et al., "Gene Regulation: Biology of Antisense RNA and DNA ", Erickson, et al., Eds., Raven Press, New York, 1992.

Greene and Wuts, Protective Groups in Organic Synthesis, 2nd edition, John Wiley & Sons, New York, 1991.

Harris, et al., "New Strategy for the Synthesis of Oligonucleotides Bearing Adducts at Exocyclic Amino Sites of Purine Nucleosides" *J. Am. Chem. Soc.,* 1991, 113, 4328–4329.

Hoke, et al., "Effects of Phosphorothioate Capping on Antisense Oligonucleotide Stability, Hybridization and Antiviral Efficacy Versus Herpes Simplex Virus Infection", *Nucleic Acids Res.,* 1991, 8, 3746.

Huss, et al., "Synthesis of Various Branched Triribonucleoside Diphosphates by Site–Specific Modification of a Diphenylcarbamoyl–Protected Guanin Residue", Res. Org. Chem. Soc., 1988, 53, 499–506.

Himmelsbach et al., *Tetrahedron,* 1984, 40, 59.

Johnson, et al., "Site–Specific Adduct Formation in Oligomeric DNA Using a New Protecting Group", *J. Am. Chem. Soc.,* 1992, 114, 4923–4924.

Karpyshev, et al., "Phosphite Synthesis of Oligodeoxyribonucleotides," *Russ. Chem. Rev.,* 1988, 57, 1546–1564.

Kawasaki, et al., Uniformly Modified 2'–Deoxy–2'–fluoro Phosphorothioate Oligonucleotides as Nuclease–Resistant Antisense Compounds with High Affinity and Specificity for RNA Targets, *J. Med. Chem.,* 1993, 36, 831–841.

Kern, et al., "9–Beta–D–Ribopyranosylhypoxanthine, a Minor Component Produced by Streptomyces Antibioticus," *J. Heterocyclic Chem.,* 1980, 17, 461.

Lee, et al., Synthesis of Polycyclic Arommatic Hyrdrocarbon–Nucleoside and Oligonucleotide Adducts Specifically Alkylated on the Amino Functions of Deoxyguanosine and Deoxyadenosine, *Tetrahedron Letters,* 1990, 31, 6773–6776.

Lesnik, et al., "Oligodoexynucleotides Containing 2'–O–Modified Adenosine: Synthesis and Effects on Stability of DNA:RNA Duplexes", *Biochemistry,* 1993, 32, 7832–7838.

Markiewicz, et al., "Further studies on oligoribonucleotide synthesis", *Nucleic Acids Res.,* 1980, 7, Symp. Ser. 115–127.

Monia, B.P. et al., "Evaluation of 2'–modified oligonucleotides containing 2' deoxy gaps as antisense inhibitors of gene expression", *J. Biological Chemistry,* 1993, 268, 1–9.

Motawai, et al., "A New Route to 2', 3'–Dideoxycytide", *Liebigs Ann. Chem.,* 1990, 599–602.

Schaller, et al., "Studies on Polynucleotides XXIV. The Stepwise Synthesis of Specific Deoxyribopolynucleotides(4). Protected Derivated of Deoxyribonucleosides and new Eyrthuses of Deoxyribonucleoside–3'Phosphates", *J. Am. Chem. Soc.,* 1963, 85, 3321.

Uhlmann, et al., "Antisense Oligonucleotides: A New Therapeutic Principle", *Chem. Rev.,* 1990, 90, 553–584.

Brady, et al., "Some Novel, Acid–Labile Amine Protecting Groups", *J. Org. Chem.,* 1977, 42, 143–146.

Walder, "Antisense DNA and RNA: Progress and Prospects", *Genes & Developments,* 1988, 2, 502–504.

Veber Hirschmann et al., *J. Org. Chem.,* 1977, 42, 3286.

Castle, R., "Imidazo [4, 5–d] pyridazines. I. Synthesis of 4, 7–Disubstituted Derivatives", Journal of Organic Chemistry, 1958, 23, 1534–1538.

Boryski, J. et al., "A New Simple Synthesis of N–2–Methylguanosine and its Analogues via Derivatives of 4–Desmethylwyosine (Nucleosides and Nucleotides. Part 63 [1])", Nucleosides & Nucleorides, 1985, 4(5), 595–606.

Chemical Abstracts, vol. 56, No. 11, May 28, 1962, abstract No. 12885c, Ballweg, H., "Purine Derivatives of Histamine".

Chemical Abstracts, vol. 102, No. 5, Feb. 4, 1985, abstract No. 041379, Lee, J.H., "Biological Activity of the Products Formed in the Reaction of Natural Compounds with Carbonyls. Part IX. Effect of Oxygen and Metal Ions on the DNA–Breaking Action of Some Guanine Analogs".

Chemical Abstracts, vol. 109, No. 5, Aug. 1, 1988, abstract No. 31488, Ludlum, D.B. et al., "Reaction of Reduced Metronidazole with Guanosine to Form an Unstable Adduct", p. 10, col. 1.

Chemical Abstracts, vol. 86, No. 13, Mar. 28, 1977, abstract No. 89760, Rashid, H., "Chemical Constitution and Cytotoxic Activity. IV. Synthesis of S–Substituted Nitroimidazolyl Derivatives of Purine–6–thiol", p. 539, col. 2.

Chemical Abstracts, vol. 85, No. 3, Jul. 19, 1976, abstract No. 21298, Rashid, H. et al., "Chemical Constitution and Cytostatic Activity. III. Synthesis of 2–Methyl–4–and 5–Nitro–N1–Substituted Imidazolyl Derivatives of 6–Hydroxypurine–2–Thiol and 2, 6–Purinedithiol", p. 687, col. 1.

Chemical Abstracts, vol. 111, No. 1, Jul. 3, 1989, abstract No. 002459, Spratt, T.E. et al., "Analysis for N2–(Pyridyloxoburyl) Deoxyguanosine Adducts in DNA of Tissues Exposed to Tritium Labeled 4–(Methylnirrosamino)–1–(3–Pyridyl)–1–butanone and $N^1$–Nitrosonornicotine".

Chemical Abstracts, vol. 073, No. 9, Aug. 31, 1970, abstract No. 045543, Yamazaki, A et al., "Guanines".

Fourrey, Jean–Louis, et al., "Preparation and Phosphorylation Reactivity of N–Nonacylated Nucleoside", *Terrahedron Letters*, 1985, vol. 26, No. 22, pp. 2663–2666.

Nair, Vasu et al., "Novel Approaches to Funtionalized Nucleosides via Palladium–Catalyzed Cross Coupling with Organostannanes", *J. Am. Chem. Soc.*, 1987, vol. 109, pp. 7223–7224.

Francis, John E., "Highly Selective Adenosine $A_2$ Receptor Agonists in a Series of N–Alkylated 2–Aminoadensines", *J. Med. Chem.*, 1991, vol. 34, pp. 2570–2579.

Freese, Stephen, "$N^2$–Substituted–2'–Deoxyguanosine 5'–Triphosphates as Substrates for E. Coli DNA Polymerase I", *Nucleosides & Nucleorides*, 1991, vol. 10(7), pp. 1507–1524.

Hattori, Masao, et al. "Syntheses and Properties of Poly 2–Alkyladenylic Acids", Nucleic Acids Research, Special Publication vol. 3, 1997, pp. s129–s132.

Hattori, M. et al., "Synthese und Eigenschaften vol Poly–2–Alkyladenylsauren", Nucleorides, VIII, 1978 vol. 11, pp. 1796–1808.

Hecht, Stephen S., Reactions with Deoxyguanosine of 4–(Carbethoxynitrosamino)–1–(3–Pyridyl)–1–Butanone, a Model Compound for aα–Hydroxylation of Tobacco–Specific Nitrosamines[12], *J. Am. Chem. Soc.*, 1986, vol. 108, pp. 1292–1295.

Heeb, Norbert V., "Guanosine Derivatives Bearing an $N^2$–3–Imidazolepropionic Acid", *Terrahedron Letters*, 1994, vol. 35, No. 19, pp. 3045–3048.

Matsuda, Akira, et al., "Nucleosides and Nucleotides. 103. 2–Alkyladenosines: A Novel Class of Selective Adenosine $A_2$ Receptor Agonists with Potent Antihypertensive Effects", *J. Med. Chem.*, 1992, vol. 35, pp. 241–252.

Nair, Vasu, et al., "New Methodologies for the Synthesis of C–2 Functionalized Hypoxanthine Nucleosides", *J. Org. Chem.*, 1988 vol. 53, pp. 3051–3057.

Wang, Guangyi, et al., "Synthesis of Oligonucleorides Containing $N^2$–[2–(imidazol–4–ylacetamido)ethyl]–2'–deoxyguanosine", *Terrahedron Letters*, 1993, vol. 34, No. 42, pp. 6725–6728.

Ramasamy, Kanda S., et al., "Remarkable Enhancement of Binding Affinity of Heterocycle–Modified DNA to DNA and RNA. Synthesis, Characterization and Biophysical Evaluation of $N^2$–Imidazolylpropyguanine and $N^2$–Imidazolylpropylguanine and $N^2$–Imidazolylproply–2–Aminoaderine Modified Oligonucleotides", *Terrahedron Letters*, 1994, vol. 35, No. 2, pp. 215–218.

Wang, Guangyi, et al., "Synthesis of Oligonucleotides Containing $N^2$–(5–Carboxypenryl)–2'–Deoxyguanosine and 5–[2–(4'–Methyl–2, 2'–Dipyrid–4–yl–Carboxamido)Ethylthio]–2'–Deoxyuridine", *Terrahedron Letters*, 1993, vol. 34, No. 42, pp. 6721–6725.

Wong, Corrine G., et al., Inhibitors of Inosinic Acid Dehydrogenase. 2–Substituted Inosinic Acids, *J. Med. Chem.*, 1984 vol. 27, pp. 429–432.

N-2 SUBSTITUTED PURINES

RELATED APPLICATIONS

This application is a continuation of Ser. No. 08/762,587, filed Dec. 10, 1996, now U.S. Pat. No. 5,808,027, which is a division of Ser. No. 08/473,450, filed Jun. 7, 1995, now U.S. Pat. No. 5,587,469, which is a division of Ser. No. 08/159,088, filed Nov. 29, 1993, now U.S. Pat. No. 5,459,255, which is a continuation in part of PCT/US91/00243, filed Jan. 11, 1991, which is a continuation in part of Ser. No. 07/854,634, filed Jul. 1, 1992, now abandoned, which is a continuation in part Ser. No. 07/463,358, filed Jan. 11, 1990, now abandoned, which is a continuation in part of Ser. No. 07/566,977, filed Aug. 13, 1990, now abandoned.

FIELD OF THE INVENTION

This invention relates to novel purine-based compounds that may be incorporated into oligonucleotides. Oligonucleotides are used for a variety of therapeutic and diagnostic purposes, such as treating diseases, regulating gene expression in experimental systems, assaying for RNA and for RNA products through the employment of antisense interactions with such RNA, diagnosing diseases, modulating the production of proteins, and cleaving RNA in site specific fashions. The compounds of the invention include novel heterocyclic bases, nucleosides, and nucleotides. When incorporated into oligonucleotides, the compounds of the invention are useful for modulating the activity of RNA.

BACKGROUND OF THE INVENTION

It is well known that most of the bodily states in mammals including most disease states, are affected by proteins. Such proteins, either acting directly or through their enzymatic functions, contribute in major proportion to many diseases in animals and man. Classical therapeutics has generally focused on interactions with such proteins in efforts to moderate their disease causing or disease potentiating functions. Recently, however, attempts have been made to moderate the actual production of such proteins by interactions with molecules that direct their synthesis, such as intracellular RNA. By interfering with the production of proteins, it has been hoped to affect therapeutic results with maximum effect and minimal side effects. It is the general object of such therapeutic approaches to interfere with or otherwise modulate gene expression leading to undesired protein formation.

One method for inhibiting specific gene expression is the use of oligonucleotides and oligonucleotide analogs as "antisense" agents. The oligonucleotides or oligonucleotide analogs complimentary to a specific, target, messenger RNA (mRNA) sequence are used. Antisense methodology is often directed to the complementary hybridization of relatively short oligonucleotides and oligonucleotide analogs to single-stranded mRNA or single-stranded DNA such that the normal, essential functions of these intracellular nucleic acids are disrupted. Hybridization is the sequence specific hydrogen bonding of oligonucleotides or oligonucleotide analogs to Watson-Crick base pairs of RNA or single-stranded DNA. Such base pairs are said to be complementary to one another. The oligonucleotides and oligonucleotide analogs are intended to inhibit the activity of the selected mRNA—to interfere with translation reactions by which proteins coded by the mRNA are produced—by any of a number of mechanisms. The inhibition of the formation of the specific proteins that are coded for by the mRNA sequences interfered with have been hoped to lead to therapeutic benefits. Cook, P. D. *Anti-Cancer Drug Design* 1991, 6, 585; Cook, P. D. *Medicinal Chemistry Strategies for Antisense Research, in Antisense Research & Applications,* Crooke, et al., CRC Press, Inc.; Boca Raton, Fla., 1993; Uhlmann, et al., A. *Chem. Rev.* 1990, 90, 543.

Oligonucleotides and oligonucleotide analogs are now accepted as therapeutic agents holding great promise for therapeutics and diagnostics methods. But applications of oligonucleotides and oligonucleotide analogs as antisense agents for therapeutic purposes, diagnostic purposes, and research reagents often require that the oligonucleotides or oligonucleotide analogs be synthesized in large quantities, be transported across cell membranes or taken up by cells, appropriately hybridize to targeted RNA or DNA, and subsequently terminate or disrupt nucleic acid function. These critical functions depend on the initial stability of oligonucleotides and oligonucleotide analogs toward nuclease degradation. A serious deficiency of unmodified oligonucleotides for these purposes, particularly antisense therapeutics, is the enzymatic degradation of the administered oligonucleotides by a variety of intracellular and extracellular ubiquitous nucleolytic enzymes, hereinafter referred to as "nucleases."

Initially, only two mechanisms or terminating events have been thought to be operating in the antisense approach to therapeutics. These are the hybridization arrest mechanism and the cleavage of hybridized RNA by the cellular enzyme, ribonuclease H (RNase H). Cook, 1991, supra; Cook, 1993, supra; Uhlmann, supra; Walder, et al., *Proc. Natl. Acad. Sci., USA,* 1988, 85, 5011; Dagle, et al., *Antisense Research & Development,* 1991, 1, 11. It is likely, however, that additional "natural" events may be involved in the disruption of targeted RNA. Many of these naturally occurring events are discussed in *Oligonucleotides: Antisense Inhibitors of Gene Expression,* CRC Press, Inc., Boca Raton, Fla. (Cohen ed., 1989).

Hybridization arrest denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides, Miller, et al., *Anti-Cancer Drug Design,* 1987, 2, 117–128, and α-anomer oligonucleotides are two extensively studied antisense agents that are thought to disrupt nucleic acid function by hybridization arrest.

The second "natural" type of terminating event is the activation of RNase H by the heteroduplex formed between the DNA type oligonucleotides or oligonucleotide analogs and the targeted RNA with subsequent cleavage of target RNA by the enzyme. The oligonucleotides or oligonucleotide analogs, which must be of the deoxyribose type, hybridize with the targeted RNA and this duplex activates the RNase H enzyme to cleave the RNA strand, thus destroying the normal function of the RNA. Phosphorothioate modified oligonucleotides are the most prominent example of antisense agents that are thought to operate by this type of antisense terminating event. Walder, supra and Stein, et al., *Nucleic Acids Research,* 1988, 16, 3209–3221 describe the role that RNase H plays in the antisense approach.

A number of chemical modifications have been introduced into antisense agents—oligonucleotides and oligonucleotide analogs—to increase their therapeutic activity. Such modifications are designed to increase cell penetration of the antisense agents, to stabilize the antisense agents from nucleases and other enzymes that degrade or interfere with their structure or activity in the body, to enhance the antisense agents' binding to targeted RNA, to provide a mode of disruption (terminating event) once the antisense agents are sequence-specifically bound to targeted RNA, and to improve the antisense agents' pharmacokinetic and pharmacodynamic properties. It is unlikely that unmodified, "wild type," oligonucleotides will be useful therapeutic agents because they are rapidly degraded by nucleases. A primary focus of antisense research has been to modify oligonucleotides to render them resistant to such nucleases. These modifications are designed to enhance the uptake of antisense agents—oligonucleotides and oligonucleotide analogs—and thus provide effective therapeutic, research reagent, or diagnostic uses.

To increase the potency via the "natural" termination events, the most often used oligonucleotide modification is modification at the sugar-phosphate backbone, particularly on the phosphorus atom. Phosphorothioates, methyl phosphonates, phosphoramidites, and phosphorotriesters have been reported to have various levels of resistance to nucleases. Backbone modifications are disclosed as set forth in U.S. patent applications assigned to a common assignee hereof, entitled "Backbone Modified Oligonucleotide Analogs," Ser. No. 703,619 and "Heteroatomic Oligonucleotide Linkages," Ser. No. 903,160, the disclosures of which are incorporated herein by reference to disclose more fully such modifications.

An example of phosphate modifications include methyl phosphonate oligonucleotides, where the phosphoryl oxygen of the phosphorodiester linking moiety is replaced with methylene groups or the nucleotide elements together are replaced, either in total or in part, by methyl groups. Other types of modifications to the phosphorus atom of the phosphate backbone of oligonucleotides include phosphorothioate oligonucleotides. The phosphorothioate modified oligodeoxynucleotides are capable of terminating RNA by activation of RNase H upon hybridization to RNA although hybridization arrest of RNA function may play some part in their activity. Phosphoramidites have been disclosed as set forth in U.S. patent application assigned to a common assignee hereof, entitled "Improved Process for Preparation of 2'-O-Alkylguanosines and Related Compounds," Ser. No. 918,362, the disclosures of which are incorporated herein by reference to disclose more fully such modifications. However, all reported modifications of the sugar-phosphate backbone, with the exception of phosphorothioates and phosphorodithioates, obliterate the RNase H terminating event. Cook, 1991, supra; Cook, 1993, supra; Uhlmann, supra. Heteroduplexes formed between RNA and oligodeoxynucleotides bearing 2'-sugar modifications, RNA mimics such as fluoro and alkoxys, do not support RNase H-mediated cleavage. These modified heteroduplexes assume an A form helical geometry as does RNA—RNA heteroduplexes which also do not support RNase H cleavage. Kawasaki, et al., *J. Med. Chem.,* in press 1993; Lesnik, et al., *Biochemistry,* submitted 1993; Inoue, et al., *Nucleic Acids Res.,* 1987, 15, 6131.

Other modifications to "wild type" oligonucleotides made to enhance resistance to nucleases, activate the RNase terminating event, or enhance the RNA-oligonucleotide duplex's hybridization properties include functionalizing the nucleoside's naturally occurring sugar. Sugar modifications are disclosed as set forth in PCT Application assigned to a common assignee hereof, entitled "Compositions and Methods for Detecting and Modulating RNA Activity and Gene Expression," PCT Patent Application Number PCT\US91\00243, International Publication Number WO 91/10671, the disclosures of which are incorporated herein by reference to disclose more fully such modifications.

Other synthetic terminating events, as compared to hybridization arrest and RNase H cleavage, have been studied in an attempt to increase the potency of oligonucleotides and oligonucleotide analogs for use in antisense diagnostics and therapeutics. One area of research is based on the concept that antisense oligonucleotides with modified heterocyclic portions, rather than sugar-phosphate modifications, can be resistant to nucleolytic degradation, yet on hybridization to target RNA provide a heteroduplex that supports RNase H-mediated cleavage. Modifications in the heterocycle portion of oligonucleotides may not affect the heteroduplex helical geometry of sugar that is necessary for RNase H cleavage.

Another approach is directed to the development of sequence-specific chemical RNA cleavers. This concept requires attaching pendent groups with acid/base properties to oligonucleotides. The pendent group is not involved with the specific Watson-Crick hybridization of the oligonucleotides or oligonucleotide analogs with mRNA but is carried along by the oligonucleotide or oligonucleotide analog to serve as a reactive functionality. The pendent group is intended to interact with mRNA in some manner more effectively to inhibit translation of mRNA into protein. Such pendent groups have also been attached to molecules targeted to either single or double stranded DNA. Such pendent groups include, intercalating agents, cross-linkers, alkylating agents, or coordination complexes containing a metal ion with associated ligands.

The sites of attachment of the pendent groups to oligonucleotides and oligonucleotide analogs play an important, yet imperfectly known, part in the effectiveness of oligonucleotides and oligonucleotide analogs for therapeutics and diagnostics.

The half life of the formed RNA-oligonucleotide or oligonucleotide analog duplex may be greatly affected by the positioning of the tethered functional group containing the reactive functionality. Inappropriate positioning of reactive functional groups, such as placement on the Watson-Crick base pair sites, would likely preclude duplex formation. Other attachment sites may potentially allow sequence-specific binding but may be of such low stability that the reactive functionality will not have sufficient time to initiate RNA disruption.

A stable RNA-oligonucleotide or oligonucleotide analog heteroduplex is believed to be important, because without a sufficient half life the reactive or non-reactive functionalities of this invention may not have enough time to initiate the cleavage or otherwise disrupt RNA function. Improved complementation between modified oligonucleotides or oligonucleotides and targeted RNA will likely result in the most stable heteroduplexes.

Targeted RNA is inactivated by formation of covalent links between a modified oligonucleotide and the RNA 2'-hydroxyl group. A variety of structural studies such as X-ray diffraction, chemical reaction, and molecular modeling studies suggests that the 2'-hydroxyl group of RNA in a duplex or heteroduplex resides in the minor groove. The minor side or minor groove of the duplexes formed between such oligonucleotides or modified oligonucleotides and the targeted RNA has been found to be the greatly preferred site for functional group activity.

Prior approaches using cross-linking agents, alkylating agents, and radical generating species as pendent groups on oligonucleotides for antisense diagnostics and therapeutics have had several significant shortcomings. Prior workers have described most pendent groups as being attached to a phosphorus atom which affords oligonucleotides and oligonucleotide analogs with inferior hybridization properties. A phosphorus atom attachment site can allow a reactive group access to both the major and minor grooves. However, internal phosphorus modification results in greatly reduced heteroduplex stability. Attachments at the 3' and/or 5' ends are limiting in that only one or two functional groups can be accommodated in the oligonucleotide compositions.

Other approaches have included attaching reactive functionalities or pendent groups to the 5-position of thymine, and the 7-position of purines. Functionalities placed in the 5-position or 7-position of bases, pyrimidine and purine, respectively, will typically reside in the major groove of the duplex and will not be in proximity to the RNA 2'-hydroxyl substrate. The 2'-hydroxyl is a "trigger" point for RNA inactivation, and thus, any reactive functionalities should be in appropriate proximity to the receptive substrate located in the targeted RNA, especially the most sensitive point, the 2'-hydroxyl group.

Some workers have looked at substitutions at the N-2 position of certain purines, such as hypoxanthine, guanine or adenine. See, e.g., Harris et al., *J. Am. Chem. Soc'y*, 1991, 113, 4328–4329; Johnson et al., *J. Am. Chem. Soc'y*, 1992, 114, 4923–4924; Lee et al., Tetrahedron Letters, 1990, 31, 6773–6776; Casale et al.. *J. Am. Chem. Soc'y*, 1990, 112, 5264–5271.

The functionalities' point of attachment to the base units, which in turn may be converted to modified oligonucleotides, might be considered important in the design of compositions for sequence-specific destruction or modulation of targeted RNA. It is important that the functionalities not interfere with Watson-Crick base pair hydrogen bonding rules, as this is the sequence-specific recognition/binding factor essential for selection of the desired RNA to be disrupted. Further, the functionalities preferably should improve the oligonucleotides compositions' pharmacokinetic and/or pharmacodynamic properties, as well as the oligonucleotide compositions' transport properties across cellular membranes. It is also important that the pendent groups designed to support either enzymatic or chemical cleavage of RNA must be compatible with the requisite hybridization step. When hybridized to RNA, the pendent groups would be accessible, via the minor groove, to the 2'-hydroxyl and phosphorodiester linkages of the targeted RNA.

These aforementioned prior attempts have been relatively insensitive, that is the reactive pendent groups have not been effectively delivered to sites on mRNA molecules for alkylation or cleavage in an effective proportion. Moreover, even if the reactivity of such materials were perfect, (i.e., if each reactive functionality were to actually react with a mRNA molecule), the effect would be no better than stoichiometric. That is, only one mRNA molecule would be inactivated for each oligonucleotide or oligonucleotide analog molecule. It is also likely that the non-specific interactions of oligonucleotide compositions with molecules other then the target RNA, for example with other molecules that may be alkylated or which may react with radical species, as well as self-destruction, not only diminishes the diagnostic or therapeutic effect of the antisense treatment but also leads to undesired toxic reactions in the cell or in vitro. This is especially acute with the radical species that are believed to be able to diffuse beyond the locus of the specific hybridization to cause undesired damage to non-target materials, other cellular molecules, and cellular metabolites. This perceived lack of specificity and stoichiometric limit to the efficacy of such prior alkylating agents and radical generating-types of antisense oligonucleotide compositions is a significant drawback to their employment.

Accordingly, there remains a great need for antisense oligonucleotide compositions that are capable of improved specificity and effectiveness both in binding and modulating mRNA modulation or inactivating mRNA without imposing undesirable side effects. The present invention addresses these, as well as other, needs by presenting novel compounds, based on the purine ring system, that may be used as oligonucleotide intermediates. It has now been found that certain positions on the nucleosides of double stranded nucleic acids are exposed in the minor groove and may be substituted without affecting Watson-Crick base-pairing or duplex stability. Reactive or non-reactive functionalities placed in these positions can best initiate cleavage and destruction of targeted RNA or interfere with its activity.

SUMMARY OF THE INVENTION

This invention presents novel compounds based on the purine ring system that have utility as intermediates for the synthesis of oligonucleotides and oligonucleotide analogs. This invention presents novel, substituted purines comprising a tether portion and at least one reactive or non-reactive functionality. In particular, this invention provides nucleosides, nucleoside analogs, nucleotides, nucleotide analogs, heterocyclic bases, heterocyclic base analogs based on the purine ring system, and oligonucleotide compositions incorporating the same.

The heterocyclic compounds of the invention are adapted for placement of the reactive, RNA cleaving moiety or other reactive moiety into the minor groove site of the hybrid structure formed from the RNA and the compositions of the invention through careful selection of the attachment of the RNA cleaving moieties.

The 2 position of the purine ring has now been found to be a site for attachment of potential RNA cleaving moieties as well as other moieties that may enhance pharmacokinetic properties of antisense without affecting RNase H degradation of target RNA. In addition, a remarkable enhancement of heteroduplex binding affinity is observed when certain pendent groups are attached to the 2 position of the novel purine based compounds of the invention. These pendent groups protrude into the minor groove of a DNA-RNA heteroduplex and do not affect binding affinities.

In one aspect of the invention, the compounds have the formula:

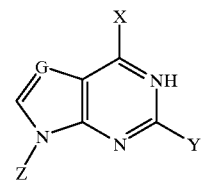

wherein
G is C or N;
X is NH₂ or OH;
Y is RQ or NHRQ, wherein R is a hydrocarbyl group having from 2 to about 20 carbon atoms; and Q is at least one reactive or nonreactive functionality; and
Z is H, a nitrogen protecting group, or a sugar moiety.

The invention further provides compounds comprising a sugar and base moiety as discussed above, with the 3' position of the sugar moiety derivatized with a phosphate group. The sugar moiety of the nucleosidic units for incorporation into oligonucleotides compositions may be ribose, deoxyribose, or a sugar analog. Preferably the sugar is ribose or deoxyribose. The groups linking the heterocyclic bases or modified bases together may be the usual sugar phosphate nucleic acid backbone found in nature, but may also be modified as a phosphorothioate, methyl-phosphonate, or phosphate alkylated moiety to further enhance the modified oligonucleotides' properties. Other backbone modifications may also be employed such as the removal of 5'-methylene group, and the use of alkyl, or heteroatomic sugar.

In another aspect of this invention, mixed sequence oligonucleotides incorporating at least one of the compounds as set forth herein are presented.

DETAILED DESCRIPTION OF PREFERRED EMBODIMENTS

This invention presents novel heterocyclic compounds based on the purine ring system that may be used as intermediates for oligonucleotide compositions. This invention provides nucleosides, nucleoside analogs, nucleotides, nucleotide analogs, heterocyclic bases, heterocyclic base analogs, and oligonucleotide compositions incorporating the same.

The novel compounds of the invention are based on the purine ring system, comprising a heterocyclic purine-base portion, at least one reactive or non-reactive functionality, and a tether portion for attaching the functionalities to the balance of the compound. The 2 position of the purine ring has been found to be a unique point of attachment for reactive and non-reactive functionalities. Attachment at this position enhances the oligonucleotides and oligonuceltides analogs' ability to modulate RNA activity without interfering with stability of an RNA-oligonucleotide heteroduplex, and also improves the oligonucleotides' transport properties. The non-reactive functionalities' utility lies, in part, in their ability to improve the pharmacodynamic or pharmacokinetic properties of the oligonucleotide compositions, whether or not these functionalities may also play a role in initiating cleaving reactions. These attributes and others make these compounds useful intermediates for incorporation into oligonucleotide compositions.

The functional sites on the base units are important in the design of compositions for sequence-specific destruction or modulation of targeted RNA. The half-life of the formed duplex is believed to be greatly effected by the positioning of the tethered group that connects the reactive functionality to the base unit. Inappropriate positioning of functional groups, such as placement on the Watson-Crick base pair sites, would preclude duplex formation. It is important that the tether functionality not interfere with Watson-Crick base pair hydrogen bonding rules as this is the sequence-specific recognition/binding factor for selection of the desired RNA to be disrupted.

Attachment sites, other than the 2 position of the purine ring, may allow sequence-specific binding but may be of such low stability that the reactive functionality will not have sufficient time to initiate RNA disruption. It has now been found that certain positions on the nucleosides of double stranded nucleic acids are exposed in the minor groove and may be substituted without affecting Watson-Crick base-pairing or duplex stability. Reactive or non-reactive functionalities placed in these positions in accordance with this invention can best initiate cleavage and destruction of targeted RNA or interfere with its activity. The sites of functionality in the heterocyclic compounds of the invention are novel—the 2 position of the purine ring system—and have been preferably designed such that the functionalities will preferably reside in or on the minor groove formed by the heteroduplex between modified oligonucleotides and targeted RNA.

The compounds of the invention may have at least one reactive functionality or other moiety appended thereto capable of interacting with, preferably cleaving, an RNA. These moieties are preferably adapted for placement of the reactive or other moiety into the minor groove site of the hybrid structure formed from the RNA and oligonucleotides and oligonucleotide analogs including the compositions of the invention.

It is not necessary to tether more than one, two, or a relatively small number of RNA cleaving functionalities to oligonucleotide compositions in accordance with this invention to provide the benefits of the invention. An RNA cleaving moiety will preferably be tethered to a relatively small proportion of the subunits, generally only one or two of the oligonucleotide compositions of the invention. In other embodiments of the invention, however, substantially all of the nucleotides in an oligonucleotide can be modified to include one or more functionalities such as RNA cleaving moieties.

The compounds of the invention may be used to prepare desired oligonucleotides and oligonucleotide analogs; these oligonucleotides and oligonucleotide analogs are also within the ambit of this invention.

Incorporation of the novel compounds of the invention into oligonucleotide compositions improves those compositions' pharmacokinetic and pharmacodynamic properties, the compositions' resistance to nucleases, facilitates antisense and non-antisense therapeutic uses, diagnostic uses, and research reagent uses, improves the compositions' binding capabilities without any concomitant interference with the Watson-Crick binding, and enhances the compositions' penetration into cells. Some of these enhanced properties are illustrated in Table 1 below.

In the context of this invention, a "nucleoside" is a nitrogenous heterocyclic base linked to a pentose sugar, either a ribose, deoxyribose, or derivatives or analogs thereof. The term "nucleotide" means a phosphoric acid ester of a nucleoside comprising a nitrogenous heterocyclic base, a pentose sugar, and one or more phosphate or other backbone forming groups; it is the monomeric unit of an oligonucleotide. The term "oligonucleotide" refers to a plurality of joined nucleotide units formed in a specific sequence from naturally occurring heterocyclic bases and pentofuranosyl equivalent groups joined through phosphorodiester or other backbone forming groups. Nucleotide units may include the common bases such as guanine, adenine, cytosine, thymine, or derivatives thereof. The pentose sugar may be deoxyribose, ribose, or groups that substitute therefore. The terms "antisense agents" and "oligonucleotide compositions" as used in the context of this invention encompass oligonucleotides and oligonucleotide analogs and are interchangeable. In the context of this invention, phosphate derivatives include phosphorothioates, methyl phosphonates, phosphoramidites, phosphorotriesters, and any other groups known to those skilled in the art.

"Modified base," "base analog," "modified nucleoside," "nucleotide analog," or "modified nucleotide," in the context of this invention refer to moieties that function similarly to their naturally occurring counterparts but have been functionalized to change their properties.

"Sugar moiety," as used in the context of this invention, refers to naturally occurring sugars, such as ribose or deoxyribose, and sugars and non-sugar analogs that have been functionalized to change certain properties.

"Oligonucleotide analogs" or "modified oligonucleotides," as used in connection with this invention, refer to compositions that function similarly to natural oligonucleotides but have non-naturally occurring portions. Oligonucleotide analogs or modified oligonucleotides may have altered sugar moieties, altered bases, both altered sugars and bases or altered inter-sugar linkages, for example phosphorothioates and other sulfur containing species which are known for use in the art.

In the context of the invention, "improved pharmacodynamic property" means improved oligonucleotide uptake, enhanced oligonucleotide resistance to degradation, and/or strengthened sequence-specific hybridization with RNA. "Improved pharmacokinetic property" means improved oligonucleotide uptake, distribution, metabolism, or excretion.

The "hydrocarbyl" groups disclosed and claimed herein are the linkers or tethers that attach reactive or non-reactive functionalities to the purine based compounds of the invention. "Hydrocarbyl compounds," as used herein, means straight, branched, or cyclic carbon and hydrogen containing compounds. In the context of this invention, a straight chain compound means an open chain compound, such as an aliphatic compound, including alkyl, alkenyl, or alkynyl compounds. A branched compound, as used herein, comprises a straight chain compound, such as an alkyl, alkenyl, alkynyl, which has further straight chains attached to the carbon atoms of the straight chain. In the context of this invention, the terms "lower alkyl," "lower alkenyl," or "lower alkynl" means compounds, straight or branched, having between about 1 to about 10 carbon atoms. A "cyclic compound," as used herein, refers to closed chain compounds—is, a ring of carbon atoms, such as a cyclic aliphatic or aromatic compound. The straight, branched, or cyclic compounds may be internally interrupted. In the context of this invention, internally interrupted means that the carbon chains may be interrupted with heteroatoms such as O, N, or S. If desired, the carbon chain may have no heteroatoms present. The hydrocarbyl compounds noted above may be substituted or unsubstituted. In the context of this invention, "substituted" or "unsubstituted," means that the hydrocarbyl compounds may have any one of a variety of substituents, in replacement, for example, of one or more hydrogen atoms in the compound, or may have no substituents. Suitable substituents will be readily apparent to one skilled in the art once armed with the present disclosure.

Pendent groups as used herein refers to both reactive and non-reactive functionalities. "Reactive functionality," as used herein, means a moiety that interacts with mRNA in some manner to more effectively inhibit translation of the mRNA into protein. For example, such a moiety may act as an RNA cleaving agent. A "non-reactive functionality," as used herein, means a functional group that may not possess a reactive portion or may not initiate chemical reactions, but rather enhances the oligonucleotide compositions' pharmacodynamic and pharmacokinetic properties, whether or not it plays any role in RNA cleavage. When terminal end is used in reference to the reactive or non-reactive functionality, this term means the end not attached to the purine core.

In one preferred aspect of the invention, the compound has the following formula:

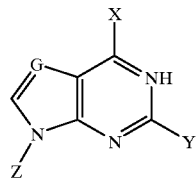

wherein
G is C or N;
X is $NH_2$ or OH;
Y is RQ or NHRQ, wherein said R is H or a hydrocarbyl group having from 2 to about 20 carbon atoms; and Q comprises at least one reactive or non-reactive functionality; and
Z is H, a nitrogen protecting group, or a sugar moiety.

In certain preferred embodiments, Q is a nitrogen-containing heterocycle. In other preferred embodiments, Q is a substituted or unsubstituted imidazole. In other more preferred embodiments, Y is RQ and said Q is an imidazole. In still other preferred embodiments, Y is NHRQ and Q is an imidazole.

In certain other preferred embodiments, G is N; X is $NH_2$; Y is NHRQ, said R is a lower alkane and Q is an imidazole. In a more preferred embodiment, R is an alkane having between about 2 to about 4 carbon atoms, preferably propyl.

In other preferred embodiments, G is N; X is OH; Y is NHRQ, said R is a lower alkane; and Q is an imidazole. In more preferred embodiments, R is an alkane having between about 2 to about 4 carbon atoms, preferably ethyl or isobutyryl, more preferably propyl. In other preferred embodiments, R is isobutyryl and Q is a methyl-imidazole.

In still other preferred embodiments, G is N; X is $NH_2$; Y is NHRQ, said R is H and Q is an alkane having from about 5 up to about 20 carbon atoms, preferably between about 5 to about 10 carbon atoms.

In still other preferred embodiments, G is N; X is $OH_2$; Y is NHRQ, said R is H and Q is an alkane having from about 5 up to about 20 carbon atoms, preferably between about 5 to about 10 carbon atoms.

In other certain preferred embodiments, Y is RQ, said R is a lower alkane; and Q is an amine, wherein said amine comprises $NH_2$, polyalkylamines, aminoalkylamines, hydrazines (—NH—NH—), hydroxylamines (—NH—OH), semicarbazides (—NH—C(O)—NH—$NH_2$), thiosemicarbazides (—NH—C(S)—NH—$NH_2$), hydrazones (—N=NH), or hydrazides (—C(O)—$NHNH_2$); and Z is ribose or deoxyribose, preferably deoxyribose.

In other preferred embodiments, Y is NHRQ, said R is a lower alkane; and Q is an amine, wherein said amine comprises $NH_2$, polyalkylamines, aminoalkylamines, hydrazines (—NH—NH—), hydroxylamines (—NH—OH), semicarbazides (—NH—C(O)—NH—$NH_2$), thiosemicarbazides (—NH—C(S)—NH—$NH_2$), hydrazones (—N=NH), or hydrazides (—C(O)—$NHNH_2$); and Z is ribose or deoxyribose.

In a more preferred embodiment, G is N; X is $NH_2$; Y is NHRQ, said R is a lower alkane; and Q is an amine, wherein said amine comprises $NH_2$, polyalkylamines, aminoalkylamines, hydrazines (—NH—NH—), hydroxylamines (—NH—OH), semicarbazides (—NH—C(O)—NH—$NH_2$), thiosemicarbazides (—NH—C(S)—NH—$NH_2$), hydrazones (—N=NH), or hydrazides (—C(O)—$NHNH_2$), especially $NH_2$.

In another preferred embodiment, G is N; X is OH; Y is NHRQ, said R is a lower alkane; and Q is an amine, wherein said amine comprises $NH_2$, polyalkylamines, aminoalkylamines, hydrazines (—NH—NH—), hydroxylamines (—NH—OH), semicarbazides (—NH—C(O)—NH—$NH_2$), thiosemicarbazides (—NH—C(S)—NH—$NH_2$), hydrazones (—N=NH), or hydrazides (—C(O)—$NHNH_2$), especially $NH_2$. In a more preferred embodiment, G is N; X is OH; Y is NHRQ, said R is hexane and Q is $NH_2$.

In certain other preferred embodiments, Y is NHRQ, and the reactive functionality, Q, is a thiol group, aldehyde, ketone, alcohol, or an alkoxy group. In other preferred embodiments, Y is RQ and the reactive functionality Q is a thiol group, aldehyde, ketone, alcohol, or an alkoxy group.

The hydrocarbyl groups (R) may serve as tethers or linkers for attaching reactive or non-reactive functionalities to the purine ring system of the compounds of the invention. The hydrocarbyl groups, R, suitable for practicing this invention may be alkyl, alkenyl, aryl, or cyclic groups. Alkyl groups of the invention include, but are not limited to, straight and branched chained alkyls such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methyl-pentyl, 3-methylpentyl, 2-ethylhexyl, 2-propylpentyl. While propyl groups have been found to be highly useful R groups, other alkyl groups, including methyl, ethyl, butyl, and others up to about octyl, can find utility; preferred are $C_2$ to $C_4$ alkyl with propyl being most preferred. Ethylene, propylene, and other glycols and polyamines are also useful.

Alkenyl groups useful in the invention include, but are not limited to, unsaturated moieties derived from the above alkyl groups including but not limited to vinyl, allyl, crotyl, propargyl.

Useful aryl groups include, but are not limited to, phenyl, tolyl, benzyl, naphthyl, anthracyl, phenanthryl, and xylyl.

Any of the hydrocarbyl groups, that is, the straight, branched, or cyclic alkyl, alkenyl, or alkynyl groups pointed out above may be internally interrupted with heteroatoms, such as O, N, or S; however, this is not required. For example, polyoxyhydrocarbyl or polyaminohydrocarbyl compounds are fully contemplated within the ambit of the invention. Some further examples include those where R may comprise a polyhydric alcohol, such as —$CH_2$—$(CHOH)_n$—$CH_2OH$, wherein n=1 to 5. Alternatively, by way of example, R may comprise an ether, such as —$CH_2$ $(CHOH)_nCH_2O(CH_2)_m$, where n=1 to 10 and m=1 to 10.

The hydrocarbyl groups may be further substituted. Substituent groups for the above include, but are not limited to, other alkyl, haloalkyl, alkenyl, alkoxy, thioalkoxy, haloalkoxy and aryl groups as well as halogen, hydroxyl, amino, azido, carboxy, cyano, nitro, mercapto, sulfides, sulfones, sulfoxides, and heterocycles. Other suitable substituent groups will be apparent to those skilled in the art and may be used without departing from the spirit of the invention.

Reactive functionalities suitable for use as Q in the practice of this invention include, but are not limited to, halogens; substituted or unsubstituted heterocyclic compounds, such as substituted or unsubstituted heterocycloalkyls; amino containing groups, such as heterocycloalkylaminos, polyalkylaminos, imidazoles, imadiazole amides, alkylimidazoles; substituted or unsubstituted aldehydes; substituted or unsubstituted ketones; substituted or unsubstituted ethers; substituted or unsubstituted esters; substituted or unsubstituted aryl compounds having from about 6 to about 20 carbon atoms, such as aralkylamino having from about 6 to about 20 carbon atoms, aminoaralkylamino having from about 6 to about 20 carbon atoms, alkyloxyaryl compounds, or allyloxyaryl compounds.

The amine functionalities can be primary amines, hydrazines (—NH—NH—), hydroxylamines (—NH—OH), semicarbazides (—NH—C(O)—NH—$NH_2$), thiosemicarbazides (—NH—C(S)—NH—$NH_2$), hydrazones (—N=NH), or hydrazides (—C(O)—$NHNH_2$), or similar nitrogenous species. Amines of this invention are also meant to include polyalkylamino compounds and aminoalkylamines such as aminopropylamines and further heterocycloalkylamines, such as imidazol-1, 2, or 4-ylpropylamine.

Polyamides, polyesters, and polyethylene glycols according to the invention have structures analogous to the above-described polyamines, except that an amide, ester or alcohol functionality is substituted for the nitrogenous species of the polyamine. Polyether groups have also analogous structures, except that one or more ether oxygen atoms are interspersed in the carbon chains.

The following compounds for forming compounds with amine-functionalized linker or tether groups are commercially available from Aldrich Chemical Co., Inc., Milwaukee, Wis.: N-(2-bromoethyl)phthalimide, N-(3-bromopropyl)phthalimide and N-(4-bromobutyl) phthalimide. Other phthalimide-protected amine compounds can be conveniently synthesized from appropriate alkyl, aralkyl or aryl halides and phthalimide. Representative compounds include N-(7-bromoheptyl) phthalimide; N-(8-bromooctyl)phthalimide; N-(9-bromononyl) phthalimide; N-(10-bromododecyl)phthalimide; N-(11-bromoundecyl) phthalimide; N-(12-bromodocecyl)phthalimide; N-(13-bromotridecyl) phthal-imide; N-(14-bromotetradecyl) phthalimide; N-(15-bromopentadecyl) phthalimide; N-(16-bromohexadecyl)-phthalimide; N-(17-bromoheptadecyl) phthalimide; N-(18-bromooctadecyl) phthalimide; N-(19-bromononadecyl)phthalimide; N-(3-bromo-2-methylpropyl) phthalimide; N-(4-bromo-2-methyl-3-ethylbutyl) phthalimide; N-(3-bromo-2,2-diethylpropyl) phthalimide; N-(4-bromo-3-propylbutyl)phthalimide; N-(10-bromo-2,8-dibutyl-decyl) phthalimide; N-(8-bromo-6,6-dimethyloctyl)phthalimide; N-(8-bromo-6-propyl-6-butyloctyl)phthalimide; N-(4-bromo-2-methyl-butyl) phthalimide; N-(5-bromo-2-methylpentyl) phthalimide; N-(5-bromo-3-methylpentyl)phthalimide; N-(6-bromo-2-ethylhexyl)phthalimide; N-(5-bromo-3-penten-2-one) phthalimide; N-(4-bromo-3-methyl-2-butanol)phthalimide; N-(8-bromo-3-amino-4-chloro-2-cyano-octyl)phthalimide; N-(7-bromo-3-methoxy-4-heptanal)phthalimide; N-(4-bromo-2-iodo-3-nitrobutyl) phthalimide; N-(12-bromo-4-isopropoxydodecyl) phthalimide; N-(10-bromo-4-azido-2-nitrodecyl)phthalimide; N-(9-bromo-5-mercaptononyl) phthal-imide; N-(5-bromo-4-amino-pentenyl) phthalimide; N-(5-bromo-penten-2-yl)phthalimide; N-(3-bromoallyl) phthalimide; N-(4-bromocrotyl)phthalimide; N-(3-bromopropargyl)phthalimide; N-(1-bromonaphth-4-yl) phthalimide; N-(2-bromoanthrac-7-yl)- phthalimide; and N-(2-bromophenanthr-6-yl)phthalimide. Such halide compounds are then reacted with an appropriate 2 amino or other 2-substituted purine.

Suitable heterocyclic groups include, but are not limited to, imidazole, tetrazole, triazole, pyrrolidine, piperidine, piperazine and morpholine. Amines include amines of all of the above alkyl, alkenyl and aryl groups including primary and secondary amines and "masked amines" such as phthalimide. Other reactive functionalities suitable for practicing the invention include, without limitation, compounds having thiol (SH), aldehyde (C=O), or alcohol (OH) functionalities.

These reactive functionalities are capable of catalyzing, alkylating, or otherwise effecting the cleavage, destruction or disablement of RNA, especially of its phosphorodiester bonds. The reactive functionalities may either be basic, acidic, or amphoteric. Heteroatomic species can be formulated to be either basic or acidic or, indeed, to be amphoteric for such purposes. Alkylating and free radical forming functionalities may also be used for these purposes.

Non-reactive functionalities for Q, include, but are not limited to, alkyl chains, polyamines, ethylene glycols, polyamides, aminoalkyl chains, amphipathic moieties, points for reporter group attachment, and intercalators attached to any of the preferred sites for attachment.

The reactive and non-reactive functionalities may be further substituted. Suitable substituents include, but are not limited to, other hydrocarbyl compounds, halohydrocarbyl compounds, alkoxy, thioalkoxy, haloalkoxy, or aryl groups, as well as halogen, hydroxyl, amino, azido, carboxy, cyano, nitro, mercapto, sulfides, sulfones and sulfoxides. Any of the straight, branched, or cyclic hydrocarbyl substituents may be further internally interrupted with O, N, or S. Substituent groups can be present on the above-described alkyl, alkenyl, alkyne, polyamine, polyamide, polyester, polyethylene glycol, polyether, aryl, aralkyl and heterocyclic space-spanning groups. Substituent groups include but are not limited to halogen, hydroxyl, keto, carboxy, nitrates, nitrites, nitro, nitroso, nitrile, trifluoromethyl, O-alkyl, S-alkyl, NH-alkyl, amino, azido, sulfoxide, sulfone, sulfide, silyl, intercalators, conjugates, polyamines, polyamides, polyethylene glycols, polyethers, groups that enhance the pharmacodynamic properties of oligonucleotides and groups that enhance the pharmacokinetic properties of oligonucleotides. Typical intercalators and conjugates include cholesterols, phospholipids, biotin, phenanthroline, phenazine, phenanthridine, anthraquinone, acridine, fluoresceins, rhodamines, coumarins, and dyes. Halogens include fluorine, chlorine, bromine, and iodine. Other suitable substituent groups will be apparent to those skilled in the art and may be used without departing from the spirit of the invention.

The invention further provides compounds comprising a sugar combined with a base moiety as discussed above. Suitable sugar moieties include, but are not limited to, ribose, deoxyribose, and sugar analogs.

In certain preferred embodiments, Z is ribose or deoxyribose. In a more preferred embodiment, Z is deoxyribose. In another preferred embodiment, Z is a sugar analog, preferably similar to the deoxyribose type.

In other preferred embodiments, G is N; X is OH; Y is NHRQ, said R is a lower alkane; and Q is an imidazole; and Z is ribose or deoxyribose, preferably deoxyribose. In more preferred embodiments, R is an alkane having between about 2 to about 4 carbon atoms, preferably ethyl or isobutyryl, more preferably propyl; and Z is ribose or deoxyribose, preferably deoxyribose. In other preferred embodiments, R is isobutyryl and Q is a methyl-imidazole; and Z is ribose or deoxyribose, preferably deoxyribose.

In still other preferred embodiments, G is N; X is $NH_2$; Y is NHRQ, said R is H and Q is an alkane having from about 5 up to about 20 carbon atoms, preferably between about 5 to about 10 carbon atoms; and Z is ribose or deoxyribose, preferably deoxyribose.

In other certain preferred embodiments, Y is RQ, said R is a lower alkane; and Q is an amine, wherein said amine comprises $NH_2$, polyalkylamines, aminoalkylamines, hydrazines (—NH—NH—), hydroxylamines (—NH—OH), semicarbazides (—NH—C(O)—NH—$NH_2$), thiosemicarbazides (—NH—C(S)—NH—$NH_2$), hydrazones (—N=NH), or hydrazides (—C(O)—NH—$NH_2$); and Z is ribose or deoxyribose, preferably deoxyribose.

In other preferred embodiments, Y is NHRQ, said R is a lower alkane; and Q is an amine, wherein said amine comprises $NH_2$, polyalkylamines, aminoalkylamines, hydrazines (—NH—NH—), hydroxylamines (—NH—OH), semicarbazides (—NH—C(O)—NH—$NH_2$), thiosemicarbazides (—NH—C(S)—NH—$NH_2$), hydrazones (—N=NH), or hydrazides (—C(O)—NH—$NH_2$); and Z is ribose or deoxyribose.

In a more preferred embodiment, G is N; X is $NH_2$; Y is NHRQ, said R is a lower alkane; and Q is an amine, wherein said amine comprises $NH_2$, polyalkylamines, aminoalkylamines, hydrazines (—NH—NH—), hydroxylamines (—NH—OH), semicarbazides (—NH—C(O)—NH—$NH_2$), thiosemicarbazides (—NH—C(S)—NH—$NH_2$), hydrazones (—N=NH), or hydrazides (—C(O)—NH—$NH_2$), especially $NH_2$; and Z is ribose or deoxyribose, preferably deoxyribose.

In another preferred embodiemtn, G is N; X is OH; Y is NHRQ, said R is a lower alkane; and Q is an amine, wherein said amine comprises $NH_2$, polyalkylaminos, aminoalkylamines, hydrazines (—NH—NH—), hydroxylamines (—NH—OH), semicarbazides (—NH—C(O)—NH—$NH_2$), thiosemicarbazides (—NH—C(S)—NH—$NH_2$), hydrazones (—N=NH), or hydrazides, especially $NH_2$; and Z is ribose or deoxyribose, preferably deoxyribose. In a more preferred embodiemtn, G is N; X is OH; Y is NHRQ, said R is hexane and Q is $NH_2$; and Z is ribose or deoxyribose, preferably deoxyribose.

In certain other preferred embodiments, Y is NHRQ, and the reactive functionality, Q, is a thiol group, aldehyde, ketone, alcohol, or an alkoxy group; and Z is ribose or deoxyribose, preferably deoxyribose. In other preferred embodiments, Y is RQ and the reactive functionality Q is a thiol group, aldehyde, ketone, alcohol, or an alkoxy group; and Z is ribose or deoxyribose, preferably deoxyribose.

Generally, sugar moieties may be attached to the novel purine based compounds of the invention using methods known in the art. See Revankar, supra.

Substituted sugars may be synthesized according to the methods disclosed in PCT Patent Application Number PCT\US91\00243 assigned to a common assignee hereof, entitled "Compositions and Methods for Detecting and Modulating RNA Activity and Gene Expression," the disclosures of which are incorporated herein by reference to disclose more fully such modifications.

For example, a substituted sugar as, methyl 3-O-(t-butyldiphenylsilyl)-2,5-dideoxy-5-C-formyl-α/β-D-erythro-pentofuranoside, can be prepared by modifying 2-deoxy-D-ribose to methyl 2-deoxy-a/β-D-erythro-pentofuranoside (prepared according to the method of Motawai et al., *Liebigs Ann. Chem.*, 1990, 599–602), which on selective tosylation followed by 3-O-silylation gave methyl 3-O-(t-butyldimethylsilyl)-2-deoxy-5-O-tosyl-α/β-D-erythro-pentofuranoside.

As will be appreciated by persons of ordinary skill in the art, variations in the structures of the sugar moieties useful in the preparation of the subject compositions may be made without deviating from the spirit of the invention. Suitable substituents on the sugar moiety include, but are not limited to, OH, lower alkyl, substituted lower alkyl, aralkyl, heteroalkyl, heterocycloalkyl, aminoalkylamino, heterocycloalkyl, polyalkylamino, substituted silyl, F, Cl, Br, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH_2$, $OCH_2CCH$, OCCHO, or an RNA cleaving moiety. It is not necessary that every sugar linking function be in a modified form because a substantial number and even a predominance of the linking groups may exist in the native, phosphorodiester form as long as the overall targeting portion of the compositions of the invention exhibit an effective ability to penetrate into the intracellular spaces of cells of the organism in question or otherwise to contact the target RNA and to specifically bind therewith to form a hybrid capable of detecting and modulating RNA activity. Of course, fully unmodified, native phosphorodiester structure may also be used for those purposes.

In other preferred embodiments, Z will be a nitrogen protecting group. Generally, protecting groups are known per se as chemical functional groups that can be selectively appended to and removed from functionalities, such as amine groups. These groups are present in a chemical compound to render such functionality inert to chemical reaction conditions to which the compound is exposed. See, e.g., Greene, et al., Protective Groups in Organic Synthesis, (John Wiley & Sons, New York, 2d ed. 1991). Numerous amine protecting groups are known in the art, including, but not limited to, the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. (see, e.g., Veber Hirschmann, et al., *J. Org. Chem.* 1977, 42, 3286 and Atherton, et al., (Academic Press, New York, Gross & Meinhofer, eds, 1983). For example, it is known that the Boc group can protect an amine group from base and from reducing conditions but that it can be removed with acid. Other nitrogen protecting groups will be apparent to those skilled in the art and may be used without detracting from the spirit of the invention. Any ester protecting groups known to those skilled in the art may be used; tetrahydropyranyl is an example of such a group. See Greene, supra.

The invention further provides compositions comprising a sugar and base moiety as discussed above, with the 3' position of the sugar moiety derivatized with a phosphate group. Generally, nucleotides of the invention may be prepared by protecting the 5' position of the sugar moiety of the imidazole ring and derivatizing the 3' position with an appropriate phosphoramidite or other phosphate suitable for use on a DNA synthesizer, including without limitation, alkyl phosphonates, phosphorothioates, or phosphorotriesters.

Generally, the compounds of the invention may be synthesized under the following reaction conditions. The following reaction describes attachment of the 3-(1H-imidazol-1-yl)propyl moiety to the 2-amino group of deoxyguanosine and 2-aminodeoxyadenosine, and subsequent incorporation of these novel nucleosides into oligonucleotides. The numbers enclosed in the parentheses refer to the compounds on the reaction scheme depicted below in the Examples section.

2-Chloro-9-(2-deoxy-β-D-erythropentofuranosyl)inosine (3), a versatile, key intermediate, was obtained by heating 2,6-dichloro-9-(2-deoxy-b-D-erythropentofuranosyl)purine (1), Kazimierczuk et al., *J. Am. Chem. Soc.* 1984, 106, 6379, with sodium hydride (NaH) in allyl alcohol, followed by hydrogenation of the intermediate (2) with Pd/C at atmospheric pressure. For similar procedure see Kern et al., *Heterocyclic Chem.,* 1980, 17, 461. Displacement of the 2-chloro atom of (3) with 1-(3-aminopropyl)imidazole gave (4). The isobutyryl derivative of (4), Lesnik, supra, was subjected to the Mitsunobu reaction condition, Himmelsbach et al., *Tetrahedron,* 1984, 40, 59, in the presence of 2-(p-nitrophenyl) ethanol to provide fully protected nucleoside (6). Selective removal of the isobutyryl groups in (6), followed by dimethoxy-tritylation, Schaller et al., *Am. Chem. Soc.,* 1963, 85, 3821 and phosphitylation, Karpyshev et al., *Russ. Chem. Rev.,* 1988, 57, 886 afforded the deoxyguanosine amidite synthon (8) in 73% yield.

2-Chloro-deoxyadenosine (9) Christensen, et al., *J. Med. Chem.* 1972, 15, 735 was treated with 1-(3-aminopropyl)imidazole to provide $N^2$-substituted 2-aminodeoxyadenosine (10) which was protected by sequential treatment with TipSiCl, Markiewicz, et al., *Nucleic. Acid Res., Symp. Ser.* 1980, 7, 115 and isobutyrylchloride (IbCl) to afford (12). Removal of the TipSi protecting group of (12) with Bu$_4$NF, Huss et al., *Org. Chem. Soc.,* 1988, 53, 499 and subsequent dimethoxytritylation and phosphitylation provided the deoxyadenosine amidite synthon (14).

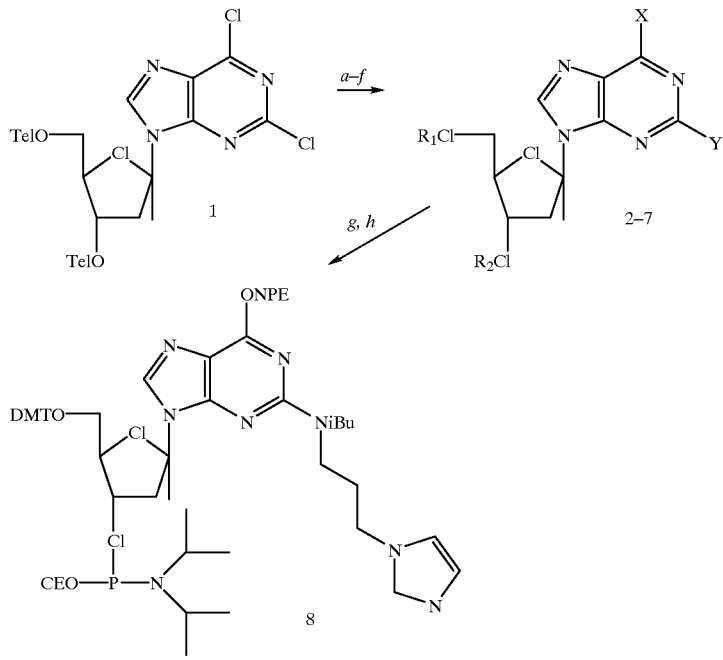

-continued

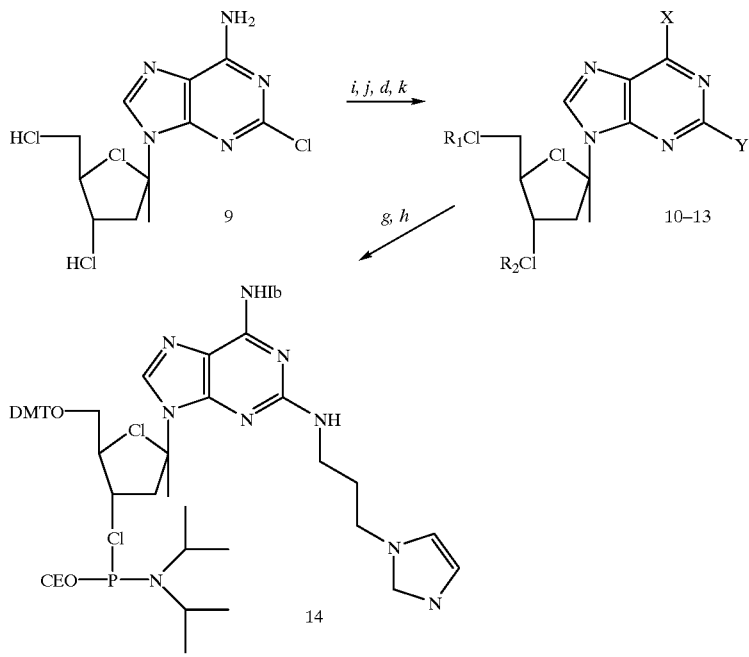

1. 2,6-Dichloro-9-(2'-deoxy-β-D-erythro-pentofuranosyl) purine.
2. $R_1$ and $R_2$=H; X=Allyloxy; Y=Cl.
3. $R_1$ and $R_2$=H; X=OH; Y=Cl.
4. $R_1$ and $R_2$=H; X=OH; Y=NH(CH$_2$)$_3$Im.
5. $R_1$ and $R_2$=Ib; X=OH; Y=IbN(CH$_2$)$_3$Im.
6. $R_1$ and $R_2$=Isobutyryl; X=ONPE; Y=IbN(CH$_2$)$_3$Im.
7. $R_1$ and $R_2$=H; X=ONPE; Y=IbN(CH$_2$)$_3$Im.
8. Deoxyguanosine amidite synthon.
9. 2-Chloro-deoxyadenosine.
10. $R_1$ and $R_2$=H; X=NH$_2$; Y=NH(CH$_2$)$_3$—Im.
11. $R_1$ and $R_2$=TipSi; X=NH$_2$; Y=NH(CH$_2$)$_3$—IM.
12. $R_1$ and $R_2$=H; X=NHIb; Y=NH(CH$_2$)$_3$—Im.
13. $R_1$ and $R_2$=OH; X=NHIb; Y=NH(CH$_2$)$_3$—Im.
Ib=Isobutyryl
Im=Imidazole
NPE=(Nitrophenyl)ethanol
Reaction Conditions:
(a) NaH/Allyl alcohol; (b) Pd/C/H/EtOH; (c) 1-(3-Aminopropyl) imidazole/2-ethoxyethanol (90° C.); (d) IbCl/TEA/PY; (e) 2-(p-nitrophenyl)ethanol/Ph$_3$P/DEAD/Dioxane; (f) NH$_4$OH/CH$_3$OH; (g) DMTCl/TEA/PY; (h) 2-Cyanoethyl N,N-diisopropylchlorophosphoramidite/N,N-diisopropylethylamine/CH$_2$Cl$_2$; (i) 1-(3-Aminopropyl) imidazole/2-Methoxyethanol (125° C.); (j) TipSiCl/TEA/PY; and (k) Bu$_4$NF/THF.

In another aspect of the invention, oligonucleotides or oligonucleotide analogs incorporating the novel compounds of the invention are provided. Generally, the oligonucleotides or oligonucleotide analogs may comprise a sugar modified or native oligonucleotide containing a target sequence that is specifically hybridizable with a preselected nucleotide sequence, a sequence of DNA or RNA that is involved in the production of proteins whose synthesis is ultimately to be modulated or inhibited in its entirety.

In certain preferred embodiments, the oligonucleotides of the invention comprise:
 a first oligonucleotide region and a second nucleotide region;
 together said first and said second region of a nucleotide sequence essentially complementary to at least a portion of said RNA;
 said first region including at least one nucleotide having a base unit as defined above in connection with the heterocyclic compounds of the invention; and said second region including a plurality of consecutive phosphorothiocite linked nucleotides having a 2'-deoxy-erythro-pentofuranosyl sugar moiety. In certain preferred embodiments, the sugar moiety is ribose or deoxyribose and said phosphate is a methylphosphonate, phosphorothioate, phosphoramidite, phosphorotriester. In other preferred embodiments, the oligonucleotides of the invention further comprise a third region that includes at least one nucleotide having a base unit as defined above in connection with the heterocyclic compounds of the invention; wherein said second region is positioned in said oligonucleotide between said first and third regions.

Incorporation of amidites (i.e., 8 and 14 in the reaction scheme outlines depicted below in connection with the synthesis of the heterocycles of the invention) into oligonucleotide sequences can be accomplished via automated DNA synthesis protocol. (Standard protocol using an ABI 380B DNA synthesizer was modified by increasing the wait step after the pulse delivery of tetrazole to 900 seconds. Deprotection conditions are discussed in Himmelsbach, et al., *Tetrahedron*, 1984, 40, 59).

Generally, oligonucleotides or oligonucleotide analogs incorporating the novel compounds of the invention may be synthesized, conveniently through solid state synthesis of known methodology, to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide or oligonucleotide analog of reasonable length which may be desired.

The resulting novel oligonucleotides or oligonucleotide analogs are synthesized by the standard solid phase, automated nucleic acid synthesizer such as the Applied Biosystems, Incorporated 380B or MilliGen/Biosearch 7500 or 8800. Triester, phosphoramidite, or hydrogen phosphonate coupling chemistries, *Oligonucleotides Antisense Inhibitors, supra,* pp. 7–24, are used in with these synthesizers to provide the desired oligonucleotides or oligonucleotide analogs. The Beaucage reagent, *J. Am. Chem. Society,* 1990, 112, 1253–1255 or elemental sulfur, Beaucage et al., *Tetrahedron Letters,* 1981, 22, 1859–1862, is used with phosphoramidite or hydrogen phosphonate chemistries to provide substituted phosphorothioate oligonucleotides. These oligonucleotide compositions comprise a targeting portion specifically hybridizable with a preselected nucleotide sequence of RNA, some of the phosphodiester bonds may be substituted with a structure that functions to enhance the compositions' ability to penetrate into cells' intracellular region where the RNA, whose activity is to be modulated, is located. Standard backbone modifications include, but are not limited to, phosphorothioates, methyl phosphonates, phosphoramidites, and phosphorotriesters. These substitutions are thought in some cases to enhance the sugar modified oligonucleotides' properties. These phosphate bond modifications are disclosed as set forth in U.S. Patent Applications assigned to a common assignee hereof, entitled "Backbone Modified Oligonucleotide Analogs," Ser. No. 07/703,169 and "Heteroatomic Oligonucleotide Linkages," Ser. No. 07/903,160, the disclosures of which are incorporated herein by reference to disclose more fully such modifications. Backbone modifications may be used without departing from the spirit of the invention. It is not necessary, however, that the compounds of the invention have modified phosphate backbones.

Modifications that may provide oligonucleotides or oligonucleotide analogs that are substantially less ionic than native forms and facilitate penetration of modified or unmodified oligonucleotides into the intracellular spaces are also contemplated by this invention. Any of the existing or yet to be discovered methods for accomplishing this goal may be employed in accordance with the practice of the present invention. As will be appreciated by those skilled in the art, modifications of the phosphate bond find utility in this regard. Variations in the phosphate backbone useful in the preparation of the subject compositions may be made without deviating from the spirit of the invention. Modifications at the phosphorous atom are set forth in an U.S. Pat. No. 5,138,048, entitled "Polyamine Oligonucleotides to Enhance Cellular Uptake," and assigned to a common assignee hereof.

Although the invention is primarily directed to substitutions at the N-2 position of a purine base or heterocycle, other positions for attachment of reactive and non-reactive functionalities having a similar effect may be found, especially when further modifications of the purine structure are undertaken as may be done by persons of ordinary skill in the art without deviating from the spirit of the present invention. Once again, it is to be understood that preferably one, or at most a few RNA cleaving moieties are generally to be employed. Thus, artisans in the field will have great latitude in selecting means for attaching the RNA cleaving moieties, the pharmacodynamic improving groups, or the pharmacokinetic improving groups in accordance with this invention.

The present invention is further described in the following examples. These examples are for illustrative purposes only, and are not to be construed as limiting the appended claims.

EXAMPLES

Examples 1–45 are depicted in synthetic Scheme 1, which immeadiately follows Example 45. Examples 46–53 are depicted in synthetic Scheme 2, which immeadiately follows Example 53. Examples 54–56 are depicted in synthetic Scheme 3, which immeadiately follows Example 56. The numbers in parantheses following the Example's title compound correspond to the compound numbers on the respective schemes.

Example 1

2,6-Dichloro-9-(2-deoxy-3,5-di-O-p-toluoyl-β-D-erythro-pentofuranosyl)purine. (1)

To a stirred solution of 2,6-dichloropurine (25.0 g, 132.27 mmol) in dry acetonitrile (1000 mL) was added sodium hydride (60% in oil, 5.40 g, 135 mmol) in small portions over a period of 30 minutes under argon atmosphere. After the addition of NaH, the reaction mixture was allowed to stir at room temperature for 30 minutes. Predried and powdered 1-chloro-2-deoxy-3,5,di-O-p-toluoyl-δ-D-erythro-pentofuranose (53.0 g, 136 mmol) was added during a 15 minute period and the stirring continued for 10 hours at room temperature over argon atmosphere. The reaction mixture was evaporated to dryness and the residue dissolved in a mixture of $CH_2Cl_2/H_2O$ (250:100 mL) and extracted in dichloromethane (2×250 mL). The organic extract was washed with brine (100 mL), dried, and evaporated to dryness. The residue was dissolved in dichloromethane (300 mL), mixed with silica gel (60–100 mesh, 250 g) and evaporated to dryness. The dry silica gel was placed on top of a silica gel column (250–400 mesh, 12×60 cm) packed in hexane. The column was eluted with hexanes (1000 mL), toluene (2000 mL), and toluene:ethyl acetate (9:1, 3000 mL). The fractions having the required product were pooled together and evaporated to give 52 g (72%) of 3 as white solid. A small amount of solid was crystallized from ethanol for analytical purposes. mp 160–162° C.; $^1$H NMR (DMSO-$d_6$); δ 2.36 (s, 3H, $CH_3$), 2.38 (s, 3H, $CH_3$), 2.85 (m, 1H, $C_2'H$), 3.25 (m, 1H, $C_2'H$), 4.52 (m, 1H, $C_4H$), 4.62 (m, 2H, $C_5CH_2$), 5.80 (m, 1H, $C_3'H$), 6.55 (t, 1H, $J_{1',2'}$=6.20 Hz, $C_1'H$), 7.22 (dd, 2H, ArH), 7.35 (dd, 2H, ArH), 7.72 (dd, 2H, ArH), 7.92 (dd, 2H, ArH), and 8.92 (s, 1H, $C_8H$).

Example 2

2-Chloro-6-allyloxy-9-(2'-deoxy-β-D-erythro-pentofuranosyl)purine. (2)

To a stirred suspension of 2,6-dichloro-9-(2'-deoxy-3',5'-di-O-p-toluoyl-β-D-erythro-pentofuranosyl)-purine (1, 10.3 g, 19.04 mmol) in allyl alcohol (150 mL) was added sodium hydride (60%, 0.8 g, 20.00 mmol) in small portions over a 10 minute period at room temperature. After the addition of NaH, the reaction mixture was placed in a preheated oil bath at 55° C. The reaction mixture was stirred at 55° C. for 20 minutes with exclusion of moisture. The reaction mixture was cooled, filtered, and washed with allyl alcohol (50 mL). To the filtrate IRC-50 (weakly acidic) $H^+$ resin was added until the pH of the solution reached 4–5. The resin was filtered, washed with methanol (100 mL), and the filtrate was evaporated to dryness. The residue was absorbed on silica gel (10 g, 60–100 mesh) and evaporated to dryness. The dried silica gel was placed on top of a silica column (5×25 cm, 100–250 mesh) packed in dichloromethane. The column was then eluted with $CH_2Cl_2$/acetone (1:1). The fractions having the product were pooled together and evaporated to dryness to give 6 g (96%) of the title compound as foam. $^1$H NMR ($Me_2SO$-$d_6$) δ 2.34 (m, 1H, $C_2'H$), 2.68 (m, 1H, $C_2'H$), 3.52 (m, 2H, $C_5'H$), 3.86 (m, 1H, $C_4'H$), 4.40 (m, 1H, $C_3'H$), 4.95 (t, 1H, $C_5'OH$), 5.08 (d, 2H, $CH_2$), 5.35 (m, 3H, $CH_2$ and $C_3'OH$), 6.10 (m, 1H, CH), 6.35 (t, 1H, $J_{1',2'}$=6.20 Hz, $C_1'H$), 8.64 (s, 1H, $C_8H$). Anal. Calcd for $C_{13}H_{15}ClN_4O_4$: C, 47.78; H, 4.63; N, 17.15; Cl, 10.86. Found: C, 47.58; H, 4.53; N, 17.21; Cl, 10.91.

Example 3
2-Chloro-9-(2'-deoxy-β-D-erythro-pentofuranosyl)inosine. (3)

A mixture of 2 (6 g, 18.4 mmol), Pd/C (10%, 1 g) and triethylamine (1.92 g, 19.00 mmol) in ethyl alcohol (200 mL) was hydrogenated at atmospheric pressure during 30 minute periods at room temperature. The reaction mixture was followed by the absorption of volume of hydrogen. The reaction mixture was filtered, washed with methanol (50 mL), and the filtrate evaporated to dryness. The product 5.26 g (100%) was found to be moisture sensitive and remained as a viscous oil. The oil was used as such for further reaction without purification. A small portion of the oil was dissolved in water and lyophilized to give an amorphous solid: $^1$H NMR (Me$_2$SO-d$_6$) δ 2.35 (m, 1H, C$_2$H), 2.52 (m, 1H, C$_2$H), 3.54 (m, 2H, C$_5$H), 3.82 (m, 1H, C$_4$H), 4.35 (m, 1H, C$_3$H), 4.92 (b s, 1H, C$_5$OH), 5.35 (s, 1H, C$_3$OH), 6.23 (t, 1H, J$_{1',2'}$=6.20 Hz, C$_1$H), 8.32 (s, 1H, C$_8$H), 13.36 (b s, 1H, NH).

Example 4
N$_2$-[Imidazol-1-yl(propyl)]-9-(2'-deoxy-β-D-erythro-pentofuranosyl)guanosine. (4)

A solution of the nucleoside of 3 (10.3 g, 36.00 mmol) and 1-(3-aminopropyl)imidazole (9.0 g, 72.00 mmol) in 2-methoxyethanol (60 mL) was heated in a steel bomb at 100° C. (oil bath) for 24 hours. The bomb was cooled to 0° C., opened carefully and the precipitated solid was filtered. The solid was washed with methanol (50 mL), acetone (50 mL), and dried over sodium hydroxide to give 9 g (67%) of pure 4. A small amount was recrystallized from DMF for analytical purposes: mp 245–47° C.: $^1$H NMR (Me$_2$SO-d$_6$) δ 1.94 (m, 2H, CH$_2$), 2.20 (m, 1H, C$_2$H), 2.54 (m, 1H, C$_2$H), 3.22 (m, 2H, CH$_2$), 3.51 (m, 2H, C$_5$H), 3.80 (m, 1H, C$_4$H), 3.98 (m, 2H, CH$_2$), 4.34 (m, 1H, C$_3$H), 4.90 (b s, 1H, C$_5$OH), 5.51 (s, 1H, C$_3$OH), 6.12 (t, 1H, J$_{1',2'}$=6.20 Hz, C$_1$H), 6.46 (b s, 1H, NH), 6.91 (s, 1H, ImH), 7.18 (s, 1H, ImH), 7.66 (s, 1H, ImH), 7.91 (s, 1H, C$_8$H), 10.60 (b s, 1H, NH). Anal. Calcd for C$_{16}$H$_{21}$N$_7$O$_4$: C, 51.19; H, 5.64; N, 26.12. Found: C, 50.93; H, 5.47; N, 26.13.

Example 5
3',5'-Di-O-isobutyryl-N$_2$-[imidazol-1-yl(propyl)]-N$_2$-isobutyryl-9-(2'-deoxy-β-D-erythro-pentofuranosyl)guanosine. (5)

To a well dried solution of the substrate of 4 (1.5 g, 4.00 mmol) and triethylamine (1.62 g, 16.00 mmol) in dry pyridine (30 mL) and dry DMF (30 mL) was added isobutyryl chloride (1.69 g, 16.00 mmol) at room temperature. The reaction mixture was allowed to stir at room temperature for 12 hours and evaporated to dryness. The residue was partitioned between dichloromethane (100 mL) and water (50 mL) and extracted with CH$_2$Cl$_2$ (2×200 mL). The organic extract was washed with brine (100 mL) and dried over anhydrous MgSO$_4$. The dried organic extract was evaporated to dryness and the residue was purified over flash chromatography using CH$_2$Cl$_2$/MeOH as eluent. The pure fractions were pooled, evaporated to dryness which on crystallization from CH$_2$Cl$_2$/MeOH gave 1.8 g (77%) of 5 as a colorless crystalline solid: mp 210–212° C.; $^1$H NMR (Me$_2$SO-d$_6$) δ 1.04 (m, 18H, 3 Isobutyryl CH$_3$), 1.94 (m, 2H, CH$_2$), 2.56 (m, 4H, C$_2$'H and 3 Isobutyryl CH) 2.98 (m, 1H, C$_2$'H), 3.68 (m, 2H, CH$_2$), 3.98 (m, 2H, CH$_2$), 4.21 (2 m, 3H, C$_5$H and C$_4$H), 5.39 (m, 1H, C$_3$H), 6.30 (t, 1H, J$_{1',2'}$=6.20 Hz, C$_1$H), 6.84 (s, 1H, ImH), 7.18 (s, 1H, ImH), 7.34 (s, 1H, ImH), 8.34 (s, 1H, C$_8$H), 10.60 (b s, 1H, NH). Anal. Calcd for C$_{28}$H$_{39}$N$_7$O: C, 57.42; H, 6.71; N, 16.74. Found: C, 57.29; H, 6.58; N, 16.56.

Example 6
6-0-[2-(4-Nitrophenyl)ethyl]-N$_2$-3',5'-tri-O-isobutyryl-N$_2$-[imidazol-1-yl(propyl)]-9-(2'-deoxy-β-D-erythro-pentofuranosyl)guanosine. (6)

To a stirred solution of 5 (2.0 g, 3.42 mmol), triphenylphosphine (2.68 g, 10.26 mmol) and p-nitrophenyl ethanol (1.72 g, 10.26 mmol) in dry dioxane was added diethylazodicarboxylate (1.78 g, 10.26 mmol) at room temperature. The reaction mixture was stirred at room temperature for 12 hours and evaporated to dryness. The residue was purified by flash chromatography over silica gel using CH$_2$Cl$_2$/acetone as the eluent. The pure fractions were pooled together and evaporated to dryness to give 2.4 g (96%) of the title compound as an amorphous solid. $^1$H NMR (Me$_2$SO-d$_6$) δ 1.04 (m, 18H, 3 Isobutyryl CH$_3$), 1.94 (m, 2H, CH$_2$), 2.50 (m, 3H, C$_2$H and 2 Isobutyryl CH), 3.00 (m, 1H, C$_2$H), 3.12 (m, 1H, Isobutyryl CH), 3.24 (m, 2H, CH$_2$), 3.82 (m, 2H, CH$_2$), 3.98 (m, 2H, CH$_2$), 4.21 (2 m, 3H, C$_5$CH$_2$ and C$_4$H), 4.74 (m, 2H, CH$_2$), 5.39 (m, 1H, C$_3$H), 6.34 (t, 1H, J$_{1',2'}$=6.20 Hz, C$_1$H), 6.82 (s, 1H, ImH), 7.08 (s, 1H, ImH), 7.56 (s, 1H, ImH), 7.62 (d, 2H, ArH), 8.1 (d, 2H, ArH), 8.52 (s, 1H, C$_8$H). Anal. Calcd for C$_{36}$H$_{46}$N$_8$O$_9$—½H$_2$O: C, 58.13; H, 6.37; N, 15.01. Found: C, 58.33; H, 6.39; N, 14.75.

Example 7
6-0-[2-(4-Nitrophenyl)-ethyl]-N$_2$-isobutyryl-N$_2$-[imidazol-1-yl-(propyl)]-9-(2'-deoxy-β-D-erythro-pentofuranosyl)guanosine. (7)

To a stirred solution of 6 (9.00 g, 12.26 mmol) in methanol (250 ml) was treated with ammonium hydroxide (30%, 150 ml) at room temperature. The reaction mixture was stirred at room temperature for 4 hours and evaporated to dryness under reduced pressure. The residue was purified by flash chromatography over silica gel using CH$_2$Cl$_2$/MeOH as the eluent. The pure fractions were pooled together and evaporated to dryness to give 5.92 g (81%) of the title compound: $^1$H NMR (Me$_2$SO-d$_6$) δ 1.04 (m, 6H, Isobutyryl CH$_3$), 1.96 (m, 2H, CH$_2$), 2.32 (m, 1H, C$_2$H), 2.62 (m, 1H, C$_2$H), 3.14 (m, 1H, Isobutyryl CH), 3.26 (m, 2H, CH$_2$), 3.52 (m, 2H, C$_5$CH$_2$), 3.82 (m, 3H, CH$_2$ and C$_4$H), 3.96 (m, 2H, CH$_2$), 4.36 (m, 1H, C$_3$H), 4.70 (m, 2H, CH$_2$), 4.96 (b s, 1H, C$_5$OH), 5.42 (b s, 1H, C$_3$OH), 6.34 (t, 1H, J$_{1',2'}$=6.20 Hz, C$_1$H), 6.82 (s, 1H, ImH), 7.12 (s, 1H, ImH), 7.54 (s, 1H, ImH), 7.62 (d, 2H, ArH), 8.16 (d, 2H, ArH), 8.56 (s, 1H, C$_8$H). Anal. Calcd for C$_{28}$H$_{34}$N$_8$O$_7$—½H$_2$O: C, 55.71; H, 5.84; N, 18.56. Found: C, 55.74; H, 5.67; N, 18.43.

Example 8
5'-0-(4,4'-Dimethoxytrityl)-6-0-[2-(4-nitrophenyl)ethyl]-N$_2$-isobutyryl-N$_2$-[imidazol-1-yl(propyl)]-2'-deoxy-β-D-erythro-pentofuranosyl)guanosine. (8)

The substrate 7 (5.94 g, 10 mmol), was dissolved in dry pyridine (75 mL) and evaporated to dryness. This was repeated three times to remove traces of moisture. To this well dried solution of the substrate in dry pyridine (100 mL) was added dry triethylamine (4.04 g, 40 mmol), 4-(dimethylamino)pyridine (1.2 g, 30 mmol) at room temperature. The reaction mixture was stirred at room temperature for 12 hours under argon atmosphere. Methanol (50 mL) was added and the stirring was continued for 15 minutes and evaporated to dryness. The residue was purified by flash chromatography over silica gel using dichloromethane-acetone containing 1% triethylamine as the eluent. The pure fractions were pooled together and evaporated to dryness to give 7.2 g (80%) of the title compound as a colorless foam: $^1$H NMR (Me$_2$SO-d$_6$) δ 1.04 (m, 6H, Isobutyryl CH$_3$), 1.94 (m, 2H, CH$_2$), 2.34 (m, 1H, C$_2$H), 2.80 (m, 1H, C$_2$H), 3.04 (m, 1H, Isobutyryl CH), 3.18 (m, 2H, CH$_2$), 3.28 (m, 2H, CH$_2$), 3.62 (s, 3H, OCH$_3$), 3.66 (s, 3H, OCH$_3$), 3.74 (2 m, 2H, C$_5$CH$_2$), 3.98 (m, 3H, CH$_2$ and C$_4$H), 4.36 (m, 1H, C$_3$H), 4.70 (m, 2H, CH$_2$), 5.44 (b s, 1H, C$_3$OH), 6.32 (t, 1H, J$_{1',2'}$=6.20 Hz C$_1$H), 6.64–7.32 (m, 15H, ImH and ArH), 7.52 (s, 1H, ImH), 7.62 (d, 2H, ArH), 8.16 (d, 2H, ArH), 8.42 (s, 1H, C$_8$H). Anal. Calcd for C$_{49}$H$_{52}$N$_8$O$_9$—H$_2$O: C, 64.32; H, 5.95; N, 12.25. Found: C, 64.23; H, 5.82; N, 12.60.

Example 9

3'-0-(N,N-Diisopropylamino) (β-cyanoethoxy)phosphanyl]-5'-0-(4,4'-dimethoxytrityl)-6-0-[2-(4-nitrophenyl)ethyl]-N$_2$-isobutyryl-N$_2$-[imidazol-1-yl(propyl)]-9-(2'-deoxy-β-D-erythro-pentofuranosyl)guanosine. (9)

The substrate of 8 (2.5 g, 2.7 mmol), was dissolved in dry pyridine (30 mL) and evaporated to dryness. This was repeated three times to remove last traces of water and dried over solid sodium hydroxide overnight. The dried 8 was dissolved in dry dichloromethane (30 mL) and cooled to 0° C. under argon atmosphere. To this cold stirred solution was added N,N-diisopropylethylamine (0.72 g, 5.6 mmol) followed by (β-cyanoethoxy)chloro(N,N-diisopropylamino) phosphate (1.32 g, 5.6 mmol) dropwise over a period of 15 minutes. The reaction mixture was stirred at 0° C. for 1 hour and at room temperature for 2 hours. The reaction mixture was diluted with dichloromethane (100 mL) and washed with brine (50 mL). The organic extract was dried over anhydrous MgSO$_4$ and the solvent was removed under reduced pressure. The residue was purified by flash chromatography over silica gel using hexane/acetone containing 1% triethylamine as the eluent. The main fractions were collected and evaporated to dryness. The residue was dissolved in dry dichloromethane (10 mL) and added dropwise, into a stirred solution of hexane (1500 mL), during 30 minutes. After the addition, the stirring was continued for an additional 1 hour at room temperature under argon. The precipitated solid was filtered, washed with hexane and dried over solid NaOH under vacuum overnight to give 2.0 g (65%) of the title compound as a colorless powder: $^1$H NMR (Me$_2$SO-d$_6$) δ 1.04 (2 m, 18H, 3 Isobutyryl CH$_3$), 1.94 (m, 2H, CH$_2$), 2.44 (m 3H, C$_2$H and 2 Isobutyryl CH), 2.80 (m, 1H, C$_2$H), 3.2 (m, 5H, 2 CH$_2$ and Isobutyryl CH), 3.44–3.98 (m, 12H, CH$_2$, 2OCH$_3$ and C$_5$CH$_2$), 4.16 (m, 1H, C$_4$H), 4.64 (m, 3H, C$_3$H and CH$_2$), 6.32 (t, 1H, J$_{1',2'}$=6.20 Hz, C$_1$H), 6.64–7.32 (m, 16H, 3ImH and ArH), 7.44 (d, 2H, ArH), 8.16 (d, 3H, ArH and C$_8$H).

Example 10

N$_2$-[Imidazol-1-yl(propyl)]-9-(2'-deoxy-β-D-erythro-pentofuranosyl)adenosine. (11)

A suspension of 2-chloro-9-(2'-deoxy-β-D-erythro-pentofuranosyl)adenosine (10, 10.68 g, 37.47 mmol) and 1-(3 aminopropyl) imidazole (12.5 g, 100 mmol) in 2-methoxyethanol (80 mL) was heated at 125° C. for 45 hours in a steel bomb. The bomb was cooled to 0° C., opened carefully, and evaporated to dryness. The residue was coevaporated several times with a mixture of ethanol and toluene. The residue was dissolved in ethanol which on cooling gave a precipitate. The precipitate was filtered and dried. The filtrate was evaporated to dryness and the residue carried over to the next reaction without further purification. $^1$H NMR (Me$_2$SO-d$_6$) δ 1.94 (m, 2H, CH$_2$), 2.18 (m, 1H, C$_2$H), 2.36 (m, 1H, C$_2$H), 3.18 (m, 2H, CH$_2$), 3.52 (2 m, 2H, C$_5$CH$_2$), 3.80 (m, 1H, C$_4$H), 4.02 (m, 2H, CH$_2$), 4.36 (m, 1H, C$_3$H), 5.24 (b s, 2H, C$_3$OH and C$_5$OH), 6.18 (t, 1H, J$_{1',2'}$=6.20 Hz, C$_1$H), 6.42 (t, 1H, NH), 6.70 (b s, 2H NH$_2$), 6.96 (s, 1H, ImH), 7.24 (s, 1H, ImH), 7.78 (s, 1H, ImH), 7.90 (s, 1H, C$_8$H). Anal. Calcd for C$_{16}$H$_{22}$N$_8$O$_3$: C, 51.33; H, 5.92; N, 29.93. Found: C, 51.30; H, 5.92; N, 29.91.

Example 11

3',5'-O-[(Tetraisopropyldisiloxane-1,3-diyl)-N$_2$-(imidazol-1-yl)(propyl)]-9-(2'-deoxy-β-D-erythro-pentofuranosyl) aminoadenosine. (12)

The crude product 11 (14.03 g) was dissolved in dry DMF (100 mL) dry pyridine (50 mL), and evaporated to dryness. This was repeated three times to remove all the water. The dried substrate was dissolved in dry DMF (75 mL) and allowed to stir at room temperature under argon atmosphere. To this stirred solution was added dry triethylamine (10.1 g, 100 mmol) and 1,3-dichloro-1,1, 3,3-tetraisopropyldisiloxane (TipSiCl, 15.75 g, 50.00 mmol) during a 15 minute period. After the addition of TipSiCl, the reaction mixture was allowed to stir at room temperature overnight. The reaction mixture was evaporated to dryness. The residue was mixed with toluene (100 mL) and evaporated again. The residue was purified by flash chromatography over silica gel using CH$_2$Cl$_2$/MeOH as eluent. The pure fractions were pooled and evaporated to dryness to give 12.5 g (54%) of 12 as an amorphous powder: $^1$H NMR (Me$_2$SO-d$_6$) δ 1.00 (m, 28H), 1.92 (m, 2H, CH$_2$), 2.42 (m, 1H, C$_2$H), 2.80 (m, 1H, C$_2$H), 3.18 (m, 2H, CH$_2$), 3.84 (2 m, 3H, C$_5$CH$_2$ and C$_4$H), 4.00 (t, 2H, CH$_2$), 4.72 (m, 1H, C$_3$H), 6.10 (m, 1H, C$_1$H), 6.48 (t, 1H, NH), 6.74 (b s, 2H, NH$_2$), 6.88 (s, 1H, ImH), 7.18 (s, 1H, ImH), 7.64 (s, 1H, ImH), 7.82 (s, 1H, C$_8$H). Anal. Calcd for C$_{28}$H$_{50}$N$_8$O$_4$Si$_2$: C, 54.33; H, 8.14; N, 18.11. Found: C, 54.29; H, 8.09; N, 18.23.

Example 12

3',5'-O-(Tetraisopropyldisiloxane-1,3-diyl)-N$_6$-isobutyryl-N$_2$-[(imidazol-1-yl)propyl]-9-(2'-deoxy-β-D-erythro-pentofuranosyl)adenosine. (13)

A solution of 12 (12.0 g, 19.42 mmol) in pyridine (100 mL) was allowed to stir at room temperature with triethylamine (10.1 g, 100 mmol) under argon atmosphere. To this stirred solution was added isobutyryl chloride (6.26 g, 60 mmol) dropwise during a 25 minute period. The reaction mixture was stirred under argon for 10 hours and evaporated to dryness. The residue was partitioned between dichloromethane/water and extracted with dichloromethane (2×150 mL). The organic extract was washed with brine (30 mL) and dried over anhydrous MgSO$_4$. The solvent was removed under reduced pressure and the residue was purified by flash chromatography over silica gel using CH$_2$Cl$_2$/acetone as the eluent to give the 13 as a foam: $^1$H NMR (Me$_2$SO-d$_6$) δ 1.00 (m, 34H), 1.92 (m, 2H, CH$_2$), 2.42 (m, 1H, C$_2$H), 2.92 (m, 2H, C$_2$H and Isobutyryl CH), 3.24 (m, 2H, CH$_2$), 3.86 (m, 3H, C$_5$CH$_2$ and C$_4$H), 4.40 (m, 2H, CH$_2$), 4.74 (m, 1H, C$_3$H), 6.22 (m, 1H, J$_{1',2'}$=6.20 Hz, C$_1$H), 6.82 (t, 1H, NH), 6.92 (s, 1 H, ImH), 7.18 (s, 1H, ImH), 7.60 (s, 1H, ImH), 8.12 (s, 1H, C$_8$H), 10.04 (b s, 1H, NH). Anal. Calcd for C$_{32}$H$_{54}$N$_8$O$_5$Si$_2$: C, 55.94; H, 7.92; N, 16.31. Found: C, 55.89; H, 7.82; N, 16.23.

Example 13

3',5'-Di-O-isobutyryl-N$_2$-[imidazol-1-yl(propyl)]-N$_6$-isobutyryl-9-(2'deoxy-β-D-erythro-pentofuranosyl) adenosine. (14)

The crude product 11 (9.2 g, 24.59 mmol) was coevaporated three times with dry DMF/pyridine (100:50 mL). The above dried residue was dissolved in dry DMF (100 mL) and dry pyridine (100 mL) and cooled to 0° C. To this cold stirred solution was added triethylamine (20.2 g, 200 mmol) followed by isobutyryl chloride (15.9 g, 150 mmol). After the addition of IbCl, the reaction mixture was allowed to stir at room temperature for 12 hours. The reaction mixture was evaporated to dryness. The residue was extracted with dichloromethane (2×200 mL), washed with 5% NaHCO$_3$ (50 mL) solution, water (50 mL), and brine (50 mL). The organic extract was dried over dry MgSO$_4$ and the solvent was removed under reduced pressure. The residue was purified by flash column using CH$_2$Cl$_2$/acetone (7:3) as the eluent. The pure fractions were collected together and evaporated to give 7.0 g (44%) of 14 as a foam: $^1$H NMR (Me$_2$SO-d$_6$) δ 1.00 (m, 18H, 3 Isobutyryl CH$_3$), 1.98 (m, 2H, CH$_2$), 2.42 (m, 3H, C$_2$H and 2 Isobutyryl CH), 2.92 (m, 2H, C$_2$H and Isobutyryl CH), 3.24 (m, 2H, CH$_2$), 4.04 (m, 2H, CH$_2$), 4.22 (m, 3H, C$_5$·CH$_2$ and C$_4$·H), 5.42 (m, 1H C$_3$·H), 6.24 (t, 1H, J$_{1',2'}$=6.20 Hz, C$_1$·H), 7.04 (s, 1H, ImH), 7.12 (t, 1H, NH), 7.32 (s, 1H, ImH), 8.00 (s, 1H, ImH), 8.12 (s, 1H, C$_8$H), 10.14 (b s, 1H, NH). Anal. Calcd for C$_{28}$H$_{40}$N$_8$O$_6$: C, 57.52; H, 6.89; N, 19.17. Found: C, 57.49; H, 6.81: N, 19.09.

Example 14

N$_2$-Isobutyryl-N$_2$-[imidazol-1-yl(propyl)]-9-(2'-deoxy-β-D-erythro-pentofuranosyl)adenosine. (15)

Method 1: To a stirred solution of 13 (2.6 g, 3.43 mmol) in dry tetrahydrofuran (60 mL) was added tetrabutylammonium fluoride (1M solution in THF, 17.15 mL, 17.15 mmol) at room temperature. The reaction mixture was stirred at room temperature for 1 hour and quenched with H$^+$ resin. The resin was filtered, and washed with pyridine (20 mL) and methanol (50 mL). The filtrate was evaporated to dryness and the residue on purification over silica column using CH$_2$Cl$_2$/MeOH (95:5) gave the title compound in 59% (1 g) yield: $^1$H NMR (Me$_2$SO-d$_6$) δ 1.04 (m, 6H, Isobutyryl CH$_3$), 1.98 (m, 2H, CH$_2$), 2.22 (m, 1H, Isobutyryl CH), 2.70 (m, 1H, C$_2'$H), 2.98 (m, 1H, C$_2'$H), 3.22 (m, 2H CH$_2$), 3.52 (2 m, 2H, C$_5'$CH$_2$), 3.82 (m, 1H, C$_4'$H), 4.04 (m, 2H, CH$_2$), 4.38 (m, 1H, C$_3'$H), 4.92 (b s, 1H, OH), 5.42 (b s, 1H, OH) 6.22 (t, 1H, J$_{1',2'}$=6.20 Hz, C$_1'$H), 6.92 (s, 1H, ImH), 7.06 (t, 1H, NH), 7.24 (s, 1H, ImH), 7.74 (s, 1H, ImH), 8.12 (s, 1H, C$_8$H), 10.08 (b s, 1H, NH). Anal. Calcd for C$_{20}$H$_{28}$N$_8$O$_4$·H$_2$O; C, 54.04; H, 6.35; N, 25.21. Found: C, 54.14; H, 6.53; N, 25.06.

Method 2: To an ice cold (0 to –5° C.) solution of 14 (7.4 g. 12.65 mmol) in pyridine:EtOH:H$_2$O (70:50:10 mL) was added 1 N KOH solution (0° C., 25 mL, 25 mmol) at once. After 10 minutes of stirring, the reaction was quenched with H$^+$ resin (pyridinium form) to pH 7. The resin was filtered, and washed with pyridine (25 mL) and methanol (100 mL). The filtrate was evaporated to dryness and the residue was purified by flash chromatography over silica gel using CH$_2$Cl$_2$/MeOH (9:1) as eluent. The pure fractions were pooled together and evaporated to give 1.8 g (37%) of 15.

Example 15

5'-O-(4,4'-Dimethoxytrityl)-N$_6$-isobutyryl-N$_2$-[imidazol-1-yl (propyl)]-9-(2'deoxy-β-D-erythro-pentofuranosyl) adenosine. (16)

To a well dried (coevaporated three times with dry pyridine before use) solution of 15 (3.6 g, 8.11 mmol) in dry pyridine (100 mL) was added triethylamine (1.01 g, 10.00 mmol) followed by 4,4'-dimethoxytrityl chloride (3.38 g, 10.00 mmol) at room temperature. The reaction mixture was stirred under argon for 10 hours and quenched with methanol (20 mL). After stirring for 10 minutes, the solvent was removed under reduced pressure. The residue was dissolved in dichloromethane (250 mL), washed with water (50 mL), and brine (50 mL), and dried over MgSO$_4$. The dried organic extract was evaporated to dryness to an orange foam. The foam was purified by flash chromatography over silica gel using CH$_2$Cl$_2$/MeOH (95:5) as eluent. The required fractions were collected together and evaporated to give 4.6 g (76%) of 16 as amorphous solid: $^1$H NMR (Me$_2$SO-d$_6$) δ 1.04 (m, 6H, Isobutyryl CH$_3$), 1.90 (m, 2H, CH$_2$), 2.30 (m, 1H, C$_2'$H), 2.82 (m, 1H, C$_2'$H), 2.94 (m, 1H, Isobutyryl CH), 3.14 (m, 4H, CH$_2$ and C$_5'$CH$_2$), 3.72 (m, 6H, OCH$_3$), 3.92 (m, 3H, CH$_2$ and C$_4'$H), 4.44 (m, 1H, C$_3'$H), 5.44 (b s, 1H, C$_5'$OH), 6.28 (t, 1H, J$_{1',2'}$=6.20 Hz, C$_1'$H), 6.72–7.32 (m, 18H, ImH, NH and ArH), 7.64 (s, 1H ImH), 8.02 (s, 1H, C$_8$H), 10.10 (b s, 1H, NH). Anal. Calcd for C$_{41}$H$_{46}$N$_8$O$_6$: C, 65.93; H, 6.21; N, 15.00. Found: C, 65.81; H, 6.26; N, 14.71.

Example 16

3'-O-[(N,N-diisopropylamino)(β-cyanoethoxy) phosphanyl]-5'-O-(4,4'-dimethoxytrityl-N$_6$-isobutyryl-N$_2$-[imidazol-1-yl(propyl)]-9-(2'deoxy-β-D-erythro-pentofuranosyl)adenosine. (17)

The substrate 16 (4.2 g, 5.6 mmol) was coevaporated with dry pyridine (50 mL) three times. The resulting residue was dissolved in dry dichloromethane (50 mL) and cooled to 0° C. in a ice bath. To this cold stirred solution was added N,N-diisopropylethylamine (1.44 g, 11.2 mmol) followed by (β-cyanoethoxy)chloro (N,N-diisopropylamino)phosphane (1.32 g, 5.6 mmol) over a period of 15 minutes. After the addition, the reaction mixture was stirred at 0° C. for 1 hour and room temperature for 2 hours. The reaction was diluted with dichloromethane (150 mL) and washed with 5% NaHCO$_3$ solution (25 mL) and brine (25 mL). The organic extract was dried over MgSO$_4$ and the solvent was removed under reduced pressure. The residue was purified by flash chromatography over silica gel using CH$_2$Cl$_2$/MeOH (98:2) containing 1% triethylamine as eluent. The pure fractions were collected together and evaporated to dryness to give 3.9 g (73%) of 17.

Example 17

N$_2$-[Imidazol-4-yl(ethyl)]-9-(2'-deoxy-β-D-erythro-pentofuranosyl)guanosine. (18)

A mixture of 3 and histamine (4.4 g, 40.00 mmol) in 2-methoxyethanol (60 mL) was heated at 110° C. in a steel bomb for 12 hours. The steel bomb was cooled to 0° C., opened carefully, and the precipitated solid was filtered, washed with acetone and dried. The dried material was recrystallized from DMF/H$_2$O for analytical purposes. Yield 6 g (79%): mp 220–22° C.: $^1$H NMR (Me$_2$SO-d$_6$) δ 2.22 (m, 1H, C$_2'$H), 2.64 (m, 1H, C$_2'$H), 2.80 (m, 1H, CH$_2$), 3.52 (m, 4H, CH$_2$ and C$_5'$CH$_2$), 3.80 (m, 1H, C$_4'$H), 4.42 (m, 1H, C$_3'$H), 4.98 (b s, 1H, C$_5'$OH), 5.44 (b s, 1H, C$_3'$OH), 6.16 (t, 1H, J$_{1',2'}$=6.20 Hz, C$_1'$H), 6.44 (b s, 1H, NH), 6.84 (s, 1H, ImH), 7.56 (s, 1H, ImH), 7.92 (s, 1H, C$_8$H), 10.60 (b s, 1H, NH), 11.90 (b s, 1H, NH). Anal. Calcd for C$_{15}$H$_{19}$N$_7$O$_4$: C, 49.85; H, 5.30; N, 27.13. Found: C, 49.61; H, 5.21; N, 26.84.

Example 18

3',5'-O-(Tetraisopropyldisiloxane-1,3-diyl)-N$_2$-(imidazol-4-yl(ethyl)-9-(2'-deoxy-β-D-erythro-pentofuranosyl) guanosine. (19)

To a stirred suspension of 18 (2.4 g, 6.65 mmol) in dry DMF (50 mL) and dry pyridine (20 mL) was added triethylamine (4.04 g, 40.00 mmol) followed by 1,3-dichloro-1,1, 3,3-tetraisopropyldisiloxane (4.18 g, 13.3 mmol) at room temperature. After the addition of TipSiCl, the reaction mixture was stirred overnight and evaporated to dryness. The residue was purified by flash chromatography over silica gel using CH$_2$Cl$_2$/MeOH (9:1) as eluent. The pure fractions were pooled together and evaporated to dryness to give 3.2 g (80%) of 19. The pure product was crystallized from acetone/dichloromethane as colorless solid. mp 245–247° C.: $^1$H NMR (Me$_2$SO-d$_6$) δ 1.00 (m, 28H), 2.46 (m, 1H, C$_2'$H), 2.72 (m, 1H, C$_2'$H), 2.84 (m, 1H, CH$_2$), 3.54 (m, 2H, CH$_2$), 3.90 (m, 3H, C$_4'$H and C$_5'$CH$_2$), 4.70 (m, 1H, C$_3'$H), 6.12 (t, 1H, J$_{1',2'}$=6.20 Hz, C$_1'$H), 6.68 (b s, 1H, NH), 7.20 (s, 1H, ImH), 7.80 (s, 1H, ImH), 8.40 (s, 1H, C$_8$H), 10.72 (b s, 1H, NH). Anal. Calcd for C$_{27}$H$_{45}$N$_7$O$_5$Si$_2$: C, 53.70; H, 7.51; N, 16.24. Found: C, 53.38; H, 7.63; N, 15.86.

Example 19

3'5'-O-(Tetraisopropyldisiloxane-1,3-diyl)-6-O-diphenyl-carbamoyl-N$_2$-[(N$_1$-diphenylcarbamoyl)imidazol-4-yl (ethyl)]-9-(2'-deoxy-β-D-erythro-pentofuranosyl) guanosine. (20)

To a well stirred solution of the substrate 19 (6.03 g, 10.00 mmol) in dry DMF (50 mL) and dry pyridine (50 mL) was added N,N-diisopropylethylamine (5.16 g, 40.00 mmol) followed by diphenylcarbamoyl chloride (6.93 g, 30.00 mmol) at room temperature. The reaction mixture was allowed to stir at room temperature for 5 hours and evaporated to dryness. The residue was dissolved in $CH_2Cl_2$ (400 mL), washed with water (100 mL) and brine (50 mL), dried over $MgSO_4$, and evaporated to dryness. The residue was purified by flash chromatography using hexane/acetone (8:2) to give the title compound in 78.5% (7.8 g) yield: $^1H$ NMR ($Me_2SO-d_6$) δ 1.04 (m,28H), 2.54 (m, 1H, $C_2$H), 2.65 (m, 1H, $C_2$H), 2.72 (m, 2H, $CH_2$), 3.64 (m, 2H, $CH_2$), 3.86 (m, 1H, $C_4$H), 4.00 (m, 2H, $C_5$,$CH_2$), 4.74 (m, 1H, $C_3$H), 5.30 (b s, 1H, NH), 6.22 (m, 1H, $C_1$H), 6.72 (s, 1H, ImH), 7.12–7.50 (m, 20H, ArH), 7.70 (s, 1H, ImH), 7.86 (s, 1H, $C_8$H). Anal. Calcd for $C_{53}H_{63}N_9O_7Si_2$: C, 64.02; H, 6.39; N, 12.68. Found: C, 64.13; H, 6.43; N, 12.79.

Example 20

6-O-Diphenylcarbamoyl-$N_2$-[($N_1$-diphenylcarbamoyl) imidazol-4-yl(ethyl)]-9-(2'-deoxy-β-D-erythro-pentofuranosyl)guanosine. (21)

To a stirred solution of the protected derivative of 20 (1.8 g, 1.81 mmol) in pyridine/THF (30:20 mL) was added a 0.5M tetrabutyl-ammonium flouride [prepared in a mixture of tetrahydrofuran-pyridine-water (8:1:1;v/v/v; 20 mL)] at room temperature. The reaction mixture was stirred for 15 minutes and quenched with H$^+$ resin (pydinium form) to pH 6–7. The resin was filtered off, and washed with pyridine (25 mL) and methanol (30 mL). The filtrate was evaporated to dryness and the residue was purified by flash chromatography using $CH_2Cl_2$/MeOH (95:5) to give 1.2 g (88%) of 21 as a colorless amorphous solid: $^1H$ NMR ($Me_2SO-d_6$) δ 2.32 (m, 1H, $C_2$H), 2.72 (m, 2H, $CH_2$), 2.94 (m, 1H, $C_2$H), 3.46 (m, 1H, $C_4$H), 3.54–3.88 (m, 4H, $CH_2$ and $C_5$,$CH_2$), 4.00 (b s, 1H, $C_3$H), 5.20 (b s, 2H, OH), 5.42 (t, 1H, NH), 6.10 (t, 1H, $J_{1',2'}$=6.20 Hz $C_1$H), 6.80 (s, 1H, ImH), 7.14–7.48 (m, 20H, ArH), 7.64 (s, 1H, ImH), 7.74 (s, 1H, $C_8$H). Anal. Calcd for $C_{41}H_{37}N_9O_6$: C, 65.50; H, 4.96; N, 16.77. Found: C, 65.31; H, 5.10; N, 16.40.

Example 21

5'-O-(4,4'-Dimethoxytrityl)-6-diphenylcarbamoyl-$N_2$-[($N_1$-diphenylcarbamoyl)imidazol-4-yl(ethyl)]-9-(2'-deoxy-β-D-erythro-pentofuranosyl)guanosine. (22)

To a well dried solution of the substrate 21 (1.4 g, 1.87 mmol) in dry pyridine (70 mL) was added triethylamine (0.30 g, 3.0 mmol) followed by 4,4'-dimethoxytrityl chloride (0.85 g, 2.5 mmol) at room temperature. The stirring was continued overnight under argon atmosphere. Methanol (10 mL) was added, stirred for 10 minutes and evaporated to dryness. The residue was dissolved in $CH_2Cl_2$ (150 mL), washed with water (20 mL) and brine (20 mL), dried over $MgSO_4$, and the solvent removed under reduced pressure. The crude product was purified by flash chromatography over silica gel using $CH_2Cl_2$/acetone (7:3) containing 1% triethylamine as eluent. Yield 1.4 g (71%): $^1H$ NMR ($Me_2SO-d_6$) δ 2.44 (m, 1H, $C_2$H), 2.62 (m, 2H, $CH_2$), 2.98 (m, 1H, $C_2$H), 3.26 (m, 4H, $CH_2$ and $C_5$,$CH_2$), 3.40 (m, 1H, $C_4$H), 3.68 (2 s, 6H, 2H $OCH_3$), 4.00 (m, 1H, $C_3$H), 5.34 (t, 1H, NH), 5.44 (b s, 1H, $C_3$,OH), 6.12 (m, 1H, $C_1$H), 6.66–7.48 (m, 34H, ImH and ArH), 7.62 (s, 1H, ImH), 7.78 (s, 1H, $C_8$H). Anal. Calcd for $C_{62}H_{55}N_9O_{84}$: C, 70.64; H, 5.26; N, 11.96. Found: C, 70.24; H, 5.39; N, 11.66.

Example 22

3'-O-[(N,N-Diisopropylamino)(β-cyanoethoxy) phosphanyl]-5'-O-(4,4'-dimethoxytrityl)-6-O-diphenylcarbamoyl-$N_2$-[($N_1$-diphenylcarbamoyl)imidazol-4-yl(ethyl)]-9-(2'-deoxy-β-D-erythro-pentofuranosyl) guanosine. (23)

Well dried 22 was dissolved in dry dichloromethane (30 mL) and cooled to 0° C. under argon atmosphere. To this cold stirred solution was added N,N-diisopropylethylamine (0.39 g, 3.00 mmol) followed by (β-cyanoethoxy)chloro (N,N-diisopropylamino)phosphane (0.71 g, 3.0 mmol) over a period of 10 minutes. The reaction mixture was allowed to stir at room temperature for 2 hours and diluted with $CH_2Cl_2$ (120 mL). The organic layer was washed with 5% $NaHCO_3$ (25 mL), water (25 mL), and brine (25 mL). The extract was dried over anhydrous $MgSO_4$ and evaporated to dryness. The residue was purified by flash using hexane/ethyl acetate (3:7) containing 1% triethylamine as eluent. The pure fractions were pooled together and concentrated to dryness to give 1.0 g (70%) of 23 as a foam: $^1H$ NMR ($Me_2SO-d_6$) δ 1.12 (m, 12H, 2 Isobutyryl $CH_3$), 2.52 (m, 5H, $C_2$H, $CH_2$ and Isobutyryl CH), 2.62 (m, 2H), 3.06 (m, 1H, $C_2$H), 3.24 (m, 2H, $CH_2$) 3.40 (m, 2H, $CH_2$), 3.50–3.80 (m, 10H, 2$OCH_3$, $CH_2$ and $C_5$,$CH_2$), 4.08 (m, 1H, $C_4$H), 4.82 (m, 1H, $C_3$H), 5.74 (b s, 1H, NH), 6.24 (m, 1H, $C_1$H), 6.64–7.52 (m, 34H, ImH and ArH), 7.62 (s, 1H, ImH), 7.94 (s, 1H, $C_8$H).

Example 23

$N_2$-Nonyl-9-(2'-deoxy-β-D-erythro-pentofuranosyl) guanosine. (24)

A mixture of 2-chloro-2'-deoxyinosine and compound 3 (9.5 g, 33.22 mmol) and nonylamine (9.58 g, 67.00 mmol) in 2-methoxyethanol (60 mL) was heated at 120° C. for 12 hours in a steel bomb. The steel bomb was cooled to 0° C., opened carefully and the solvent removed under reduced pressure. The residue was coevaporated with a mixture of dry pyridine/dry toluene (50 mL each). The above process was repeated for three times and the resultant residue was carried over to the next reaction without further purification. A small amount of material was precipitated from the solution which was filtered and dried: mp 164–167° C.: $^1H$ NMR ($Me_2SO-d_6$) δ 0.82 (t, 3H, $CH_3$), 1.24 (m, 12H, 6 $CH_2$), 1.48 (m, 2H, $CH_2$), 2.18 (m, 1H, $C_2$H), 2.62 (m, 1H, $C_2$H), 3.22 (m, 2H, $CH_2$), 3.50 (m, 2H, $C_5$,$CH_2$), 3.78 (m, 1H, $C_4$H), 4.32 (m, 1H, $C_3$H), 4.84 (t, 1H, $C_5$,OH), 5.24 (m, 1H, $C_3$OH), 6.12 (m, 1H, $C_1$H), 6.44 (b s, 1H, NH), 7.86 (s, 1H, $C_8$H), 10.52 (b s, 1H, NH). Anal. Calcd for $C_{19}H_{31}N_5O_4$·$H_2O$: C, 55.45; H, 8.08; N, 17.00. Found: C, 55.96; H, 7.87; N, 16.59.

Example 24

3',5'-Tri-O-isobutyryl-$N_2$-isobutyryl-$N_2$-nonyl-9-(2'-deoxy-β-D-erythro-pentofuranosyl)guanosine. (25)

The crude product of 24 (18 g, 32.91 mmol) was coevaporated three times with a mixture of dry DMF/pyridine (50 mL each). The residue was dissolved in dry pyridine (150 mL) and cooled to 0° C. To this cold stirred solution was added triethylamine (30.3 g, 300 mmol) followed by isobutyryl chloride (21.2 g, 200 mmol) over a 30 minute period. After the addition of IbCl, the reaction mixture was allowed to stir at room temperature for 10 hours and was then evaporated to dryness. The residue was partitioned between $CH_2Cl_2$/water (300:150 mL) and extracted in $CH_2Cl_2$. The organic extract was washed with 5% $NaHCO_3$ (50 mL), water (50 mL) and brine (50 mL), dried over anhydrous $MgSO_4$, and evaporated to dryness. The residue was purified by flash chromatography over silica gel using $CH_2Cl_2$/EtOAc (6:4) as eluent. The pure fractions were pooled and evaporated to give 10 g (40%) of 25 as foam: $^1H$ NMR ($Me_2SO-d_6$) δ 0.82 (t, 3H, $CH_3$), 1.12 (m, 30H, 3 Isobutyryl $CH_3$ and 6 $CH_2$), 1.44 (m, 2H, $CH_2$), 2.54 (m, 4H, $C_2$'H and 3 Isobutyryl CH), 3.00 (m, 1H, $C_2$H), 3.62 (m, 2H, $CH_2$), 4.20 (m, 3H, $C_5$,$CH_2$ and $C_4$H), 5.32 (m, 1H, $C_3$H), 6.24 (t, 1H, $J_{1',2'}$=6.20 Hz, $C_1$H), 8.28 (s, 1H, $C_8$H), 12.82 (b s, 1H, NH). Anal. Calcd for $C_{31}H_{49}N_5O_7$: C, 61.67; H, 8.18; N, 11.60. Found: C, 61.59; H, 8.23; N, 11.34.

Example 25

3',5'-O-(Tetraisopropyldisiloxane-1,3-diyl)-$N_2$-nonyl-9-(2'-deoxy-β-D-erythro-pentofuranosyl)guanosine. (26)

To a well dried solution of the crude product of 24 (16.4 g, 30.00 mmol) in dry DMF (100 mL) and dry pyridine (100 mL) was added triethylamine (10.1 g, 100 mmol) and 1,3-dichloro-1,1,3,3-tetraisopropyldisiloxane (15.75 g, 50 mmol) during 30 min period. The reaction mixture was allowed to stir at room temperature overnight and was then evaporated to dryness. The crude product was dissolved in $CH_2Cl_2$ (300 mL), washed with water (100 mL), and brine (50 mL). The extract was dried over $MgSO_4$ and the solvent was removed under reduced pressure. The residue was purified over silica column using $CH_2Cl_2$/acetone (7:3) to give 14 g (59%) of 26 as colorless foam. This on crystallization with the same solvent provided crystalline solid. mp 210–212° C.: $^1H$ NMR ($Me_2SO$-$d_6$) δ 0.82 (m, 3H, $CH_3$), 1.02 (m, 28H), 1.24 (m, 12H, 6 $CH_2$), 1.50 (m, 2H, $CH_2$), 2.42 (m, 1H, $C_2·H$), 2.84 (m, 1H, $C_2·H$), 3.24 (m, 2H, $CH_2$), 3.82 (m, 2H, $C_5·CH_2$), 3.92 (m, 1H, $C_4·H$), 4.72 (m, 1H, $C_3·H$), 6.12 (t, 1H, $J_{1',2'}$=6.20 Hz, $C_1·H$), 6.36 (b s, 1H, NH), 7.78 (s, 1H, $C_8H$), 10.38 (b s, 1H, NH). Anal. Calcd for $C_{31}H_{57}N_5O_5Si_2$: C, 58.54; H, 9.03; N, 11.01. Found: C, 58.64; H, 9.09; N, 10.89.

Example 26

$N_2$-Isobutyryl-3',5'-O-(tetraisopropyldisiloxane-1,3-diyl)-$N_2$-nonyl-9-(2'-deoxy-β-D-erythro-pentofuranosyl)guanosine. (27)

To a solution of 26 (14.0 g, 17.72 mmol) in dry DMF (50 mL) and dry pyridine (150 mL) was added triethylamine (3.54 g, 35.00 mmol) and isobutyryl chloride (3.71 g, 3.5 mmol). The reaction mixture was stirred at room temperature overnight and evaporated to dryness. The residue was dissolved in $CH_2Cl_2$ (250 mL), washed with 5% $NaHCO_3$ (50 mL), water (50 mL) and brine (50 mL), dried over $MgSO_4$, and the solvent removed under reduced pressure. The residue was purified by flash chromatography over silica gel using $CH_2Cl_2$/acetone (9:1) as eluent. The pure fractions were pooled together and evaporated to dryness to give 12.0 g (77%) of the title compound as foam: $^1H$ NMR ($Me_2SO$-$d_6$) δ 0.80 (m, 3H, $CH_3$), 0.98 (m, 34H), 1.20 (m, 12H, 6 $CH_2$), 1.42 (m, 2H, $CH_2$), 2.52 (m, 2H, $C_2·H$ and Isobutyryl CH), 2.82 (m, 1H, $C_2·H$), 3.62 (m, 2H, $CH_2$), 3.84 (m, 3H, $C_5·CH_2$ and $C_4·H$), 4.72 (m, 1H, $C_3·H$), 6.22 (t, 1H, $J_{1',2'}$=6.20 Hz, $C_1·H$), 8.18 (s, 1H, $C_8H$), 12.80 (b s, 1H, NH).

Example 27

$N_2$-Isobutyryl-$N_2$-nonyl-9-(2'-deoxy-β-D-erythro-pentofuranosyl)guanosine. (28)

Method 1: The substrate of 25 (5.00 g, 6.6 mmol) was dissolved in methanol (100 mL) and treated with concentrated $NH_4OH$ (100 mL). The reaction mixture was stirred for 4 hours at room temperature and evaporated to dryness. The residue was purified by flash chromatography over silica gel using $CH_2Cl_2$/MeOH (95:5) as eluent. The required fractions were collected together and evaporated to dryness and the residue on crystallization from $CH_2Cl_2$/acetone gave a colorless crystalline solid. yield 2 g (66%): mp 113–115° C.

Method 2: A stirred solution of 27 (4.29 g, 4.99 mmol) in dry tetrahydrofuran (50 mL) was treated with 1M solution of tetrabutylammonium fluoride (20 mL, 20.00 mmol). The reaction mixture was stirred at room temperature for 4 hours and evaporated to dryness. The residue was purified by flash chromatography using $CH_2Cl_2$/MeOH (95:5) to give 1.59 g (69%) of 28: $^1H$ NMR ($Me_2SO$-$d_6$) δ 0.80 (m, 3H, $CH_3$), 0.98 (m, 6H, Isobutyryl $CH_3$), 1.16 (m, 12H, 6 $CH_2$), 1.42 (m, 2H, $CH_2$), 2.24 (m, 1H, $C_2·H$), 2.52 (m, 2H, $C_2·H$ and Isobutyryl CH), 3.50 (m, 2H, $C_5·CH_2$), 3.62 (m, 2H, $CH_2$), 3.82 (m, 1H, $C_4·H$), 4.36 (m, 1H, $C_3·H$), 4.94 (t, 1H, $C_5·OH$), 5.34 (m, 1H, $C_3·OH$), 6.22 (t, 1H, $J_{1',2'}$=6.20 Hz, $C_1·H$), 8.28 (s, 1H, $C_8H$), 12.78 (b s, 1H, NH). Anal. Calcd for $C_{23}H_{37}N_5O_5$: C, 59.59; H, 8.05; N, 15.11. Found: C, 59.50; H, 8.08; N, 15.06.

Example 28

5'-O-(4,4'-Dimethoxytrityl)-$N_2$-isobutyryl-$N_2$-nonyl-9-(2'-deoxy-β-D-erythro-pentofuranosyl)guanosine. (29)

To a stirred solution of 28 (2.00 g, 4.32 mmol) in dry pyridine (75 mL) was added triethylamine (0.61 g, 6.00 mmol) and 4,4'-dimethoxytrityl chloride (2.03 g, 6.00 mmol) at room temperature. The reaction was stirred under argon atmosphere for 6 hours and quenched with methanol (10 mL). The solvent was removed under reduced pressure and the residue dissolved in $CH_2Cl_2$ (150 mL). The organic extract was washed with water (25 mL) and brine (25 mL), dried over $MgSO_4$, and evaporated to dryness. The residue was purified by flash chromatography over silica gel using $CH_2Cl_2$/acetone (7:3) as eluent. The pure fractions were pooled together and evaporated to give 2 g (60%) of 29 as foam: $^1H$ NMR ($Me_2SO$-$d_6$) δ 0.80 (m, 3H, $CH_3$), 0.96 (m, 6H, Isobutyryl $CH_3$), 1.16 (m, 12H, 6 $CH_2$), 1.36 (m, 2H, $CH_2$), 2.32 (m, 1H, $C_2·H$), 2.60 (m, 1H, Isobutyryl CH), 2.72 (m, 1H, $C_2·H$), 3.12 (m, 2H, $CH_2$), 3.52 (m, 2H, $C_5·CH_2$) 3.70 (2 d, 6H, 2$OCH_3$), 3.90 (m, 1H, $C_4·H$), 4.34 (m, 1H, $C_3·H$), 5.36 (m, 1H, $C_3·OH$), 6.26 (t, 1H, $J_{1',2'}$=6.20 Hz, $C_1·H$), 6.70–7.36 (m, 13H, ArH), 8.18 (s, 1H, $C_8H$). Anal. Calcd for $C_{44}H_{56}N_5O_7$: C, 68.90; H, 7.36; N, 9.31. Found: C, 68.76; H, 7.47; N, 9.09.

Example 29

3'-O-[(N,N-Diisopropylamino)(β-cyanoethoxy)phosphanyl]-5'-O-(4,4'-dimethoxytrityl)-$N_2$-isobutyryl-$N_2$-nonyl-9-(2'-deoxy-β-D-erythro-pentofuranosyl)guanosine. (30)

A well dried solution of 29 (1.7 g, 2.22 mmol) in dry dichloromethane (30 mL) was cooled to 0° C. To this cold solution was added N,N-diisopropyethylamine (0.57 g, 4.4 mmol) and (β-cyanoethoxy)chloro(N,N-diisopropylamino)phosphane (0.94 g, 4.0 mmol) under argon atmosphere. The reaction mixture was stirred at room temperature for 2 hours and diluted with $CH_2Cl_2$ (170 mL). The organic extract was washed with 5% $NaHCO_3$ (25 mL), water (25 mL) and brine (25 mL), dried over $Na_2SO_4$, and evaporated to dryness. The residue was purified on a silica column using $CH_2Cl_2$/acetone (9:1) containing 1% triethylamine as eluent. The pure fractions were pooled together and evaporated to dryness to give 1.5 g (53%) of 30.

Example 30

3',5'-O-(Tetraisopropyldisiloxane-1,3-diyl)-2-chloro-9-(2'-deoxy-β-D-erythro-pentofuranosyl)adenosine. (31)

Compound 31 was prepared from compound 10 by following the procedure used for the preparation of 12. Starting materials used: 10 (4.30 g, 15.09 mmol), 1,3-dichloro-1,1,3,3-tetraisopropyldisiloxane (4.74 g, 15.1 mmol), dry TEA (3.05 g, 30.2 mmol), and dry pyridine (100 mL). The crude product was purified by flash chromatography using $CH_2Cl_2$/acetone (7:3) as eluent to give 7.3 g (92%) of 31. The pure product was crystallized from ethylacetate/hexane as a colorless solid. mp 183–185° C.: $^1H$ NMR ($Me_2SO$-$d_6$) δ 1.00 (m, 28H), 2.54 (m, 1H, $C_2·H$), 2.82 (m, 1H, $C_2·H$), 3.76 (m, 1H, $C_4·H$), 3.86 (m, 2H, $C_5·CH_2$), 5.08 (m, 1H, $C_3·H$), 6.22 (t, 1H, $J_{1',2'}$=6.20 Hz, $C_1·H$), 7.82 (b s, 2H, $NH_2$), 8.22 (s, 1H, $C_8H$. Anal. Calcd for $C_{22}H_{38}ClN_5O_4Si_2$: C, 50.02; H, 7.25; N, 13.26, Cl, 6.72. Found: C, 50.24; H, 7.28; N, 13.07, Cl, 6.63.

Example 31

3',5'-O-(Tetraisopropyldisiloxane-1,3-diyl)-2-chloro-$N_6$-benzoyl-9-(2'-deoxy-β-D-erythro-pentofuranosyl)adenosine. (32)

A well dried solution of 31 (8 g, 15.00 mmol) in dry pyridine (150 mL) was allowed to react with triethylamine (4.55 g, 45.00 mmol) and benzoyl chloride (6.3 g, 45.00 mmol) at room temperature for 12 hours under argon atmosphere. The reaction mixture was evaporated to dryness. The residue was partitioned between $CH_2Cl_2$/water and extracted in $CH_2Cl_2$ (2×150 mL). The organic extract was washed with brine (60 mL), dried over $MgSO_4$ and evaporated to dryness. The residue was purified by silica column using $CH_2Cl_2$/acetone as eluent and crystallization from the same solvent gave 8.2 g (86%) of 32. mp 167–170° C.: $^1H$ NMR ($Me_2SO-d_6$) δ 1.00 (m, 28H), 2.60 (m, 1H, $C_2H$), 3.02 (m, 1H, $C_2H$), 3.84 (m, 3H, $C_5CH_2$ and $C_4H$), 5.04 (m, 1H, $C_3H$), 6.34 (d, 1H, $C_1H$), 7.42–7.84 (m, 5H, ArH), 8.70 (s, 1H, $C_8H$). Anal. Calcd for $C_{29}H_{42}ClN_5O_5Si_2$: C, 55.08; H, 6.69; N, 11.08, Cl, 5.61. Found: C, 55.21; H, 6.79; N, 11.19, Cl, 5.70.

Example 32

$N_6$-Benzoyl-2-chloro-9-(2'-deoxy-β-D-erythro-pentofuranosyl) adenosine. (33)

To a stirred solution of 32 (7.9 g, 12.5 mmol) in dry THF (100 mL) was added 1M solution of tetrabutylammonium fluoride (50 mL, 50.00 mmol) slowly over a 15 minute period at room temperature. The reaction mixture was stirred for 6 hours and evaporated to dryness. The residue was purified by flash chromatography using $CH_2Cl_2$/acetone (7:3) as eluent to give 3.88 g (80%) of 33. mp>275° C. dec: $^1H$ NMR ($Me_2SO-d_6$) δ 2.34 (m, 1H, $C_2H$), 2.72 (m, 1H, $C_2H$), 3.58 (m, 2H, $C_5CH_2$), 3.88 (m, 1H, $C_4H$), 4.42 (m, 1H, $C_3H$), 4.96 (t, 1H, $C_5OH$), 5.38 (d, 1H, $C_3OH$), 6.40 (t, 1H, $J_{1',2'}$=6.20 Hz, $C_1H$), 7.52 (m, 2H, ArH), 7.64 (m, 1H, ArH), 8.04 (d, 2H, ArH), 8.70 (s, 1H, $C_8H$), 11.52 (b s, 1H, NH). Anal. Calcd for $C_{17}H_{16}ClN_5O_4$: C, 52.37; H, 4.14; N, 17.97; Cl, 9.11. Found: C, 52.31; H, 4.07; N, 17.94; Cl, 9.03.

Example 33

5'-O-(4,4'-Dimethoxytrityl)-$N_6$-benzoyl-2-chloro-9-(2'-deoxy-β-D-erythro-pentofuranosyl)adenosine. (34)

The compound was prepared from 33 by following the procedure used for the preparation of 8. Starting materials used: 33 (2.5 g. 6.43 mmol), 4,4'-dimethoxytrityl chloride (2.37 g, 7.0 mmol), dry TEA (0.71 g, 7.0 mmol) and dry pyridine (100 mL). The crude product was purified by flash chromatography using $CH_2Cl_2$/EtOAc (7:3) containing 1% triethylamine as the eluent to give 3 g (68%) of 34 as foam: $^1H$ NMR ($Me_2SO-d_6$) δ 2.34 (m, 1H, $C_2H$), 2.82 (m, 1H, $C_2H$) 3.18 (m, 2H, $C_5CH_2$), 3.64 (2d, 6H, $OCH_3$), 3.98 (m, 1H, $C_4H$), 4.44 (m, 1H, $C_3H$), 5.40 (d, 1H, OH), 6.42 (t, 1H, $J_{1',2'}$=6.20 Hz, $C_1H$), 6.74 (m, 4H, ArH), 7.16 (m, 7H, ArH), 7.32 (m, 2H, ArH), 7.52 (m, 7H, ArH), 7.64 (m, 1H, ArH), 8.04 (m, 2H, ArH), 8.58 (s, 1H, $C_8H$), 11.50 (b s, 1H, NH). Anal. Calcd for $C_{38}H_{34}ClN_5O_6$: C, 65.93; H, 4.95; N, 10.12; Cl, 5.13. Found: C, 65.55; H, 5.16; N, 9.73; Cl, 5.10.

Example 34

3'-O-[(N,N-Diisopropylamino)(β-cyanoethoxy)phosphanyl]-5'-O-(4,4'-dimethoxytrityl)-$N_6$-benzoyl-2-chloro-9-(2'-deoxy-β-D-erythro-pentofuranosyl)adenosine. (35)

The title compound was prepared from 34 by following the procedure used for the preparation of 9. Starting materials used: Compound 34 (2.4 g, 3.47 mmol), N,N-diisopropylethylamine (1.22 mL, 7.00 mmol), (β-cyanoethoxy) chloro(N,N-diisopropylamino)phosphene (1.65 g, 7.00 mmol) and dry $CH_2Cl_2$ (30 mL). The crude product was purified by flash chromatography using hexane-ethyl acetate (1:1) containing 1% triethylamine as eluent. The pure fractions were pooled together and evaporated to dryness to give 1.8 g (58%) of 35. The foam was dissolved in dry dichloromethane (10 mL) and added dropwise into a well stirred hexane (1500 mL) under argon atmosphere. After the addition, stirring was continued for an additional 1 hour and the precipitated solid was filtered, washed with hexane and dried over solid NaOH for 3 hours. The dried powder showed no traces of impurity in $^{31}P$ spectrum: $^1H$ NMR ($Me_2SO-d_6$) δ 1.18 (m, 12H, Isobutyryl $CH_3$), 2.58 (m, 3H, $C_2H$ and Isobutyryl CH), 2.98 (m, 1H, $C_2H$), 3.34 (d, 2H, $CH_2$), 3.64 (m, 2H, $C_5CH_2$), 3.72 (m, 8H, $2OCH_3$ and $CH_2$), 4.24 (m, 1H, $C_4H$), 4.82 (m, 1H, $C_3H$), 6.36 (t, 1H, $J_{1',2'}$=6.20 Hz, $C_1H$), 6.76 (m, 4H, ArH), 7.22 (m, 7H, ArH), 7.38 (m, 2H, ArH), 7.52 (m, 2H, ArH), 7.64 (m, 1H, ArH), 7.98 (m, 2H, ArH), 8.24 (s, 1H, $C_8H$), 9.34 (b s, 1H, NH).

Example 35

3',5'-O-(Tetraisopropyldisiloxane-1,3-diyl)-$N_2$-ethyl-9-(2'-deoxy-β-D-erythro-pentofuranosyl)guanosine. (36)

A solution of 3',5'-O-(tetraisopropyldisiloxane-1, 3-diyl)-2-chloro-9-(2'-deoxy-β-D-erythro-pentofuranosyl)inosine (5.0 g, 9.45 mmol) in 2-methoxyethanol (30 mL) was placed in a steel bomb and cooled to 0° C. Freshly condensed ethylamine (7.0 mL) was quickly added. The steel bomb was sealed and the reaction mixture was stirred at 90° C. for 16 hours. The vessel was cooled and opened carefully. The precipitated white solid was filtered and crystallized from methanol. The filtrate on evaporation gave solid which was also crystallized from methanol. Total yield 3. g (65%). mp >250° C. dec: $^1H$ NMR ($Me_2SO-d_6$) δ 1.06 (m, 31H), 2.32 (m, 1H, $C_2H$), 2.84 (m, 1H, $C_2H$), 3.26 (m, 2H, $CH_2$), 4.12 (m, 2H, $C_5CH_2$), 4.22 (m, 1H, $C_4H$), 4.70 (m, 1H, $C_3H$), 6.23 (t, 1H, $J_{1',2'}$=6.20 Hz, $C_1H$), 6.42 (m, 1H, NH), 7.87 (s, 1H, $C_8H$), 10.58 (b s, 1H, NH). Anal. Calcd for $C_{24}H_{43}N_5O_5Si_2$. C, 53.59; H, 8.06; N, 13.02. Found: C, 53.44; H, 8.24; N, 12.91.

Example 36

3',5'-O-(Tetraisopropyldisiloxane-1,3-diyl)-6-O-diphenyl-carbamoyl-$N_2$-ethyl-9-(2'-deoxy-β-D-erythro-pentofuranosyl) guanosine. (37)

Compound 36 (2.40 g, 4.46 mmol) was dissolved in anhydrous pyridine (30 mL) at room temperature. To this solution was added N,N-diisoproylethylamine (1.60 mL, 8.93 mmol) followed by diphenylcarbamoyl chloride (2.07 g, 8.93 mmol). The mixture was stirred at room temperature under argon atmosphere for 10 hours. A dark red solution was obtained, which was evaporated to dryness. The residue was purified by flash chromatography on a silica column using $CH_2Cl_2$/EtoAc as eluent. The pure fractions were collected together and evaporated to give a brownish foam (3.25 g, 99%). $^1H$ NMR ($Me_2SO-d_6$) δ 1.14 (t, 31H), 2.52 (m, 1H, $C_2H$), 3.04 (m, 1H, $C_2H$), 3.34 (m, 2H, $CH_2$), 3.87 (m, 3H, $C_5CH_2$ & $C_4H$), 4.83 (m, 1H, $C_3H$), 6.23 (m, 1H, $C_1H$), 7.36 (m, 11H, ArH & NH), 8.17 (s, 1H, $C_8H$). Anal. Calcd for $C_{37}H_{52}N_6O_6Si_2$. C, 60.71; H, 7.16; N, 11.48. Found: C, 60.33; H, 7.18; N, 11.21.

Example 37

6-O-Diphenylcarbamoyl-$N_2$-ethyl-9-(2'-deoxy-β-D-erythro-pentofuranosyl)guanosine. (38)

To a stirred solution of 37 (3.25 g, 4.47 mmol) in pyridine (25 mL) was added 0.5 M solution of tetrabutylammonium fluoride (prepared in pyridine/THF/water, 4/1/1,36mL, 17.88 mmol) at once. The reaction was allowed to stir for 10 minutes and quenched with $H^+$ resin (amberlite IRC 50) to pH 7. The resin was filtered and washed with pyridine (20 mL) and MeOH (20 mL). The filtrate was evaporated to dryness. The residue was purified using flash chromatography over a silica column using methylene chloride-acetone as eluent to give 1.84 g (84%) of the pure product as foam. $^1H$ NMR ($Me_2SO-d_6$) δ 1.14 (t, 3H, $CH_2CH_3$), 2.22 (m, 1H, $C_2H$), 2.76 (m, 1H, $C_2H$), 3.34 (m, 2H, $CH_2$), 3.57 (m, 2H, $C_{5'}CH_2$), 3.84 (m, 1H, $C_{4'}H$), 4.42 (m, 1H, $C_{3'}H$), 4.91 (t, 1H, $C_{5'}OH$), 5.32 (d, 1H, $C_{3'}OH$), 6.27 (t, 1H, $J_{1',2'}=6.20$ Hz $C_1H$), 7.29 (m, 1H, NH), 7.46 (m, 10H, ArH), 8.27 (s, 1H, $C_8H$). Anal. Calcd for $C_{25}H_{26}N_6O_5 \cdot ¾H_2O$. C, 59.61; H, 5.35; N, 16.68. Found: C, 59.83; H, 5.48; N, 16.21.

Example 38

$N_2$-Ethyl-9-(2'-deoxy-β-D-erythro-pentofuranosyl) guanosine. (39)

The intermediate of 38 (0.25 g, 0.51 mmol) was stirred in methanolic/ammonia (saturated at 0° C.) in a steel bomb at room temperature for 40 hours. The vessel was cooled to 0° C., opened carefully, and the solvent evaporated to dryness. The solid obtained was crystallized from methanol to give a white powder (0.95 g, 63%): mp 234–238° C. $^1$H NMR ($Me_2SO$-$d_6$) δ 1.14 (t, 3H, $CH_2CH_3$), 2.18 (m, 1H, $C_2H$), 2.67 (m, 1H, $C_2H$), 3.34 (m, 2H, $CH_2$), 3.52 (m, 2H, $C_{5'}CH_2$), 3.82 (m, 1H, $C_{4'}H$), 4.36 (m, 1H, $C_{3'}H$), 4.89 (t, 1H, $C_{5'}OH$), 5.30 (d, 1H, $C_{3'}OH$), 6.16 (t, 1H, $J_{1',2'}=6.20$ Hz $C_1H$), 6.44 (m, 1H, NH), 7.91 (s, 1H, $C_8H$), 10.58 (b s, 1H, NH).

Example 39

5'-O-(4,4'-Dimethoxytrityl)-6-O-diphenylcarbamoyl-$N_2$-ethyl-9-(2'-deoxy-β-D-erythro-pentofuranosyl)guanosine. (40)

Compound 38 (1.6 g, 3.26 mmol) was dried well by coevaporation with dry pyridine (3×50 mL). The dried material was dissolved in anhydrous pyridine (25 mL) and allowed to stir under argon atmosphere. To this stirred solution was added triethylamine (0.59 mL, 4.24 mmol) followed by DMTCl (1.44 g, 4.24 mmol). The reaction mixture was stirred at room temperature for 14 hours and quenched with methanol (10 mL). After stirring for 15 minutes, the solvent was removed and the residue was dissolved in methylene chloride (150 mL). The organic extract was washed with saturated $NaHCO_3$ solution (30 mL), water (30 mL), and brine (30 mL). The methylene chloride extract was dried and evaporated to dryness. The residue was purified by flash chromatography over silica gel using methylene chloride/acetone as eluent. The pure fractions were collected together and evaporated to give a foam (2.24 g, 87%). $^1$H NMR ($Me_2SO$-$d_6$) δ 1.10 (t, 3H, $CH_2CH_3$), 2.32 (m, 1H, $C_2H$), 2.82 (m, 1H, $C_2H$), 3.15 (m, 2H, $CH_2$), 3.34 (s, 6H, 2 $OCH_3$), 3.67 (m, 2H, $C_{5'}CH_2$), 3.96 (m, 1H, $C_{4'}H$), 4.42 (m, 1H, $C_{3'}H$), 5.36 (d, 1H, $C_{3'}OH$), 6.30 (t, 1H, $J_{1',2'}=6.20$ Hz, $C_1H$), 6.83 (m, 4H, ArH), 7.23 (m, 10H, ArH & NH), 8.17 (s, 1H, $C_8H$). Anal Calcd for $C_{45}H_{44}N_6O_7 \cdot ¼CH_3OH \cdot ¼ H_2O$. C, 68.50; H, 5.78; N, 10.60. Found: C, 68.72; H, 5.42; N, 10.40.

Example 40

3'-O-[(N,N-Diisopropylamino)(β-cyanoethoxy) phosphanyl]-5'-O-(4,4'-dimethoxytrityl)-6-O-diphenylcarbamoyl-$N_2$-ethyl-9-(2'-deoxy-β-D-erythro-pentofuranosyl)guanosine. (41)

The DMT derivative of 40 was dried well overnight at vacuum and dissolved in dry methylene chloride (25 mL). The solution was cooled to 0° C. under argon atmosphere. To this cold stirring solution N,N-diisopropylamine tetrazolide salt (0.24 g, 1.41 mmol) followed by phosphorylating reagent (1.71 mL, 5.66 mmol) were added. The mixture was stirred at room temperature for 12hours under argon. The solution was diluted with additional methylene chloride (100 mL) and washed with saturated $NaHCO_3$ solution (50 mL), water (50 mL), and brine (50 mL). The organic extract was dried and evaporated to dryness. The crude product was purified by flash column over silica gel using methylene chloride/ethyl acetate containing 1% triethylamine as eluent. The pure fractions were pooled and evaporated to give 2.5 g (91%) of 41.

Example 41

3',5'-Di-O-acetyl-$N_2$-acetyl-9-(2'-deoxy-β-D-erythro-pentofuranosyl)guanosine. (42)

Deoxyguanosine (26.10 g, 96.77 mmol) was coevaporated with dry pyridine/DMF (50 mL each) three times. The residue was suspended in dry DMF (50 mL) and dry pyridine (50 mL) at room temperature. To this stirring mixture was added N,N-dimethylaminopyridine (1.18 g, 9.67 mmol) followed by acetic anhydride (109.6 mL, 116 mmol) slowly keeping the temperature below 35° C. After the addition of $Ac_2O$, the reaction was placed at 80° C. for 4 hours under argon. It was cooled to room temperature and neutralized with 1N $NaCO_3$ solution. The mixture was extracted in $CH_2Cl_2$ (2×250 mL). The organic extract was washed with water (50 mL) and brine (50 mL), dried, and evaporated to dryness. The residue was crystallized from MeOH to give 29.1 g (76%): mp 217–219° C. $^1$H NMR ($Me_2SO$-$d_6$) δ 2.04 (s, 3H, $COCH_3$), 2.09 (s, 3H, $COCH_3$), 2.19 (s, 3H, $COCH_3$), 2.60 (m, 1H, $C_2H$), 3.02 (m, 1H, $C_2H$), 4.19 (m, 3H, $C_4H$ & $C_{5'}CH_2$), 5.31 (m, 1H, $C_{3'}H$), 6.21 (t, 1H, $J_{1',2'}=6.00$ Hz, $C_1H$), 8.27 (s, 1H, $C_8H$), 11.72 (b s, 1H, NH), 12.02 (b s, 1H, NH).

Example 42

6-O-Benzyl-9-(2'-deoxy-β-D-erythro-pentofuranosyl) guanosine. (43)

$N_2$,3',5'-Tri-O-acetyldeoxyguanosine 42 (1.18 g, 3 mmol) was suspended in dry dioxane (50 mL) under argon atmosphere. To this stirred suspension was added dry benzyl alcohol (0.81 g, 7.5 mmol) followed by triphenyl phosphine (1.96 g, 7.5 mmol). After stirring for 15 minutes, diethylazodicarboxylate (1.30 g, 7.5 mmol) was added dropwise over a 15 minute period at room temperature. The reaction mixture was stirred under argon overnight at room temperature. The solvent was removed and the residue treated with 0.1M sodium methoxide (75 mL) and stirred at room temperature overnight. Glacial acetic acid (0.45 mL) was added, the solvents were evaporated and the residue was partitioned between water and ethyl acetate. The ethyl acetate extracts were dried, evaporated and the residue was chromatographed over silica gel using $CH_2Cl_2$—MeOH mixture. The product (0.5 g, 75%) was obtained as an amorphous white solid after trituration with ether. $^1$H NMR ($Me_2SO$-$d_6$) δ 2.22 (m, 1H, $C_2H$), 2.60 (m, 1H, $C_2H$), 3.56 (m, 2H, $C_{5'}CH_2$), 3.80 (m, 1H, $C_{4'}H$), 4.37 (m, 1H, $C_{3'}H$), 5.01 (t, 1H, $C_{5'}OH$), 5.29 (b s, 1H, $C_{3'}OH$), 5.52 (s, 2H, $ArCH_2$), 6.23 (t, 1H, $J_{1',2'}=6.66$ Hz, $C_1H$), 6.52 (b s, 2H, $NH_2$), 7.40 (m, 2H, ArH), 7.50 (m, 2H, ArH), 8.11 (s, 1H, $C_8H$). Anal. Calcd for $C_{17}H_{19}N_5O_4$. C, 57.13; H, 5.36; N, 19.59. Found: C, 57.09; H, 5.42; N, 19.61.

Example 43

6-O-Benzyl-2-flouro-9-(2'-deoxy-β-D-erythro-pentofuranosyl) purine. (44)

To a stirred suspension of the substrate 43 (5.0 g, 14 mmol) in dry pyridine (20 ml) at "40° C. was added HF/pyridine (Aldrich 18,422-5 70%) in two portions (2×10 mL) under argon atmosphere. After the addition of HF/pyridine, the mixture was warmed up to −10° C., during that time all the solid had gone into solution. Tert-butyl nitrite (4.0 mL) was added slowly during the course of 10 minutes maintaining the temperature between −20° C. and −10° C. At intervals the reaction mixture was removed from the cooling bath and swirled vigorously to ensure thorough mixing. After complete conversion of the starting material (checked by TLC at 15 minute intervals), the reaction mixture was poured onto a vigorously stirred ice cold alkaline solution (70 g of $K_2CO_3$ in 150 mL of water). The gummy suspension was extracted with methylene chloride (2×200 mL). The organic extract was washed with brine (100 mL), dried and evaporated to dryness. The residue was purified by flash chromatography over silica gel using CH$_2$Cl$_2$ MeOH as eluent. The pure fractions were combined and evaporated to give 4.0 g (79%) of 44 as foam. A small quantity was crystallized from methanol as orange crystals. mp: 165–167° C. $^1$H NMR (Me$_2$SO-d$_6$) δ 2.36 (m, 1H, C$_2$H), 2.66 (m, 1H, C$_2$H), 3.60 (m, 2H, C$_5$·CH$_2$), 3.87 (m, 1H, C$_4$·H), 4.42 (m, 1H, C$_3$·H), 4.95 (t, 1H, C$_5$·OH), 5.36 (d, 1H, C$_3$·OH), 5.62 (s, 2H, ArCH$_2$), 6.34 (t, 1H, J$_{1',2'}$=6.67 Hz, C$_1$·H), 6.46 (m, 4H, ArH), 8.61 (s, 1H, C$_8$H). Anal. Calcd for C$_{17}$H$_{17}$FN$_4$O$_4$. C, 56.66; H, 4.76; N, 15.55. Found: C, 56.62; H, 4.69; N, 15.50.

Example 44

5'-O-(4,4'-Dimethoxytrityl)-2-flouro-9-(2'-deoxy-β-D-erythro-pentofuranosyl)inosine. (45)

Compound 44 (5.00 g, 13.89 mmol) was dissolved in methanol (100 mL) and placed in a parr bottle. To this solution Pd/c (5%, 1.00 g) was added and hydrogenated at 45 psi for 2 hours. The suspension was filtered, washed with methanol (50 mL) and the combined filtrate evaporated to dryness. The residue was dissolved in dry pyridine (50 mL) and evaporated to dryness. This was repeated three times and the resulting residue (weighed 4.00 g) was dissolved in dry pyridine (100 mL) under argon atmosphere. To this stirred solution was added triethylamine (1.52 g, 15.0 mmol) and 4,4'-dimethoxytrityl chloride (5.07 g, 15.0 mmol) at room temperature. The reaction mixture was allowed to stir at room temperature under argon atmosphere overnight. It was quenched with methanol (20 mL) and evaporated to dryness. The residue was dissolved in methylene chloride (200 ml) and washed with 5% NaHCO$_3$ solution (50 mL), water (50 mL), and brine (50 mL). The organic extract was dried, and evaporated to dryness. The residue was suspended in dichlormethane and the insoluble solid filtered. The filtrate was purified by flash chromatography over silica gel using CH$_2$Cl$_2$ MeOH as the eluent. The pure fractions were collected and evaporated to give 7.0 g (88%) of the title compound. The insoluble solid was found to be the DMT derivative. mp>220° C. dec: $^1$H NMR (Me$_2$SO-d$_6$) δ 2.22 (m, 1H, C$_2$·H), 2.70 (m, 1H, C$_2$·H), 3.16 (m, 2H, C$_5$·CH$_2$), 3.90 (m, 1H, C$_4$·H), 4.38 (m, 1H, C$_3$·H), 5.32 (d, 1H, C$_3$·OH), 6.16 (t, 1H, J$_{1',2'}$=6.20 Hz, C$_1$·H), 6.82 (m, 4H, ArH), 7.25 (m, 9H, ArH), 7.79 (s, 1H, C$_8$H).

Example 45

3'-O-[(N,N-Diisopropylamino) (β-cyanoethoxy) phosphanyl]-5'-O-(4,4'-dimethoxytrityl)-2-flouro-9-(2'-deoxy-β-D-erythro-pentofuranosyl)inosine. (46)

The title compound was prepared from 45 by following the procedure used for the preparation of 9. Starting materials used: 45 (7.0 g, 12.24 mmol), N,N-diisopropylethylamine (5.2 mL, 30.00 mmol), (β-cyanoethoxy) chloro(N,N-diisopropylamino)phosphane (5.9 g, 25.00 mmol) and dry CH$_2$Cl$_2$ (100 mL). The crude product was purified by flash chromatography using dichloromethane/methanol (95:5) containing 1% triethylamine as eluent. The pure fractions were pooled together and evaporated to dryness to give 7.00 g (75.5%) of 46. The foam was dissolved in dry dichloromethane (30 mL) and added dropwise into a well stirred hexane (2500 ml) under argon atmosphere. After the addition, stirring was continued for additional 1 hour and the precipitated solid was filtered, washed with hexane and dried over solid NaOH for 3 hours. The dried powder showed no traces of impurity in $^{31}$P spectrum.

SCHEME 1

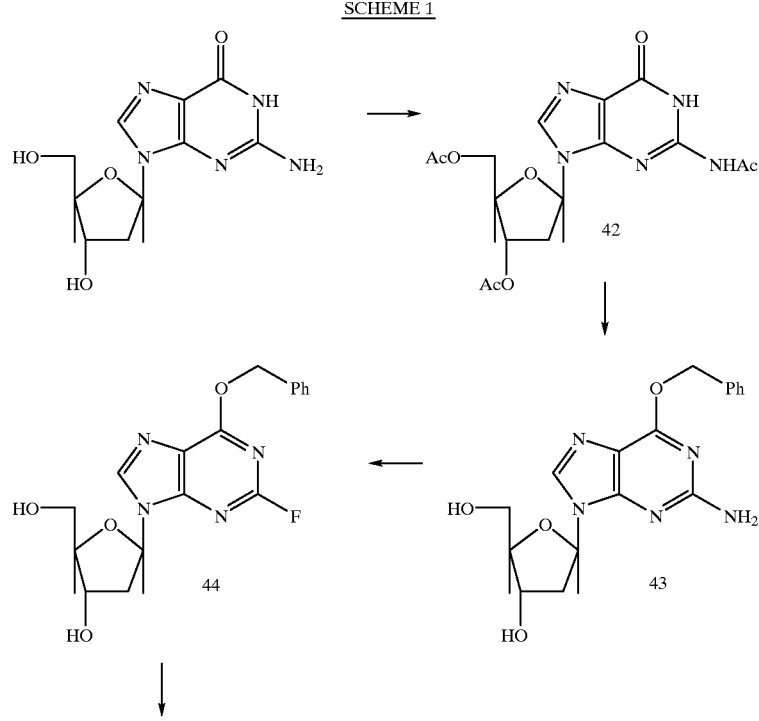

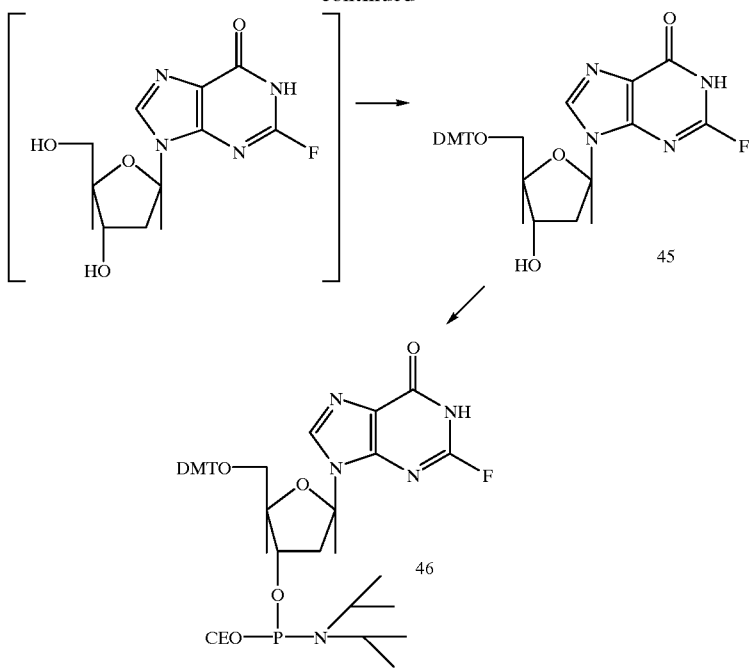

Example 46
N-[N-(tert-Butyloxycarbonyl)-3-aminopropyl]benzylamine (47).

A solution of N-(3-aminopropyl)benzylamine (38 g, 231.71 mmoles) in dry tetrahydrofuran (300 mL) was cooled to 5° C. in an ice-alcohol bath. To this cold stirred solution 2-[[(tert-butyoxycarbonyl)oxy]imino]-2-phenylacetonitrile (BOC-ON) (56.58 g, 230 mmoles) in dry tetrahydrofuran (300 mL) was added slowly during a 6 hour period. After the addition of BOC-ON, the reaction mixture was stirred at room temperature under argon for an additional 6 hours. The reaction mixture was evaporated to dryness and the residue was dissolved in ether (750 mL). The ether extract was washed with 5% sodium hydroxide solution (4×100 mL), dried over anhydrous sodium sulfate, and concentrated to dryness. The residue was purified by flash column using a chromatograpay over a silica dichloromethane→methanol gradient. The pure fractions were pooled together and evaporated to give 49.5 g (81%) of product as oil: $^1$H nmr (deuteriochloroform): δ 1.42 (s, 9H, t-Boc), 1.65 (m, 2H, $CH_2CH_2CH_2$), 2.70 (t, 2H, $CH_2NHCH_2$), 3.20 (m, 2H, $BocNHCH_2$), 3.78 (s, 2H, $ArCH_2$), 5.32 (br s, 1H, BocNH), 7.30 (m, 5H, ArH).

Example 47
10-Cyano-9-(phenylmethyl)-2,2-dimethyl-3-oxa-4-oxo-5,9-diazadecane (48).

To a stirred solution of the compound 47 (24 g, 91 mmoles) in dry acetonitrile (500 ml) was added potassium/celite (50 g) and chloroacetonitrile (27.3 g, 364 mmoles) at room temperature. The reaction mixture was placed in a preheated oil bath at 85° C. and allowed to stir at that temperature under argon for 12 hours. The reaction mixture was cooled, filtered and washed with dichloromethane (100 mL). The combined filtrate was evaporated to dryness. The residue was dissolved in dichloromethane (100 mL) and washed with 5% sodium bicarbonate solution (100 mL), water (100 mL) and brine (100 mL). The organic extract was dried over anhydrous sodium sulfate and concentrated to give a solid. The solid was crystallized from dichloromethane/hexane to give 24 g ((87%) as colorless needles, mp 70–73° C.; $^1$H nmr (deuteriochloroform): δ 1.44 (s, 9H, t-Boc), 1.71 (m, 2H, $CH_2CH_2CH_2$), 2.67 (t, 2H, J=6.4 Hz, $CH_2NHCH_2$), 3.23 (m, 2H, $BocNHCH_2$), 3.46 (s, 2H, $CH_2CN$), 3.65 (s, 2H, $ArCH_2$), 4.85 (br s, 1H, BocNH), 7.33 (s, 5H, ArH).

Anal. Calcd. for $C_{17}H_{25}N_3O_2$: C, 67.29; H, 8.31; N, 13.85, Found: C, 67.34; H, 8.45; N, 13.85.

Example 48
9,12-Di(phenylmethyl)-2,2-dimethyl-3-oxa-4-oxo-5,9,12-triazadodecane (49).

The nitrile compound of Example 47 (34 g, 112.21 mmoles) was dissolved in ethanol (100 mL) and placed in a parr hydrogenation bottle. Sodium hydroxide (7 g) was dissolved in water (20 mL), mixed with ethanol (180 mL) and added into the parr bottle. Ra/Ni (5 g, wet) was added and shaked in a parr apparatus over hydrogen (45 psi) for 12 hours. The catalyst was filtered, washed with 95% ethanol (100 mL). The combined filtrate was concentrated to 100 mL and cooled to 5° C. in an ice bath mixture. The cold solution was extracted with dichloromethane (3×200 mL). The combined extract dried over anhydrous sodium sulfate and evaporated to give 32 g (92%) of an oil product. The product was used as such for the next reaction. $^1$H nmr (deuteriochloroform): δ 1.32 (br s, 2H, $NH_2$), 1.42 (s, 9H, t-Boc), 1.67 (m, 2H, $CH_2CH_2CH_2$), 2.48 (m, 4H, $CH_2CH_2NH_2$), 2.75 (t, 2H, J=6.4 Hz, $CH_2NHCH_2$), 3.15 (m, 2H, $BocNHCH_2$), 3.55 (s, 2H, $ArCH_2$), 5.48 (br s, 1H, BocNH), 7.31 (m, 5H, ArH).

The above amine (33 g, 107.5 mmoles) in dry methanol (100 mL) was mixed with anhydrous magnesium sulfate (30 g) and allowed to stir at room temperature under argon atmosphere. To this stirred solution benzaldehyde (13.2 g, 125 mmoles) was added and the stirring was continued for 4 hours under argon. The reaction mixture was diluted with methanol (150 mL) and cooled to –5° C. in an ice salt bath. Solid sodium borohydride (30 g) was added in 1 g lots at a time during 2 hour periods, keeping the reaction temperature below 0° C. After the addition of sodium borohydride, the reaction mixture was allowed to stir at room temperature overnight and filtered over celite. The filtrate was evaporated to dryness. The residue was partitioned between water (350 mL)/ether (500 mL) and extracted in ether. The ether extract was dried over anhydrous sodium sulfate and evaporated to dryness. The residue was purified on a silica gel column using dichloromethane→methanol as eluent. The pure fractions were pooled together and evaporated to give 35 g (82%) as oil; $^1$H nmr (deuteriochloroform): δ 1.42 (s, 9H, t-Boc), 1.65 (m, 2H, $CH_2CH_2CH_2$), 1.75 (br s, 1H, $ArCH_2NH$), 2.55 (m, 4H,$CH_2CH_2$, 2.70 (t, 2H, J=6.4 Hz, $CH_2NHCH_2$), 3.15 (m, 2H, $BocNHCH_2$), 3.52 (s, 2H, $ArCH_2$), 3.72 (s, 2H, $ArCH_2$), 5.55 (br s, 1H, BocNH), 7.28 (m, 10H, ArH).

Anal. Calcd. for $C_{24}H_{35}N_3O_2$: C, 72.51; H, 8.87; N, 10.57. Found: C, 72.39; H, 8.77; H, 10.72.

Example 49

13-cyano-9,12-di(phenylmethyl)-2,2-dimethyl-3-oxa-4-oxo-5,9,12-triazatridecane (50).

The title compound was prepared from compound 49 by following the procedure used for the preparation of the compound of Example 47. Materials used: Substrate 49 (4.55 g, 11.46 mmoles); chloro acetonitrile (2.6 g, 34.38 mmoles); potassium fluoride/celite (9.0 g) and dry acetonitrile (100 mL). The crude product was purified by flash chromatography over silica gel using dichloromethane→acetone as the eluent to give 4.8 g (96%); $^1$H nmr (deuteriochloroform): δ 1.42 (s, 9H, t-Boc), 1.68 (m, 2H, $CH_2CH_2CH_2$), 2.52 (m, 4H, $CH_2CH_2$), 2.68 (t, 2H, J=6.2 Hz, $CH_2NHCH_2$), 3.22 (m, 2H, $BocNHCH_2$), 3.36 (s, 2H, $CNCH_2$), 3.50 (s, 2H, $ArCH_2$), 3.62 (s, 2H, $ArCH_2$), 5.72 (br s, 1H, BocNH), 7.32 (m, 10H, ArH).

Anal. Calcd. for $C_{26}H_{36}H_4O_2$: C, 71.52; H, 8.31; H, 12.83. Found: C, 71.17; H, 8.14; N, 12.82.

Example 50

9,12,15-Tri(phenylmethyl)2,2-dimethyl-3-oxa-4-oxo-5,9,12,15-tetraazapentadecane (51).

The title compound was prepared from compound 50 by following a two step procedure used in Example 48. Materials used in the first step: The substrate 50 (25 g, 57.34 mmoles); Ra/Ni (5 g); sodium hydroxide in ethanol (200 mL, 7 g of sodium hydroxide was dissolved in 20 mL of water and mixed with ethanol) and ethanol used to dissolve the substrate (100 mL). The crude product was extracted in dichloromethane which on evaporation gave 22 g (87%) of an oily product; $^1$H nmr (deuteriochloroform): δ 1.40 (s, 9H, t-Boc), 1.50 (m, 4H, $CH_2CH_2CH_2$ & $NH_2$), 2.48 (m, 8H, $2CH_2CH_2$), 2.66 (t, 2H, J=6.2 Hz, $CH_2NHCH_2$), 3.24 (m, 2H, $BocNHCH_2$), 3.50 (s, 2H, $ArCH_2$), 3.56 (s, 2H, $ArCH_2$), 5.48 (br s, 1H, BocNH), 7.28 (m, 10H, ArH).

Materials used in the second step: Above amine (24.4 g, 55.33 mmoles); benzaldehyde (6.36 g, 60.00 mmoles); magnesium sulfate (20.0 g) and dry methanol (200 mL). The crude product was purified by flash chromatography over silica gel using dichloromethane→methanol as the eluent to give 20.0 g (68%) of compound 51 as oil; $^1$H nmr (deuteriochloroform): δ 1.40 (s, 9H, t-Boc), 1.52 (m, 2H, $CH_2CH_2CH_2$), 1.84 (br s, 1H, $ArCH_2NH$), 2.38 (t, 2H, J=6.2 Hz, $CH_2NHCH_2$), 2.54 (m, 8H $2CH_2CH_2$), 3.08 (m, 2H, $BocNHCH_2$), 3.42 (s, 2H, $ArCH_2$), 3.50 (s, 2H, $ArCH_2$), 3.65 (s, 2H, $ArCH_2$), 3.65 (s, 2H, $ArCH_2$), 5.45 (br s, 1H, BocNH), 7.28 (m, 15H, ArH).

Anal. Calcd. for $C_{33}H_{46}N_4O_2$: C, 74.67; H, 8.74; N, 10.56. Found: C, 74.92; H, 8.39; N, 10.71.

Example 51

16-Cyano-9,12,15-tri(phenylmethyl)-2,2-dimethyl-3-oxa-oxo-5,9,12,15-tetraazahexadecane (52).

The title compound was prepared from compound 51 by following the procedure used in Example 47. Materials used: Substrate (Example 50 compound 51, 8.30 g, 15.66 mmoles); chloro acetonitrile (3.52 g, 46.98 mmoles); potassium fluoride/celite (10.0 g and dry acetonitrile (150 mL). The crude product was purified by flash chromatography over silica gel using dichloromethane→ethyl acetate as the eluent to give 7.6 g (85%); $^1$H nmr (deuteriochloroform): δ 1.42 (s, 9H, t-Boc), 1.60 (m,2H, $CH_2CH_2CH_2$), 2.42 (t, 2H, J=6.2 Hz, $CH_2NHCH_2$), 2.60 (m, 8H, $2CH_2CH_2$), 3.14 (m, 2H, $BocNHCH_2$), 3.38 (s, 2H, $CNCH_2$), 3.48 (s, 2H, $ArCH_2$), 3.54 (s, 2H, $ArCH_2$), 3.60 (s, 2H, $ArCH_2$), 5.42 (br s, 1H, BocNH), 7.26 (m, 15H, ArH).

Anal. Calcd. for $C_{35}H_{47}N_5O_2$: C, 73,77; H, 8.32; N, 12.29. Found: C, 73.69; H, 8.19; N, 12.31.

Example 52

9,12,15,18-Tetra(phenylmethyl)-2,2-dimethyl-3-oxa-4-oxo-5,9,12,15,18-petaazaoctadecane (53).

The title compound was prepared from compound 52 by following a two step procedure used for the preparation of the Example 48 compound 49. Materials used in the first step: The substrate (compound 52, 7 g, 12.30 mmoles); Ra/Ni (2 g); sodium hydroxide in ethanol (160 mL, 3.5 g of sodium hydroxide was dissolved in 10 mL of water and mixed with ethanol) and ethanol used to dissolve the substrate (100 ml). The crude product was extracted in dichloromethane which on evaporation gave 5.6 g (79%) as oil; $^1$H nmr (deuteriochloroform): δ 1.40 (s, 9H, t-Boc), 1.50 (m, 4H, $CH_2CH_2CH_2$ & $NH_2$), 2.48 (m, 12H, $3CH_2CH_2$), 2.66 (m, 2H,$CH_2NHCH_2$), 3.24 (m, 2H, $BocNHCH_2$), 3.50 (s, 2H, $ArCH_2$), 3.56 (s, 4H, 2 $ArCH_2$), 3.62 (s, 2H, $ArCH_2$), 5.48 (br s, 1H, BocNH), 7.28 (m, 15H, ArH).

Material used in the second step: above amine (21.2 g, 36.74 mmoles); benzaldehyde (4.24 g, 40.00 mmoles); magnesium sulfate (10.0 g), dry methanol (200 mL) and sodium borohydride (4.85 g, 128.45 mmoles). The crude product was purified by flash chromatography over silica gel using dichloromethane→methanol as the eluent to give 18.67 g (77%) of compound 53 as oil; $^1$H nmr (deuteriochloroform): δ 1.40 (s, 9H, t-Boc), 1.52 (m, 2H, $CH_2CH_2CH_2$), 2.05 (br s, 1H, $ArCH_2NH$), 2.38 (t, 2H, J=6.0 Hz, $CH_2NHCH_2$), 2.54 (m, 12H, 2 $CH_2CH_2$), 3.08 (m, 2H, $BocNHCH_2$), 3.40 (s, 2H, $ArCH_2$), 3.50 (s, 4H, 2 $ArCH_2$), 3.64 (s, 2H, $ArCH_2$), 5.55 (br s, 1H, BocNH), 7.28 (m, 20H, ArH).

Anal. Calcd. for $C_{42}H_{57}N_5O_2$: C, 75.98; H, 8.65; N, 10.55. Found: C, 75.72; H, 8.67; N, 10.39.

Example 53

13-amino-1,4,7,10-tetra(phenylmethyl)-1,4,7,10-tetraazatridecane (54).

To a stirred solution of compound 53 (2.65 g, 4 mmoles) in dichloromethane (10 mL) was added trifluoroacetic acid (10 mL) at room temperature. The reaction mixture was allowed to stir at room temperature for 30 minutes and evaporated to dryness. The residue was dissolved in dichloromethane (100 mL) and washed with 5% sodium bicarbonate solution (150 mL) to pH 8, and brine (50 mL). The organic extract was dried over anhydrous sodium sulfate and concentrated to dryness. The oily residue that obtained was used as such for the next reaction. $^1$H nmr (deuteriochloroform): δ 1.50 (m, 5H, $CH_2CH_2CH_2$, $NH_2$, & $ArCH_2NH$), 2.38 (t, 2H, J=6.4 Hz, $CH_2NHCH_2$), 2.54 (m, 14H, 7 $CH_2$), 3.52 (s, 2H, $ArCH_2$), 3.56 (s, 4H, 2 $ArCH_2$). 3.62 (s, 2H, $ArCH_2$), 7.28 (m, 20H, ArH).

SCHEME 2

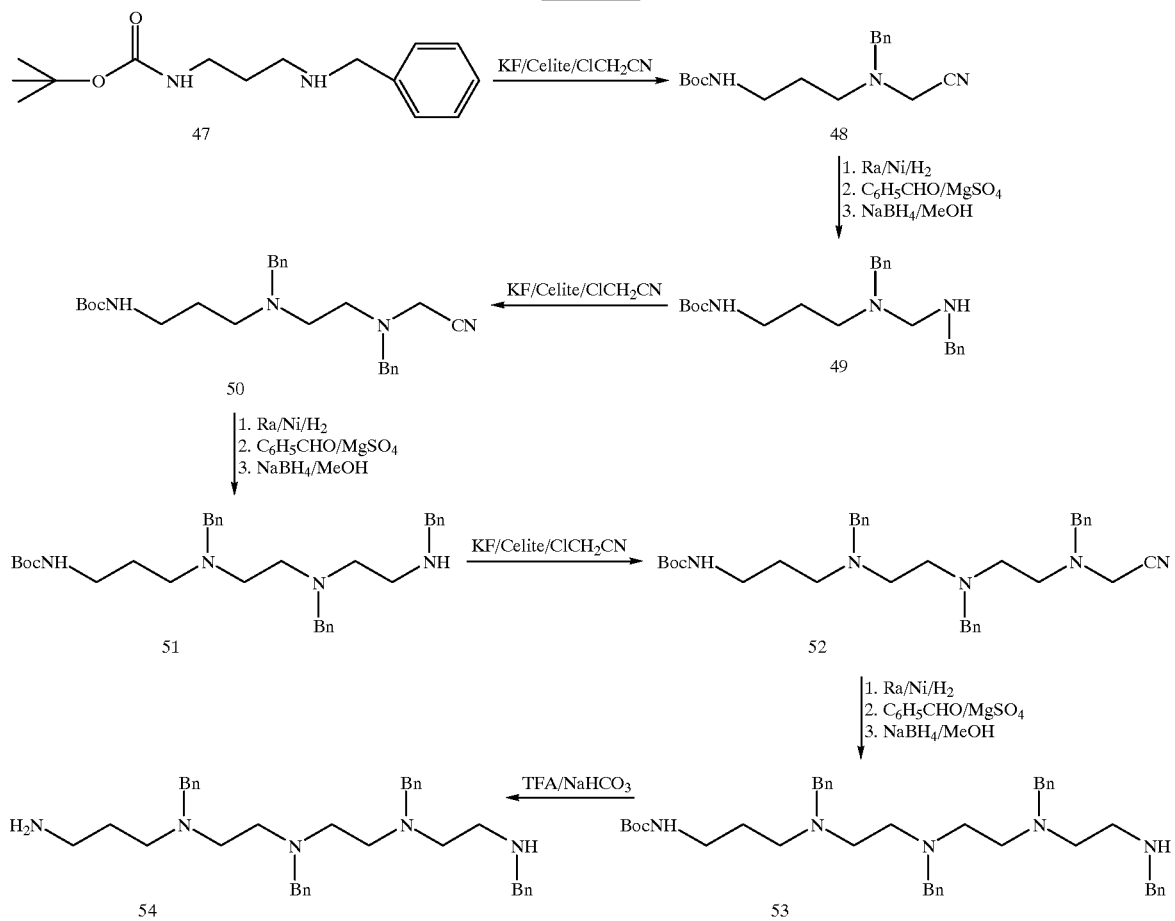

Example 54
3',5'-O-(Tetraisopropyldisiloxane-1 3-diyl)-N-[4,7,10,13-tetrakis-(phenylmethyl)-4,7,10,13-tetraazatridec-1-yl]-2'-deoxyquanosine (56).

A mixture of 2-chloroinosine (55 in reaction scheme 3, 2.12 g, 4 mmoles) and compound 54 (2.5 g, 4.4 mmoles) in 2-methoxyethanol (50 mL) was heated at 80° C. for 12 hours. The reaction mixture was evaporated to dryness and the residue on flash chromatography over silica gel using dichloromethane and methanol (9:1) gave 2.55 g (60%) of the title compound as foam. $^1$H nmr (deuteriochloroform): δ 1.00 (m, 24H, 4 Isobutyl-H), 1.62 (m, 1H, $C_2$H), 1.80 (m, 4H, $CH_2CH_2CH_2$, $C_2$H, & $ArCH_2NH$), 2.52 (m, 14H, 7 $CH_2$), 3.20 (s, 2H, ArCH), 3.32 (s, 2H, $ArCH_2$), 3.42 (s, 2H, $ArCH_2$), 3.48 (s, 4H, $ArCH_2$ & $CH_2$), 3.78 (m, 1H, $C_4$H), 4.05 (m, 2H, $C_5$,$CH_2$), 4.72 (m, 1H, $C_3$H), 6.22 (m, 1H, $C_1$H), 6.94 (m. 1H, $N_2$H), 7.26 (m, 20H, ArH), 7.72 (s, 1H, $C_8$H), 10.52 (br s, 1H, NH).

Anal. Calcd. for $C_{59}H_{85}N_9O_5Si_2$: C, 67.07; H, 8.11; N, 11.93. Found: C, 67.22; H, 8.24; N, 11.81.

Example 55
3',5'-O-(Tetraisopropyldisiloxane-1,3-diyl)-6-O-(phenylmethyl)-N-[15-methyl-14-oxo-4,7,10,13-tetrakis (phenylmethyl)-4,7,10,13-tetraazahexadec-1-yl]-2'-deoxyguanosine (57).

The compound of Example 54 (2.00 g, 1.89 mmoles) was coevaporated with dry pyridine (30 mL) two times. The resulting residue was dissolved in dry pyridine (50 mL) and cooled to 0° C. in an ice bath mixture. To this cold stirred solution was added triethylamine (0.61 g, 6 mmoles) followed by isobutyryl chloride (0.64 g, 6 mmoles) slowly under argon atmosphere. After the addition of isobutyryl chloride, the reaction mixture was stirred at room temperature for 12 hours and evaporated to dryness. The residue was dissolved in dichloromethane (150 mL), washed with 5% sodium bicarbonate (50 mL), water (50 mL) and brine (50 mL). The organic extract was dried over anhydrous sodium sulfate and evaporated to dryness. The residue on purification over silica gel using dichloromethane/methanol (95:5) gave 1.88 g (88%) of the title compound as a foam.

The above foam (1.8 g, 1.61 mmoles) was dried over phosphorous pentaoxide under vacuum for 12 hours. The dried residue was dissolved in dry dioxane (50 mL) and treated with triphenyl phosphine (0.83 g, 3.2 mmoles), benzyl alcohol (0.35 g, 3.2 mmoles), and diethylazodicarboxylate (0.54 g, 3.2 mmoles) at room temperature under argon atmosphere. The reaction mixture after stirring for 10 hours evaporated to dryness. The residue was dissolved in dichloromethane (150 mL) and washed with 5% sodium bicarbonate (50 mL), water (50 mL) and brine (50 mL). The organic extract was dried over anhydrous sodium sulfate and evaporated to dryness. The residue was flash chromatographed over silica gel using dichloromethane/acetone (7:3) as the eluent. The pure fractions were collected together and evaporated to give 1.7 g (74%) of foam: $^1$H nmr (deuteriochloroform): δ 1.04 (m, 30H, 5 Isobutyl-$CH_3$), 1.68 (m, 2H, $CH_2CH_2CH_2$), 2.55 (m, 16H, 7 $CH_2$, $C_2$H, & isobutyl-CH), 3.08 (m, 1H, $C_2$H), 3.36 (m, 2H, $CH_2$), 3.52

(m, 8H, 4 ArCH$_2$), 3.84 (m, 1H, C$_{4'}$H), 4.00 (m, 2H, C$_{5'}$CH$_2$), 4.72 (m, 1H, C$_{3'}$H), 5.50 (s, 2H, ArCH$_2$), 6.18 (m, 1H, C$_{1'}$H), 7.04 (m, 1H, N$_2$H), 7.26 (m, 25H, ArH), 7.76 (s, 1H, C$_8$H).

Anal. Calcd. for C$_{70}$H$_{97}$N$_9$O$_6$Si$_2$: C, 69.09; H, 8.04; N, 10.36. Found: C, 69.12; H, 8.23; N, 10.19.

Example 56
6-O-(Phenylmethyl)-N-[15-methyl-14-oxo-4,7,10,13-tetrakis(phenylmethyl)-4,7,10,13-tetraazahexadec-1-yl]-2'-deoxyguanosine (58).

To a stirred solution of compound 57 (5.0 g, 4.11 mmoles) in pyridine (50 mL) was added freshly prepared 1N solution of tetrabutylammonium fluoride (20 mL, 20 mmoles; prepared in a mixture of pyridine:tetrahydrofuran:water in the ratio of 5:4:1) at room temperature. The reaction mixture was allowed to stir for 30 minutes and quenched with H$^+$ resin (pyridinium form) to pH 6–7. The resin was filtered, washed with methanol (50 mL), and the combined filtrate evaporated to dryness. The residue was dissolved in dichloromethane (200 mL), washed with water (50 mL), and brine (50 mL). The organic extract was dried over sodium sulfate and concentrated to dryness. The foam that obtained was purified by flash chromatography over silica gel column using dichloromethane/methanol (95:5) as the eluent. The required fractions were collected together and evaporated to give 3.5 g (87%) of the titled compound as foam. $^1$H nmr (deuteriochloroform): δ 1.04 (m, 30H, 5 isobutyryl CH$_3$), 1.68 (m, 2H, CH$_2$CH$_2$CH$_2$), 2.55 (m, 16H, 7 CH$_2$, C$_{2'}$H, & isobutyryl CH), 3.08 (m, 1H, C$_{2'}$H), 3.36 (m, 2H, CH$_2$), 3.52 (m, 8H, 4 ArCH$_2$), 3.84 (m, 1H, C$_{4'}$H), 4.00 (m, 2H, C$_{5'}$CH$_2$), 4.72 (m, 1H, C$_{3'}$H), 5.50 (s, 2H, ArCH$_2$), 6.18 (m, 1H, C$_{1'}$H), 7.04 (m, 1H, N$_2$H), 7.26 (m, 25H, ArH), 7.76 (s, 1H, C$_8$H).

Anal. Calcd. for C$_{70}$H$_{97}$N$_9$O$_6$Si$_2$: C, 69.09; H, 8.04; N, 10.36. Found: C, 69.12; H, 8.23; N, 10.19.

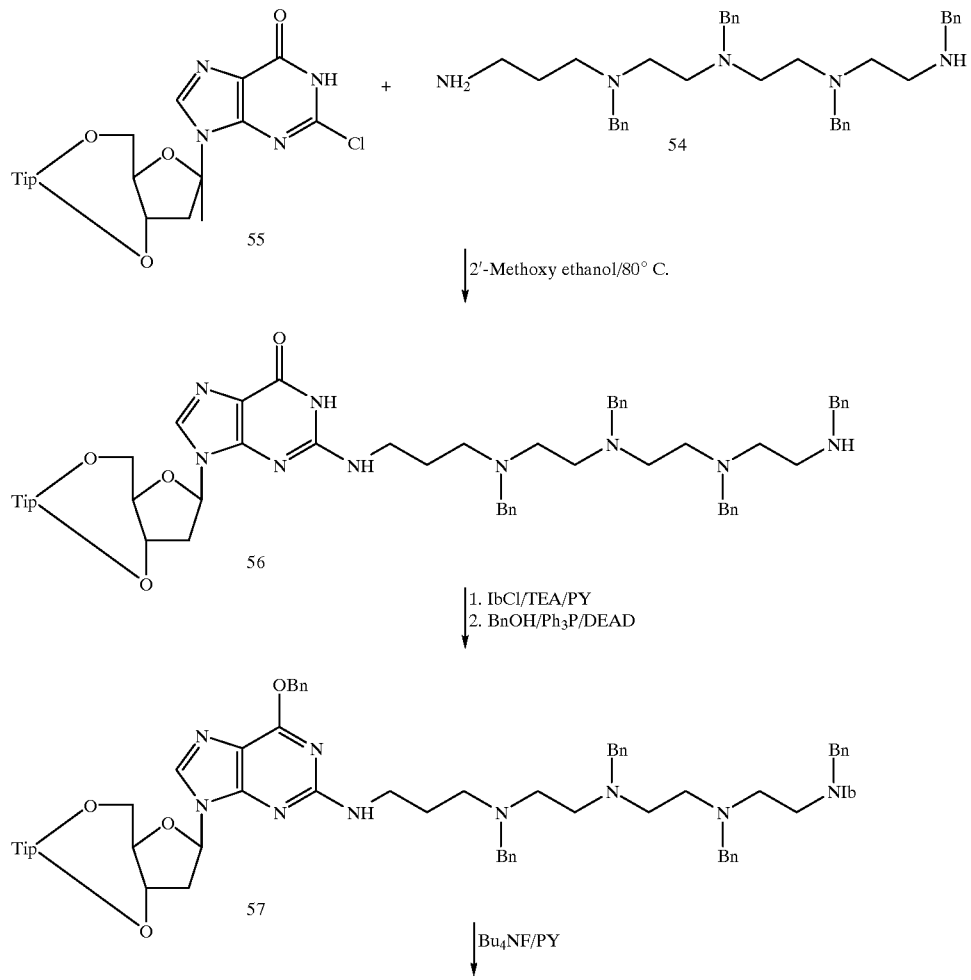

SCHEME 3

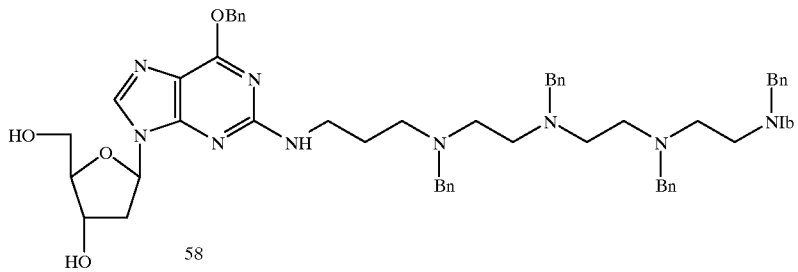

58

Example 57

The amidites 9, 17, 23, 30, 35, 41 and 46, as discussed in the Detailed Description of the Preferred Embodiments, are incorporated into oligonucleotide sequences via automated DNA synthesis protocol. (Standard protocol using an ABI 380B DNA synthesizer was modified by increasing the wait step after the pulse delivery of tetrazole to 900 seconds. Deprotection conditions are discussed in Himmelsbach, et al., *Tetrahedron*, 1984, 40, 59). Enzymatic degradation and subsequent HPLC analysis indicated the expected ratios of the nucleoside components. (Oligonucleotides were digested with a mixture of spleen phosphodiesterase, snake venom phosphodiesterase, and bacterial alkaline phosphatase to provide individual nucleosides which were analyzed by HPLC).

A 21-mer oligonucleotide [5'd-(GCCGAGGTCCATGTCGTACGC)] was modified with one, three or seven $N^2$-[3-(1H-imidazol-1-yl)propyl)dGs or one or three $N^2$-[3-(1H-imidazol-1-yl)propyl]-2-$NH_2$ dAs and hybridized to complementary DNA or RNA. See Freier et al., *Gene Regulation: Biology of Antisense RNA and DNA*, (Erickson, et al. Raven Press, New York, 1992), pp. 95–107; Breslauer, et al., *Proc. Nat'l Acad. Sci. USA*, 1991, 8, 3746. Compared to unmodified DNA, the average change $T_m$/mod was +2.0 and +0.3 for dG modified oligonucleotides hybridized with DNA and RNA, respectively; the average change $T_m$/mod was +2.7 and +0.6 for dA modified oligonucleotides hybridized with DNA and RNA, respectively. The average enhancement of binding affinity of several different $N^2$-imidazolpropyl dG and $N^2$-imidazolpropyl-2-amino-dA modified oligonucleotides hybridized to DNA is 2.7 degrees Celsius/mod (3 different sequences, 16 incorporations) and 2.5 degrees Celsius/mod (3 different sequences, 12 incorporations), respectively. The relative specificity of hybridization of dG or $N^2$-imidazolpropyl dG to cytidine versus A, G, and U(T) mismatches of an RNA or DNA complement shows that $N^2$-modified dG is more specific to its complement cytidine than the corresponding unmodified dG; $N^2$-imidazolpropyl-2-$NH_2$ dA is as specific as dA against RNA or DNA. Incorporation of three $N^2$-imidazolpropyl-2-$NH_2$ dGs or 2-$NH_2$-dAs at the n-1, n-2, and n-3 positions at the 3' end of a 15-mer provided an increase in stability ($T_{1/2}$=9 and 16 h, respectively) to nucleolytic degradation in fetal calf serum compared to the unmodified oligomer ($T_{1/2}$=1h). See Hoke et al., *Nucleic Acids Res.*, 1991, 8, 3746. The capped $N^2$-modified dG sequence was stabilized by 2.8 degrees Celsius/mod against DNA and 0.9 degrees Celsius against RNA, and the 2-$NH_2$-dA sequence was stabilized by 2.6 degrees Celsius/mod against DNA and 1.5 degrees/Celsius against RNA.

Molecular modeling simulations of oligomers containing the $N^2$-imidazolpropyl functionality suggest that the imidazole binds in the minor groove proximate to the phosphate backbone, stabilizing the DNA—DNA duplex. (Molecular minimization and dynamics studies were conducted using the Amber forcefield with the Insight and Discover programs (Biosys Inc., San Diego, Calif.). Four thousand steps of conjugate gradient minimization were used, followed by 1000 cycles of equilibration at 300 degrees Celsius, and 4000 steps of dynamics at 10 psec intervals). In the case of the RNA-DNA duplex, the imidazolpropyl group does not bind specifically since the minor groove is broad and the phosphates are turned away. However, other hydrogen bond donors and acceptors are accessible in the minor groove, which may account for the increased stability of the modified duplex.

A 21-mer having imidazolpropyl modified dG in 7 positions (1,4,6,7,13,16, and 20) and another 21-mer having imidazolpropyl modified 2-$NH_2$-dA in 5 positions (1,5,8,11, and 18) support HeLa cell extract RNase H dependent cleavage. Agrawal, et al., *Proc. Nat'l Acad. Sci. USA*, 1989, 87, 1401. Furthermore, a 17-mer phosphorothioate containing a modified dG at the primary cleavage site of HeLa cell extract RNase H did not prevent cleavage by the enzyme. Monia, et al., *Biol. Chem.*, submitted 1992. These data suggest the heteroduplexes formed between $N^2$-imidazolpropyl dG or 2-$NH_2$-dA modified oligonucleotides and RNA are recognized by RNase H. The following Table 1 is illustrative of these studies.

TABLE 1

MODIFIED OLIGONUCLEOTIDES AND THEIR HYBRIDIZATION PROPERTIES

| Sequences | Mod | $\Delta\Delta G°_{37}$ | Wild(Tm) | Mod(Tm) | $\Delta T_m$ | $\Delta T_m$/Mod |
|---|---|---|---|---|---|---|
| Against DNA | | | | | | |
| GCC TG'A TCA GGC* | 1 | -4.33 | 50.7 | 63.4 | +12.7 | +6.4 |
| GCC GAG GTC CAT G'TC GTA CGC | 1 | -0.25 | 69.7 | 72.3 | +2.6 | +2.6 |
| GCC G'AG GTC CAT G'TC GTA CG'C | 3 | +0.05 | 69.7 | 75.8 | +6.1 | +2.0 |
| G'CC G'AG' G'TC CAT G'TC G'TA CG'C | 7 | -4.30 | 69.7 | 83.3 | +13.6 | +1.9 |
| CGA CTA TGC AAG' G'G'C | 3 | -2.01 | 56.5 | 64.9 | +8.4 | +2.8 |
| CGA CTA TGC AAA' A'A'C | 3 | -2.86 | 50.5 | 58.1 | +7.6 | +2.6 |

TABLE 1-continued

MODIFIED OLIGONUCLEOTIDES AND THEIR HYBRIDIZATION PROPERTIES

| Sequences | Mod | $\Delta\Delta G°_{37}$ | Wild(Tm) | Mod(Tm) | $\Delta T_m$ | $\Delta T_m$/Mod |
|---|---|---|---|---|---|---|
| A'CC GA'G GA'T CA'T GTC GTA' CGC | 5 | −1.41 | 66.1 | 77.6 | +11.5 | +2.3 |
| GCC GA'G GTC CA'T GTC GTA' CGC | 3 | +1.31 | 69.7 | 77.6 | +7.9 | +2.6 |
| GCC GAG GTC CA'T GTC GTA CGC | 1 | +3.10 | 69.7 | 72.4 | +2.7 | +2.7 |
| aCC GaG GTC CaT GTC GTa CGC | 5 | +0.49 | 66.1 | 69.4 | +3.09 | +0.6 |
| GCC GAG GTC CaT GTC GTA CGC | 1 | +2.15 | 69.7 | 70.9 | +1.25 | +1.3 |
| Against RNA | | | | | | |
| GCC GAG GTC CAT G'TC GTA CGC | 1 | −0.39 | 69.1 | 69.6 | +0.5 | +0.5 |
| GCC G'AG GTC CAT G'TC GTA CG'C | 3 | −0.15 | 69.1 | 70.3 | +1.2 | +0.4 |
| G'CC G'AG' G'TC CAT G'TC G'TA CG'C | 7 | +3.10 | 69.1 | 70.4 | +1.3 | +0.2 |
| CGA CTA TGC AAA' A'A'C | 3 | −1.24 | 39.0 | 43.4 | +4.4 | +1.5 |
| A'CC GA'G GA'T CA'T GTC GTA' CGC | 5 | +1.59 | 63.2 | 65.9 | +2.7 | +0.5 |
| GCC GA'G GTC CA'T GTC GTA' CGC | 3 | +2.86 | 69.1 | 71.2 | +2.1 | +0.7 |
| GCC GAG GTC CA'T GTC GTA CGC | 1 | +3.41 | 69.1 | 69.5 | +0.4 | +0.4 |

*Self Complementary; A' = $N_2$-Imidazolylpropyl dA; G' = $N_2$-Imidazolylpropyl dG

Example 58
Chromatography and Purification.

Silica gel used for flash chromatography was ICN 60 (Costa Mesa, Calif.), 32–63 mesh. Materials not soluble in the solvent system used for flash chromatography (FC) were coevaporated onto E. Merck silica gel 100 (Darmstadt, Republic of Germany), 70–230 mesh, using a suitable solvent. The dry materials were then applied to the top of a FC column. TLC was performed on prescored E. Merck Kieselgel 60 $F_{254}$ plates. Compounds were visualized by illuminating TLC plates under UV light (254 nm) and/or by spraying with 10 methanolic $H_2SO_4$ followed by heating. Evaporations were carried out at 40–50° C. using a rotary evaporator and a vacuum pump coupled to a vacuum controller. $^1$H-NMR spectra were obtained at 400 mHz in dmso-$d_6$ unless otherwise noted. Where relevant, treatment of samples with $D_2O$ recorded exchangeable protons. Infrared spectra were recorded on a Perkin-Elmer 16PC FT-IR spectrophotometer. Solvent system A=ethyl acetate-hexanes, 3:2; B=ethyl acetate-methanol, 9:1, v/v.

Example 59
Procedure for attaching modified 5'-dimethoxytriphenylmethyl ribonucleosides to the 5'-hydroxyl of nucleosides bound to CPG support.

The modified nucleosides that will reside in the terminal 3'-position of certain antisense oligonucleotides are protected as their 5'-DMT (the cytosine and adenine exocyclic amino groups are benzoylated and the guanine amino is isobutyrlated) and treated with trifluoroacetic acid/bromoacetic acid mixed anhydride in pyridine and dimethylaminopyridine at 50° C. for five hours. The solution is evaporated under reduced pressure to a thin syrup which is dissolved in ethyl acetate and passed through a column of silica gel. The homogenous fractions were collected and evaporated to dryness. A solution of 10 mL of acetonitrile, 10 micromoles of the 3'-O-bromomethyl-ester modified pyrimidine nucleoside, and one mL of pyridine/dimethylaminopyridine (1:1) is syringed slowly (60 to 90 sec) through a one micromole column of CPG thymidine (Applied Biosystems, Inc.) that had previously been treated with acid according to standard conditions to afford the free 5'-hydroxyl group. Other nucleosides bound to CPG columns could be employed. The eluent is collected and syringed again through the column. This process is repeated three times. The CPG column with 10 mL of acetonitrile and then attached to an ABI 380B nucleic acid synthesizer. Oligonucleotide synthesis is now initiated. The standard conditions of concentrated ammonium hydroxide deprotection that cleaves the thymidine ester linkage from the CPG support also cleaves the 3',5' ester linkage connecting the pyrimidine modified nucleoside to the thymidine that was initially bound to the CPG nucleoside. In this manner, any modified nucleoside or generally any nucleoside with modifications in the heterocycle and/or sugar can be attached at the 3' end of an oligonucleotide sequence.

Example 60
Procedure for the conversion of modified nucleoside-5'-DMT-3'-phosphoramidites into oligonucleotides.

The polyribonucleotide solid phase synthesis procedure of Sproat, et al., 1989, *Nucleic Acids Res.*, 17, 3373–3386 is used to prepare the modified oligonucleotides.

Example 61
Preparation of Modified Phosphorothioate Oligonucleotides.

Substituted 5'-DMT nucleoside 3'-phosphoroamidites prepared as described in the above Examples are inserted into sequence specific oligonucleotide phosphorothioates as described by Sproat, supra, at 3373–3386 and Beaucage, et al., J. Am. Chem. Soc'y, 1989, 112, 1253–1255.

Example 62
3',5'-O-(Tetraisopropyldisiloxane-1,3-diyl)-$N^5$-(ethyl-S-benzyl)-2'-deoxyguanosine.

A mixture of 2-chloroinosine (4 mmol) and 2-(benzylthio)-ethylamine (4.4 mmol) is heated at 80° C. for 12 hours in 2-methoxyethanol (50 mL). The reaction mixture is evaporated to dryness and the residue is purified by silica gel flash column chromatography using dichloromethane and methanol (9:1) to give the title compound.

Example 63
3',5'-O-(Tetraisopropyldisiloxane-1,3-diyl)-$N^5$-(ethyl-S-benzyl)-6-O-benzyl-2'-deoxyguanosine.

The compound of Example 1 (1.89 mmol) is dissolved in anhydrous dioxane (50 mL) and treated with triphenyl phosphine (3.2 mmol), benzyl alcohol (3.2 mmol) and diethylazodicarboxylate (3.2 mmol) at room temperature under argon. The reaction mixture is stirred for 10 hours and then evaporated to dryness. The residue is dissolved in dichloromethane (150 mL) and washed with 5% sodium bicarbonate (50 mL), water (50 mL) and brine (50 mL). The organic extract is dried over anhydrous sodium sulfate and evaporated to dryness. The residue is purified by silica gel flash column chromatography using dichloromethane and acetone (7:3) as the eluent. The appropriate fractions are pooled together and the solvent evaporated to yield the title compound.

Example 64
N[5]-(Ethyl-S-benzyl)-6-O-benzyl-2'-deoxyguanosine.

To a stirred solution of the compound of Example 2 (4.11 mmol) in pyridine (50 mL) is added a freshly solution of 1 N tetrabutylammonium fluoride (20 mmol) in pyridine:THF:water (5:4:1) at room temperature. The reaction mixture is allowed to stir for 30 minutes and then quenched with H[+] resin (pyridinium form) to pH 6–7. The resin is filtered, washed with methanol (50 mL), and the combined filtrate is evaporated to dryness. The residue is dissolved in dichloromethane (200 mL), and washed with water (50 mL) and brine (50 mL). The organic extract is dried over anhydrous sodium sulfate and evaporated to dryness. The residue is purified by silica gel flash column chromatography using dichloromethane-methanol (18:1) as the eluent, yielding the title compound.

Example 65
Deprotection of the thiol protecting group.

The compound of Example 3 is converted to the 5'-DMT-nucleoside-3'-phosphoramidite and incorporated into an oligonucleotide according to the procedure of Example 61. For deprotecting the thiol group (S-benzyl), the oligonucleotide is treated with sodium in boiling ethanol according to the procedure described in *J. Am. Chem. Soc.*, 71, 1253 (1949).

Example 66
3-Amino-(1-O-benzyloxymethyl)propanol.

3-Aminopropanol is converted to its O-benzyloxymethyl ether by reacting it with benzyloxymethyl chloride and N,N-diisopropylethylamine at 10–20° C., for 12 hours, according to the procedure of Stork and Isobe [*J. Am. Chem. Soc.*, 97, 6260 (1975)].

Example 67
3',5'-O-(Tetraisopropyldisiloxane-1,3-diyl)-N[5]-(propyloxymethyloxybenzyl)-2'-deoxyguaosine.

A mixture of 2-chloroinosine (4 mmol) and the compound of Example 5 (4.4 mmol) is heated at 80° C. for 12 hours in 2-methoxyethanol (50 mL). The reaction mixture is evaporated to dryness and the residue is purified by silica gel flash column chromatography using dichloromethane and methanol (9:1) to give the title compound.

Example 68
3',5'-O-(Tetraisopropyldisiloxane-1,3-diyl)-N[5]-(propyloxymethyloxybenzyl)-6-O-benzyl-2'-deoxyguanosine.

The compound of Example 6 (1.89 mmol) is dissolved in anhydrous dioxane (50 mL) and treated with triphenyl phosphine (3.2 mmol), benzyl alcohol (3.2 mmol) and diethylazodicarboxylate (3.2 mmol) at room temperature under argon. The reaction mixture is stirred for 10 hours and then evaporated to dryness. The residue is dissolved in dichloromethane (150 mL) and washed with 5% sodium bicarbonate (50 mL), water (50 mL) and brine (50 mL). The organic extract is dried over anhydrous sodium sulfate and evaporated to dryness. The residue is purified by silica gel flash column chromatography using dichloromethane and acetone (7:3) as the eluent. The appropriate fractions are pooled together and the solvent evaporated to yield the title compound.

Example 69
N[5]-(Propyloxymethyloxybenzyl)-6-O-benzyl-2'-deoxyguanosine.

To a stirred solution of the compound of Example 7 (4.11 mmol) in pyridine (50 mL) is added a freshly solution of 1 N tetrabutylammonium fluoride (20 mmol) in pyridine:THF:water (5:4:1) at room temperature. The reaction mixture is allowed to stir for 30 minutes and then quenched with H[+] resin (pyridinium form) to pH 6–7. The resin is filtered, washed with methanol (50 mL), and the combined filtrate is evaporated to dryness. The residue is dissolved in dichloromethane (200 mL), and washed with water (50 mL) and brine (50 mL). The organic extract is dried over anhydrous sodium sulfate and evaporated to dryness. The residue is purified by silica gel flash column chromatography using dichloromethane-methanol (18:1) as the eluent, yielding the title compound.

Example 70
Deprotection of the hydroxyl protecting group.

The compound of Example 8 is converted to the 5'-DMT-nucleoside-3'-phosphoramidite and incorporated into an oligonucleotide according to the procedure of Example 61. For deprotecting the hydroxyl group (O-methyloxybenzyl), the oligonucleotide is treated with sodium and ammonia in ethanol according to the procedure described in *J. Am. Chem. Soc.*, 97, 6260 (1975).

Example 71
Derivatization of the hydroxyl group to an aldehyde functionality.

The compound of Example 9 is converted to the N[5]-ethylformyl derivative by treating it with Pb(OAc)$_4$ and Mn(OAc)$_2$ according to the procedure described in *Tet. Lett.*, 27, 2287 (1986).

Example 72
Derivatization of the hydroxyl group to a halo group.

The compound of Example 9 is converted to the N[5]-chloropropyl derivative by treating it with (COCl)$_2$ and DMF according to the procedure described in *J. Am. Chem. Soc.*, 107, 3285 (1985).

Each of the published documents mentioned in this specification are herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

What is claimed is:

1. A method for the preparation of a compound of Formula I:

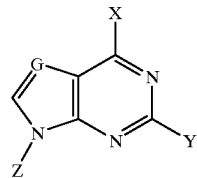

wherein
G is CH or N;
X is NH$_2$ or OH;
Y is RQ or NHRQ, wherein said R is a hydrocarbyl group having from 2 to about 20 carbon atoms; and Q is H, NH$_2$, polyalkylamino, hydrazines, hydroxylamines, semicarbazides, thiosemicarbazides, hydrazones, hydrazides, imidazoles, imidazole amides, alkylimidazoles, tetrazole, triazole, pyrrolidine, piperidine, piperazine, morpholine, thiols, aldehydes, ketones, alcohols, alkoxy groups, or halogens or alkoxy groups; and Z is H, ribose or deoxyribose; comprising:
  providing a compound of Formula I wherein Y is halogen; and
  contacting said compound with a compound of Formula RQ or NHRQ, wherein R is a hydrocarbyl group having from 2 to about 20 carbon atoms; and Q is H, $NH_2$, polyalkylamino, a hydrazine, a hydroxylamine, a semicarbazide, a thiosemicarbazide, a hydrazone, a hydrazide, an imidazole, an imidazole amide, an alkylimidazole, a tetrazole, a triazole, a pyrrolidine, a piperidine, a piperazine, a morpholine, a thiol, an aldehyde, a ketone, an alcohol, or an alkoxy group;
  under conditions of time, temperature and pressure sufficient to form said compound of Formula I.

2. The method of claim 1 wherein X is OH.
3. The method of claim 1 wherein G is N.
4. The method of claim 1 wherein X is OH and G is N.
5. The method of claim 4 wherein said compound of Formula I wherein Y is halogen is contacted with a compound of Formula RQ.
6. The method of claim 4 wherein said compound of Formula I wherein Y is halogen is contacted with a compound of Formula NHRQ.
7. The method of claim 5 wherein Q is a substituted or unsubstituted imidazole.
8. The method of claim 6 wherein Q is a substituted or unsubstituted imidazole.
9. The method of claim 7 wherein Q is imidazole.
10. The method of claim 8 wherein Q is imidazole.
11. The method of claim 4 wherein Q is a methylimidazole.
12. The method of claim 5 wherein Q is a methylimidazole.
13. The method of claim 54 wherein Q is alkane having from 5 to 20 carbon atoms.
14. The method of claim 5 wherein Q is alkane having from 5 to 20 carbon atoms.
15. The method of claim 4 wherein Q is isobutyrylnonane.
16. The method of claim 5 wherein Q is isobutyrylnonane.
17. The method of claim 4 wherein Q is amine, wherein said amine is a polyalkylamine or an aminoalkylamine.
18. The method of claim 5 wherein Q is an amine, wherein said amine is a polyalkylamine or an aminoalkylamine.
19. The method of claim 4 wherein Q is an imidazole, an imidazole amide, an alkylimidazole, a tetrazole, a triazole, a pyrrolidine, a piperidine, a piperazine, a morpholine or a heterocycloamine.
20. The method of claim 5 wherein Q is an imidazole, an imidazole amide, an alkylimidazole, a tetrazole, a triazole, a pyrrolidine, a piperidine, a piperazine, a morpholine or a heterocycloamine.
21. The method of claim 4 wherein Q is a substituted or unsubstituted imidazole.
22. The method of claim 5 wherein Q is a substituted or unsubstituted imidazole.

* * * * *

UNITED STATES PATENT AND TRADEMARK OFFICE
CERTIFICATE OF CORRECTION

PATENT NO.    : 6,166,199
DATED         : December 26, 2000
INVENTOR(S)   : Cook et al.

It is certified that error appears in the above-identified patent and that said Letters Patent is hereby corrected as shown below:

Title page,
Item [56], OTHER PUBLICATIONS,
Under "8th Ikehara, M.", please delete "LXXXIV" and insert therefor -- LXXIV --;
Under "Stufkens, D.J.", please delete "$SeCl^6 2-$, $SeBr^6 2 TeCl^6 2$ and $TeBr^6 2-$" and insert therefor $SeCl^6_2-$, $SeBr^6_2-$ and $TeCl^6_2$, and $TeBr^6_2-$", --;
Under "Seela, F. and Kehne", please delete "35" and insert therefor -- 26 --;

Column 14,
Line 16, please delete "NH," and insert therefor -- $NH_2$ --;

Column 28,
Line 16, please delete "$2OCH_3$" and insert therefor -- $2\ OCH_3$ --;

Column 30,
Line 23, please delete "$2OCH_3$)" and insert therefor -- $2\ OCH_3$) --;

Column 52,
Line 5, please delete "54" and insert therefor -- 4 --;

Signed and Sealed this

Fifteenth Day of October, 2002

Attest:

JAMES E. ROGAN
Attesting Officer        Director of the United States Patent and Trademark Office